United States Patent [19]

George

[11] Patent Number: 4,818,277

[45] Date of Patent: Apr. 4, 1989

[54] ALKYL SULFONES

[75] Inventor: Levitt George, Wilmington, Del.

[73] Assignee: E. I. Du Pont de Nemours and Company, Wilmington, Del.

[21] Appl. No.: 395,782

[22] Filed: Jul. 12, 1982

Related U.S. Application Data

[63] Continuation-in-part of Ser. No. 227,886, Jan. 28, 1981, abandoned, which is a continuation-in-part of Ser. No. 134,287, Mar. 26, 1980, abandoned.

[51] Int. Cl.$^4$ .................... A01N 43/54; C07D 239/02
[52] U.S. Cl. ................................ 71/92; 71/93; 544/218; 544/219; 544/321; 544/330; 544/332
[58] Field of Search ............... 544/330, 332, 321; 71/92

[56] References Cited

FOREIGN PATENT DOCUMENTS 1468747 2/1967 France .

OTHER PUBLICATIONS

Logemann et al., Chem. Abst., vol. 53, (1959), 18052g.
Wojciechowski, Chem. Abst., vol. 59, (1962), 1633e.
Levitt, German Offen. 2,715,786, Chem. Abst., vol. 88, (1978), 6935x.

*Primary Examiner*—Catherine L. Mills

[57] ABSTRACT

This invention relates to alkyl sulfones which are useful as herbicides and plant growth regulants.

3 Claims, No Drawings

ALKYL SULFONES

RELATED APPLICATIONS

This application is a continuation-in-part of my copending application U.S. Ser. No. 227,886, filed Jan. 28, 1981, now abandoned, which is a continuation-in-part of my copending application U.S. Ser. No. 134,287, filed Mar. 26, 1980, now abandoned.

BACKGROUND OF THE INVENTION

This invention relates to novel alkyl sulfones. The compounds of this invention and their agriculturally suitable salts, are useful as agricultural chemicals, e.g. plant growth regulants and herbicides.

Netherlands Pat. No. 121,788, published Sept. 15, 1966, discloses the preparation of compounds of the following Formula and their use as general or selective herbicides:

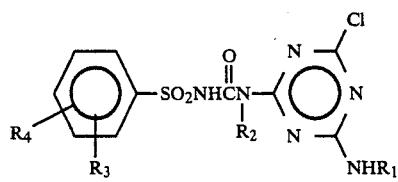

wherein
$R_1$ and $R_2$ may independently be alkyl of 1–4 carbon atoms; and
$R_3$ and $R_4$ may independently be hydrogen, chlorine or alkyl of 1–4 carbon atoms.

U.S. Pat. No. 3,637,366 discloses compounds having the formula:

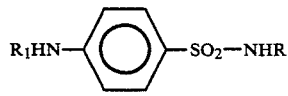

wherein
$R_1$ is hydrogen or lower saturated aliphatic acyl and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

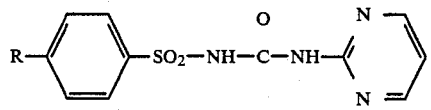

wherein R=H, halogen, $CF_3$ or alkyl.

Logemann et al., Chem. Ab., 53, 18052 g (1959), disclose a number of sulfonamides, including uracil derivatives and those having the formula:

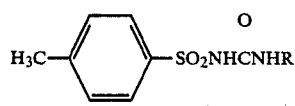

wherein
R is butyl, phenyl or

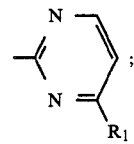

and
$R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

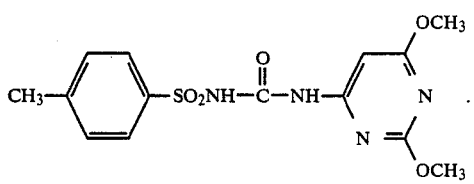

U.S. Pat. No. 4,127,405 teaches compounds which are useful for controlling weeds in wheat having the formula

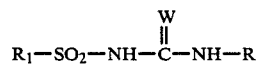

wherein
R is

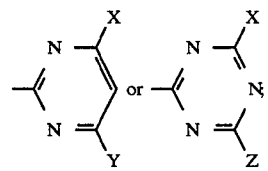

$R_1$ is

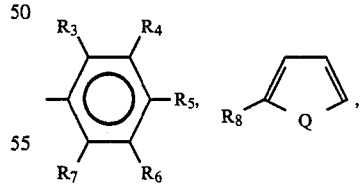

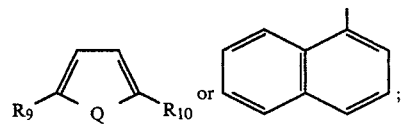

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;
$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention pertains to novel compounds of Formula I, agriculturally suitable compositions containing them and their method-of-use as general or selective pre-emergent or post-emergent herbicides or plant growth regulants

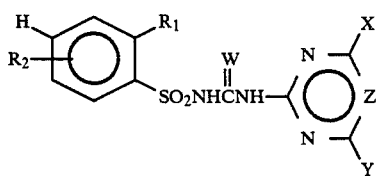

I where $R_1$ is $R_3S(O)_n$;

$R_2$ is H, F, Cl, Br, $CH_3$, $OCH_3$, $CF_3$, $NO_2$, CN or $NH_2$;

$R_3$ is $C_3$–$C_4$ alkyl, $C_3$–$C_4$ alkenyl or cyclopropylmethyl;

n is 0, 1 or 2;

W is O or S;

Z is CH or N;

X is $CH_3$, $C_2H_5$, $CH_3O$, $C_2H_5O$ or $CH_2OCH_3$; and

Y is $CH_3$ or $CH_3O$;

and their agriculturally suitable salts; provided that (1) when $R_2$ is CN, then $R_2$ is not meta to $R_1$; and (2) when W is S, then n is 0 or 2.

Preferred for reasons of their higher herbicidal activity, greater plant growth regulant activity or more favorable ease of synthesis are:

(1) Compounds of Formula I where W is 0.

(2) Compounds of Preferred 1 and where n is 2.

(3) Compounds of Preferred 2 where $R_2$ is H, Cl, $CH_3$, $OCH_3$ or $CF_3$.

(4) Compounds of Preferred 3 where X is $CH_3$ or $OCH_3$.

(5) Compounds of Preferred 4 where $R_2$ is H.

(6) Compounds of Preferred 5 where $R_3$ is $C_3$ alkyl.

Specifically Preferred for reasons of their highest herbicidal activity, treatest plant growth regulant activity or most favorable ease of synthesis are:

N-[(4,6-dimethylpyrimidin2-yl)aminocarbonyl]-2-[(1-methylethyl)sulfonyl]benzenesulfonamide;

N-[(4-methoxy-6-methylpyrimidin-2-yl)aminocarbonyl]-2-[(1-methylethyl)sulfonyl]benzensulfonamide;

N-[(4,6-dimethoxypyrimidin2-yl)aminocarbonyl]-2-[(1-methylethyl)sulfonyl]benzenesulfonamide;

N-[(4,6-dimethyl-1,3,5-triazin-2-yl)aminocarbonyl]-2-[(1-methylethyl)sulfonyl]benzenesulfonamide;

N-[(4-methoxy-6-methyl-1,3,5-triazin-2-yl)aminocarbonyl]-2-[(1-methylethyl)sulfonyl]benzenesulfonamide;

N-[(4,6-dimethoxy-1,3,5-triazin-2-yl)aminocarbonyl]-2-[(1-methylethyl)sulfonyl]benzenesulfonamide;

N-[(4,6-dimethylpyrimidin2-yl)aminocarbonyl]-2-(propylsulfonyl)benzenesulfonamide;

N-[(4-methoxy-6-methylpyrimidin-2-yl)aminocarbonyl]-2-(propylsulfonyl)benzenesulfonamide;

N-[(4,6-dimethoxypyrimidin-2-yl)aminocarbonyl]-2-(propylsulfonyl)benzenesulfonamide;

N-[(4,6-dimethyl-1,3,5-triazin-2-yl)aminocarbonyl]-2-(propylsulfonyl)benzenesulfonamide;

N-[(4-methoxy-6-methyl-1,3,5-triazin-2-yl)aminocarbonyl]-2-(propylsulfonyl)benzenesulfonamide; and N-[(4,6-dimethoxy-1,3,5-triazin-2-yl)aminocarbonyl]-2-(propylsulfonyl)benzenesulfonamide.

This invention also relates to novel compounds of Formula II which are useful as intermediates for the synthesis of herbicidal sulfonylureas.

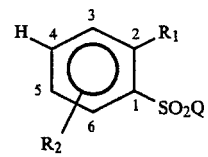

II wherein $R_1$ is $S(O)_nR_3$;

$R_3$ is $C_3$–$C_4$ alkyl, $C_3$–$C_4$ alkenyl orcyclopropylmethyl;

$R_2$ is H, F, Cl, Br, $CH_3$, $OCH_3$ $CF_3$, $NO_2$ or CN;

n is 0 or 2;

Q is $NH_2$ or NCW'; and

W' is O or S;

provided that when $R_2$ is CN, then $R_2$ may only be bonded to the 3 or 5 position of the benzene ring.

Preferred for their utility as intermediates for the preparation of herbicidal compounds with high activity and/or favorable ease of synthesis are:

(1) Compounds of Formula II where Q is NCW'.

(2) Compounds of Preferred 1 where W' is O.

(3) Compounds of Preferred 2 where n is 2.

(4) Compounds of Preferred 3 where $R_3$ is $C_3$–$C_4$ alkyl.

(5) Compounds of Preferred 4 where $R_2$ is H, Cl, $CH_3$, $OCH_3$ or $CF_3$.

(6) Compounds of Preferred 5 where $R_2$ is H.

(7) Compounds of Preferred 6 where $R_3$ is $C_3$ alkyl.
(8) Compounds of Formula II where Q is $NH_2$.
(9) Compounds of Preferred 8 where n is 2.
(10) Compounds of Preferred 9 where $R_3$ is $C_3-C_4$ alkyl.
(11) Compounds of Preferred 10 where $R_2$ is H, Cl, $CH_3$, $OCH_3$ or $CF_3$.
(12) Compounds of Preferred 11 where $R_2$ is H.
(13) Compounds of Preferred 12 where $R_3$ is $C_3$ alkyl.

Specifically Preferred for their utility as intermediates for the preparation of herbicidal compounds with higher activity and/or more favorable ease of synthesis are:
2-(propylsulfonyl)benzenesulfonylisocyanate;
2-(propylthio)benzenesulfonylisocyanate;
2-(1-methylethylsulfonyl)benzenesulfonylisocyanate;
2-(1-methylethylthio)benzenesulfonylisocyanate;
2-(propylsulfonyl)benzenesulfonamide;
2-(propylthio)benzenesulfonamide;
2-(1-methylethylsulfonyl)benzenesulfonamide;
2-(1-methylethylthio)benzenesulfonamide;
2-(propylsulfonyl)benzenesulfonylisothiocyanate;
2-(propylthio)benzenesulfonylisothiocyanate;
2-(1-methylethylsulfonyl)benzenesulfonylisothiocyanate; and
2-(1-methylethylthio)benzenesulfonylisothiocyanate.

SYNTHESIS

As shown in Equation 1, the compounds of Formula I can be prepared by reacting an appropriate 2-aminopyrimidine or 2-amino-1,3,5-triazine of Formula III with an appropriately substituted sulfonyl isocyanate or isothiocyanate of Formula IIa; $R_1$ is $R_3SO_2$ or $R_3S$; $R_2$, $R_3$, X, Y, Z and W are as previously defined.

Equation 1

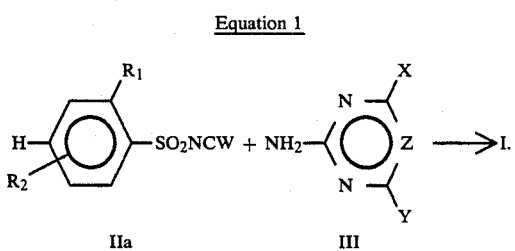

IIa　　　　III

The reaction is best carried out in an inert aprotic organic solvent such as methylene chloride, tetrahydrofuran or acetonitrile, at ambient pressure and temperature. The mode of addition is not critical; however, it is often convenient to add the sulfonyl isocyanate or isothiocyanate to a stirred suspension of amine III. Since such isocyanates and isothiocyanates are usually liquid, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether and filtration.

The intermediate sulfonyl isocyanate of Formula IIa can be prepared by reacting corresponding sulfonamides with phosgene in the presence of n-butyl isocyanate at reflux in a solvent such as xylene, according to the procedure of H. Ulrich and A. A. Y. Sayigh, *Newer Methods of Preparative Organic Chemistry*, Vol. VI, p. 223-241, Academic Press, New York and London, W. Foerst Ed. In cases where formation of the desired sulfonyl isocyanate is difficult by the above procedure, the sulfonylurea formed by the reaction of butyl isocyanate with the appropriate sulfonamide is treated with phosgene according to the above reference.

Some of the sulfonyl isocyanates used in this invention as intermediates are novel. These intermediates are prepared from the parent sulfonamides of Formula IIb as shown in Equation 2 by the reaction of the n-butylsulfonylurea with phosgene as described above. In Equation 2, $R_1$ is $R_3SO_2$ or $R_3S$ and $R_2$ and $R_3$ are as previously defined.

Equation 2

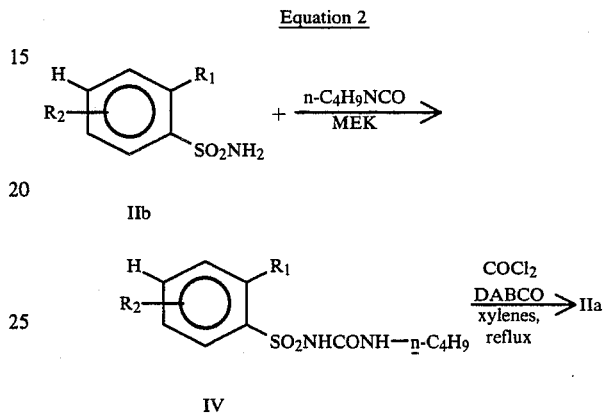

A mixture of the appropriate sulfonylurea, IV and a catalytic amount of 1,4-diaza[2.2.2]bicyclooctane (DABCO) in xylene, chlorobenzene or other inert solvent of sufficiently high boiling point (e.g. 135° C.) is heated to approximately 135° C. Phosgene is added to the mixture until an excess of phosgene is present as indicated by a drop in the boiling point. The mixture is heated further to drive off the excess phosgene, cooled and filtered to remove a small amount of insoluble byproducts. The solvent and alkylisocyanate are removed in vacuo leaving a residue which is the crude sulfonylisocyanate IIa.

The sulfonylisocyanates of Formula IIa may also be prepared by reacting the appropriate sulfonamides of Formula IIb with thionyl chloride and then phosgene as taught in EPO Publication No. 35893.

Certain compounds of Formula I are best prepared by heating a mixture of the arylsulfonylphenylcarbamate of Formula IIc and an appropriate 2-aminopyrimidine or 2-amino-1,3,5-triazine of Formula III in a solvent of sufficiently high boiling point, for example dioxane, as shown in Equation 3. The carbamates of Formula IIc are readily prepared from the corresponding sulfonamides of Formula IIb and diphenylcarbamate in the presence of base.

Equation 3

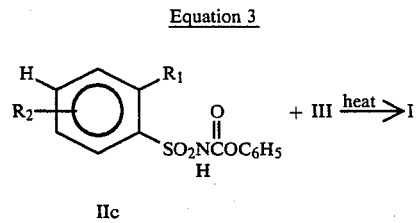

IIc

The compounds of Formula I can also be prepared from the sulfonamides of Formula IIb and the appropriate heterocyclic carbamate of Formula IIIa as shown in Equation 4. Contacting IIb with trimethylaluminum is followed by addition of IIIa. Heating the resulting mixture in dichloromethane will give I after acidic workup. The heterocyclic carbamates of Formula IIIa can be readily prepared from the corresponding amines III by standard literature procedures.

1977, pp. 232-233; Reid, "Organic Chemistry of Bivalent Sulfur," Chemical Publishing Co., New York, Vol. 2, pp. 16-21, 24-29; Vol. 3, pp. 11-14; Peach, in Patai, "The Chemistry of the Thiol Group," pt. 2, pp. 735-744, John Wiley and Sons, Inc., New York, 1974).

Equation 4

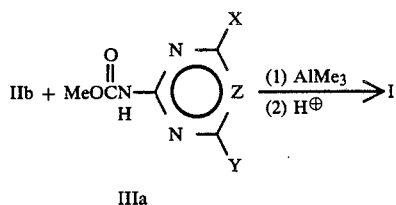

IIIa

Sulfonylisothiocyanates can be prepared by treatment of sulfonamides with carbon disulfide and potassium hydroxide followed by reaction of the dipotassium salt with phosgene according to the teaching of K. Hartke, *Arch. Pharm.*, 229, 174 (1966).

The sulfonamides of Formula IIb wherein n=1 can be prepared by a variety of procedures reported in the literature. As shown in Equation 5, the thioether of Formula VI may be prepared from the appropriate 2-aminothiophenol V and an alkyl halide as described in the literature, e.g., R. N. Prasad et al., *Can. J. Chem.*, 44, 1247 (1966). The formation of the benzenesulfonyl chloride and the corresponding sulfonamide IId has been previously described (co-pending application U.S. Ser. No. 192,034, filed Sept. 29, 1980). The oxidation of IId to the corresponding 2-alkylsulfonylbenzenesulfonamides of Formula IIe may be carried out utilizing a variety of standard literature procedures, including m-chloroperbenzoic acid (C. R. Johnson, et al., *Tetradedron* 25, 5649 (1969)), or with aqueous hydrogen peroxide in acetic acid (F. G. Bordwell, et al., *J. Amer. Chem. Soc.*, 77, 1141 (1955)).

Equation 5

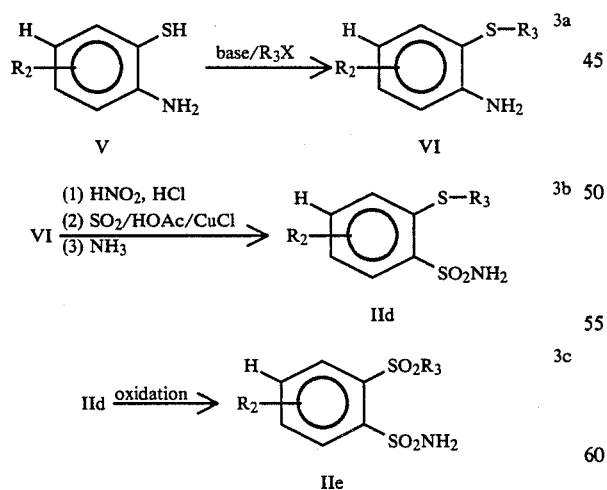

Compounds of Formula IIb wherein n≠1 may also be prepared from 2-halonitrobenzenes of Formula VII as outlined in Equation 6. Halide displacement in VII by thiols (n=0) or sulfinates (n=2) is widely reported in the literature (for general reviews see, "Organic Chemistry of Sulfur", S. Oae, ed., Plenum Press, New York, Equation 6

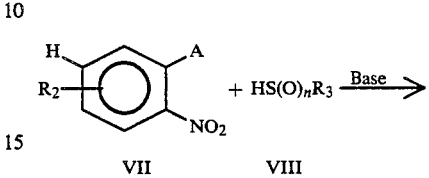

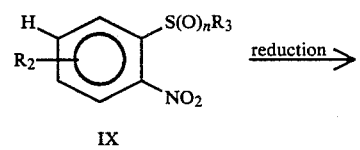

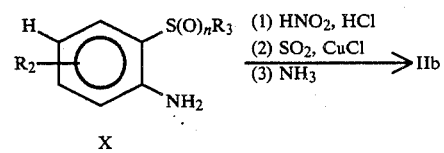

Compounds of Formula IX (n=0 or 2) may also be prepared as shown in Equation 7 (in addition to references cited above, see, *Zh Obshch. Khim*, 35 (8) 1361 (1965) and *J. Chem. Soc.*, 763 (1946)). Reduction of IX to the amine X can be carried out by a variety of standard literature procedures, including catalytic hydrogenation (Rylander, "Catalytic Hydrogenation over Platinum Metals," pp. 168-202, Academic Press, Inc., New York, 1967) and reduction with iron (D. Cowsley et al., *Synthesis* 118 (1977)) or stannous chloride (*Org. Synth., Coll. Vol.* 2, 130 (1943); ibid, 3, 240, 453 (1955)) in acidic medium. Conversion of X to IIb has been discussed previously (Equation 5).

Equation 7

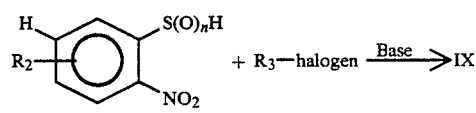

In some cases it is best to oxidize the thioethers of Formula IXa to the corresponding sulfones IXb prior to reduction and subsequent diazotization, as shown in Equation 8.

Equation 8

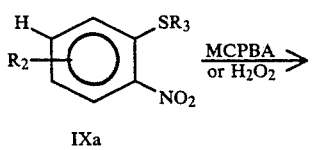

-continued
Equation 8

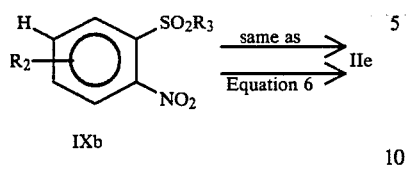

IXb

Ortho-lithiation of appropriately substituted benzene derivatives also provides a route to sulfonamides of Formula IIb. As shown in Equation 9, the t-butylbenzenesulfonamides of Formula XI may be ortho-lithiated [for general review, see H. W. Gschwend et al., *Organic Reactions*, 26, 1 (1979)] and then trapped with sulfur, followed by alkyl halide, or disulfide to give sulfonamides of Formula IId [S. Gronowitz et al., *Acta. Chem. Scand.*, 21, 812 (1967) and *Chem. Ber.*, 99, 3215 (1966)]. Treatment of XII with sulfur dioxide, followed by alkyl halide will give sulfonamides of Formula IIe [*JACS*, 74, 5177 (1952)].

Equation 9

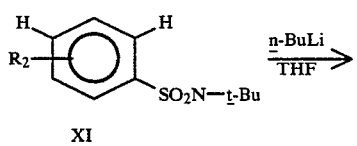

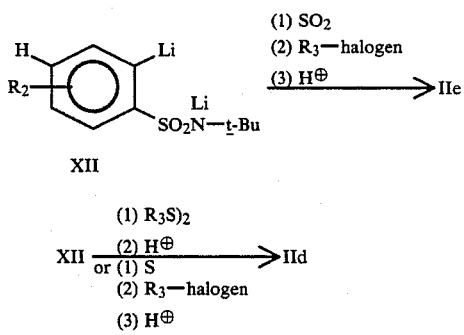

The lithium sulfonates of Formula XIII can also be ortho-lithiated to give compounds of Formula XIV as shown in Equation 10. Treatment of XIV with sulfur electrophiles as in Equation 9 will give the sulfonates of Formula XV (for example, see J. C. Martin et al., *JOC*, 45, 3728 (1980)]. Conversion of XV to the sulfonamides of Formula IIb can be accomplished using thionyl chloride and a catalytic amount of dimethylformamide and then treating the sulfonyl chloride with ammonia.

Equation 10

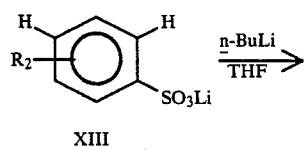

XIII

-continued
Equation 10

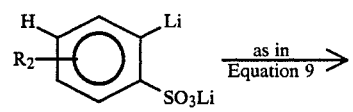

XIV

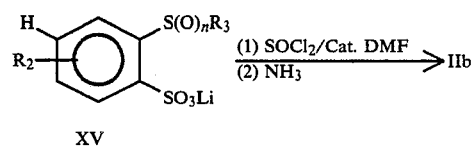

XV

Sulfonamides of Formula IId can also be prepared by reaction of the chlorosulfonamides of Formula IIf and the appropriate mercaptan of Formula XVI in a high boiling solvent, for example, dimethylformamide, as shown in Equation 11. The preparation of the sulfonamides IIf is described in U.S. Pat. No. 4,169,719 and U.S. Pat. No. 4,127,405, which are herein incorporated by reference.

Equation 11

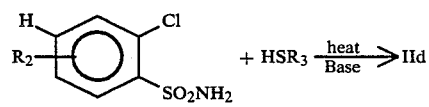

IIf        XVI

Compounds of Formula I may also be prepared by the reaction of the substituted sulfonamides of Formula IIb with an appropriate heterocyclic isocyanate as previously described (co-pending applications U.S. Ser. No. 098,725 and U.S. Ser. No. 098,772).

Compounds of Formula Ib, where $R_1$ is equal to $SOR_3$ can be prepared from the appropriate compounds of Formula Ia where $R_1$ is equal to $SR_3$; $R_2$, X, Y and Z being as previously defined, by oxidation with m-chloroperbenzoic acid according to Equation 12.

Equation 12

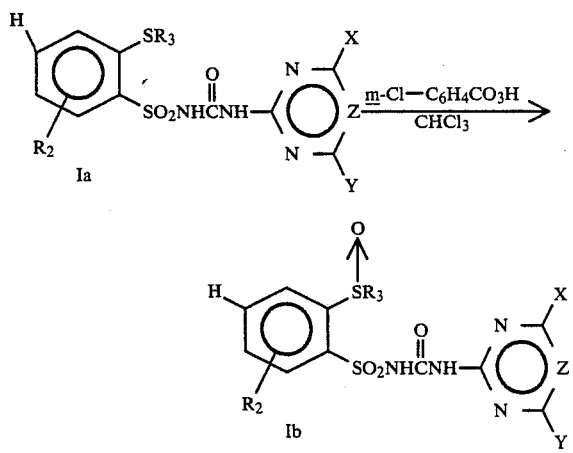

The reaction can be carried out by mixing equivalent amounts of Ia with m-chloroperbenzoic acid in an inert solvent such as chloroform and stirring at 0° C. to reflux for 12–24 hours after which the insoluble m-chlorobenzoic acid produced is removed by filtration and the chloroform solution containing the desired sulfoxide is concentrated to yield the crude product. The product can be purified further by dissolving it in aqueous base of pH 10 and adjusting the pH to 4 to precipitate the desired compound while leaving the m-chlorobenzoic acid in solution as its sodium salt. Treatment of Ia with one equivalent of hydrogen peroxide in glacial acetic acid at 0° C. to room temperature will also give sulfoxide Ib.

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. 2-Amino-1,3,5-triazines can be synthesized according to the methods described by E. M. Smolin and L. Rapaport in "s-Triazines and Derivatives," Vol. XIII of the same series.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

2-(1-Methylethylthio)benzenamine

To a solution of 2-aminothiophenol (90%, 100 g, 0.72 mol) and sodium hydroxide (31.7 g, 0.792 mol) in 90% aqueous ethanol (500 ml) was added dropwise 2-bromopropane (89 g, 0.72 mol) at room temperature. When the addition was complete, the reaction mixture was refluxed for 3 hours, cooled to room temperature, and then concentrated in vacuo. The residue was diluted with water (300 ml) and extracted with ether (3×500 ml). The ether extracts were washed with water and brine, dried with $MgSO_4$ and concentrated in vacuo to yield the crude product. Distillation through a Vigreaux column gave 2-(1-methylethylthio)benzenamine: bp 94° (2.2–2.4 mm).

NMR $(CDCl_3)\delta$: 1.25 (d, 6H, —$CH_3$), 3.15 (hept., 1H, —CH—); 4.25 (broad s, 2H, —$NH_2$); 6.40–7.40 (m, 4H, Ar—H).

EXAMPLE 2

2-(1-Methylethylthio)benzenesulfonamide

To a solution of 2-(1-methylethylthio)benzenamine (200 g, 1.20 mol) in a mixture of concentrated hydrochloric acid (420 ml) and glacial acetic acid (120 ml) was added a solution of sodium nitrile (91.2 g, 1.32 mol) in water (180 ml) at −5° to 0°. The solution was stirred at 0° for ½ hour and then poured, in several portions, into a mixture of cupric chloride dihydrate (24 g) and liquid sulfur dioxide (370 ml, 8.28 mol), in glacial acetic acid (1200 ml) at 0°. The resulting solution was stirred at 0° for one hour and then allowed to warm to room temperature. After several hours, ether (1000 ml) was added, and the reaction mixture was stirred overnight and then poured into ice-water. The resulting oil was extracted into dichloromethane. The organic extracts were washed with water and 5% aqueous sodium bicarbonate (until neutral), dried ($MgSO_4$) and concentrated in vacuo to give an oil. The crude sulfonyl chloride was dissolved in dry THF (2000 ml) and treated with anhydrous liquid ammonia (50 ml, 2.3 mol) at 0°. The solution was stirred at 0° for one hour, allowed to warm to room temperature, and stirred an additional 2.5 hours. The reaction mixture was concentrated in vacuo, and the residue was diluted with water (1000 ml) and extracted with dichloromethane. The extracts were washed with water, dried ($MgSO_4$) and concentrated to yield the crude product. The oil was dissolved in hot (60°) hexane/n-butyl chloride (5/2). Upon cooling, 2-(1-methylethylthio)benzenesulfonamide settled out as a dark oil.

NMR $(CDCl_3)\delta$: 1.30 (d, —$CH_3$); 3.60 (hept. —CH—); 5.75 (broad s, —$NH_2$); 7.0–8.2 (m, Ar—H).

IR (Nujol): 3200–3300 doublet); 1300 and 1150 $cm^{-1}$.

EXAMPLE 3

2-[(1-Methylethyl)sulfonyl]benzenesulfonamide

To a solution of 2-[(1-methylethyl)thio]benzenesulfonamide (79 g, 0.34 mol) in glacial acetic acid (200 ml) was added dropwise 30% aqueous hydrogen peroxide (100 ml, 1.16 mol) at room temperature. When the addition was complete, the reaction mixture was heated to 80° for 2 hours and then allowed to cool to room temperature. Addition of ice-water resulted in the precipitation of 2-[(1-methylethyl)sulfonyl]benzenesulfonamide as a light-yellow solid, m.p. 150°–153°.

NMR $(CDCl_3)\delta$: 1.25 (d, —$CH_3$); 4.20 (hept, —CH—); 6.90 (broad s, —$NH_2$); 7.60–8.40 (m, Ar—H).

IR (KBr) 3400–3300 (d), 1330, 1290, 1160 and 1130 $cm^{-1}$.

EXAMPLE 4

N-[Butylaminocarbonyl]-2-[(1-methylethyl)sulfonyl]-benzenesulfonamide

A mixture of 2-[(1-methylethyl)sulfonyl]benzenesulfonamide (29 g, 0.11 mol), n-butylisocyanate (14.7 g, 0.15 mol) and anhydrous potassium carbonate (16.6 g, 0.120 mol) in methylethyl ketone (325 ml) was refluxed with stirring for 3 hours. The reaction mixture was cooled to 0° and then poured into ice-water. The aqueous solution was acidified to pH 1 with concentrated hydrochloric acid. The resulting precipitate was filtered, washed with water and recrystallized from ethanol to give N-[butylaminocarbonyl]-2-[(1-methylethyl)-sulfonyl]benzenesulfonamide, m.p. 164.5°-165.5°.

NMR (DMSO)δ: 0.6-1.6 (m, 13H, —(CH₂)₂—, —CH₃); 2.7-3.20 (m, 2H, —CH₂—); 4.15 (hept, 1H, —CH—); 6.85 (t, 1H, —NH—); 7.8-8.5 (m, 4.6H, Ar—H, —NH—).

IR (KBr) 3300, 1660, 1430, 1310, 1170 and 1130 cm⁻¹.

EXAMPLE 5

2-[(1-Methylethyl)sulfonyl)benzenesulfonyl isocyanate

A solution of N-[butylaminocarbonyl]-2-[(1-methylethyl)sulfonyl]benzenesulfonamide (17.4 g, 0.048 mol) and 1.4-diaza[2,2,2]bicyclooctane (0.1 g) in mixed xylenes (90 ml) was heated to 135°-140°. Liquid phosgene (3.6 ml, 0.050 mol) was added at a rate to maintain an internal temperature between 125°-135°. When the addition was complete, the solution was refluxed for 2 hours, cooled to room temperature and then filtered under a nitrogen atmosphere. Removal of solvent in vacuo gave 2-[(1-methylethyl)sulfonyl]benzenesulfonyl isocyanate, which was used immediately without further purification.

EXAMPLE 6

N-[(4,6-Dimethylpyrimidin-2-yl)aminocarbonyl]-2-[(1-methylethyl)sulfonyl]benzenesulfonamide A solution of 2-[(1-methylethyl)sulfonyl]benzenesulfonyl isocyanate (2.3 g, 0.008 mol) in dichloromethane (12 ml) was added to 2-amino-4,6-dimethylpyrimidine (0.74 g, 0.006 mol) and DABCO (catalytic amount) and the suspension was stirred overnight at room temperature. The solvent was removed in vacuo and acetonitrile was added to the residue. The precipitated solid was filtered and dried to give N-[(4,6-dimethylpyrimidin-2-yl)aminocarbonyl]-2-[(1-methylethyl)sulfonyl]-benzenesulfonamide as a white powder, m.p. 188°-193° (dec.).

NMR (CDCl₃)δ: 1.30 (d, —C(CH₃)₂); 2.45 (s, het—CH₃); 6.75 (s, het—H).

IR (KBr) 1700, 1600, 1550, 1420, 1330, 1300 1160 and 1130 cm⁻¹.

EXAMPLE 7

2-(1-Propylthio)benzenesulfonamide

To a solution of potassium hydroxide (85%, 12 gm, 0.2 mole) and n-propylmercaptan (18.1 ml, 0.2 mole) in 100 ml dimethylformamide at 90° C. was added a solution of 2-chlorobenzenesulfonamide (19.1 gm, 0.1 mole) in 100 ml dimethylformamide. The reaction mixture was heated to reflux for five hours, cooled, and the solvent was removed in vacuo. The residue was diluted with water, made acidic with concentrated hydrochloric acid and extracted with ether. The ether extracts were washed with water and brine, dried over MgSO₄ and concentrated in vacuo to yield the crude product. Recrystallization from a suitable solvent such as toluene afforded 19 gm (82%) product: m.p. 58°-64°.

NMR (CDCl₃)δ: 1.0 (t, 3H, —CH₃); 1.8 (m, 2H, —CH₂—); 3.1 (t, 2H, —SCH₂); 5.2 (s, 2H, —NH₂); and 7.2-8.0 (m, 4H, —ArH).

EXAMPLE 8

2-(1-Propylsulfonyl)benzenesulfonamide

To a solution of 2-(2-propylthio)benzenesulfonamide (19 gm, 0.082 mole) in glacial acetic acid (50 ml) was added dropwise 30% aqueous hydrogen peroxide (25 ml, 0.3 mole) at room temperature. When the addition was complete, the reaction mixture was heated to 80° C. for 2 hours and then allowed to cool to room temperature. Addition of ice-water resulted in the precipitation of 2-(1-propylsulfonyl)benzenesulfonamide as a light yellow solid, m.p. 122°-124°.

NMR (CDCl₃)δ: 1.0 (t, 3H, —CH₃); 1.7 (m, 2H, —CH₂); 3.4 (t, 2H, —CH₂); 5.2 (s, 2H, NH₂); and 7.5-8.2 (m, 4H, ArH).

EXAMPLE 9

N-[(4,6-Dimethylpyrimidin-2-yl)aminocarbonyl]-2-(1-propylsulfonyl)benzenesulfonamide A solution of 2-(1-propylsulfonyl)benzenesulfonamide (10 gm, 0.04 mole) in 80 ml thionyl chloride was heated to reflux for 6-16 hours. The reaction progress was monitored by NMR and shown to be complete by the disappearance of SO₂NH₂ at 5.2δ. The thionyl chloride was removed in vacuo and to the residue was added 80 ml of a 10% (by weight) solution of phosgene in toluene. Three drops of pyridine were added and the reaction was heated to reflux for 3 hours, cooled, and filtered. The solvent was removed in vacuo to yield the crude sulfonyl isocyanate: IR 2230 cm⁻¹. The sulfonyl isocyanate was dissolved in 50 ml dry acetonitrile and added to a solution of 2-amino-4,6-dimethylpyrimidine (4.3 gm, 0.035 mole) in 50 ml dry acetonitrile. The solution was stirred overnight at room temperature and the precipitated solid was filtered and dried to give N-[(4,6-dimethylpyrimidin-2-yl)aminocarbonyl]-2-(1-propylsulfonyl)benzenesulfonamide as a white powder, m.p, 200°14 202°(dec).

Using procedures similar to those given in Examples 1-9 and Equations 1-12, the following compounds may be prepared.

TABLE I

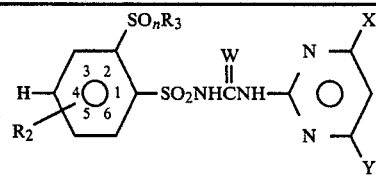

| n | R₂ | R₃ | X | Y | W | m.p. (°C.) |
|---|----|----|---|---|---|-----------|
| 2 | H | —n-C₃H₇ | CH₃ | CH₃ | O | 200-202(D) |
| 2 | H | —n-C₃H₇ | OCH₃ | CH₃ | O | 183-185(D) |
| 2 | H | —n-C₃H₇ | OCH₃ | OCH₃ | O | 215-217 |
| 2 | H | —CH(CH₃)₂ | CH₃ | CH₃ | O | 188-193(D) |
| 2 | H | —CH(CH₃)₂ | OCH₃ | CH₃ | O | 189-192 |

TABLE I-continued

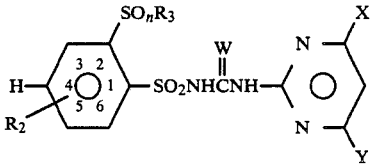

| n | R₂ | R₃ | X | Y | W | m.p. (°C.) |
|---|---|---|---|---|---|---|
| 2 | H | —CH(CH₃)₂ | OCH₃ | OCH₃ | O | 237–239 |
| 2 | H | —n-C₄H₉ | CH₃ | CH₃ | O | 179–181.5(D) |
| 2 | H | —n-C₄H₉ | OCH₃ | CH₃ | O | 152–155 |
| 2 | H | —n-C₄H₉ | OCH₃ | OCH₃ | O | 177–183 |
| 2 | H | CH₂CH(CH₃)₂ | CH₃ | CH₃ | O | 185–191 |
| 2 | H | CH₂CH(CH₃)₂ | OCH₃ | CH₃ | O | 180–185 |
| 2 | H | CH₂CH(CH₃)₂ | OCH₃ | OCH₃ | O | 215–218 |
| 2 | H | CH(CH₃)C₂H₅ | CH₃ | CH₃ | O | 174–178(D) |
| 2 | H | CH(CH₃)C₂H₅ | OCH₃ | CH₃ | O | 198–203 |
| 2 | H | CH(CH₃)C₂H₅ | OCH₃ | OCH₃ | O | 203–213 |
| 2 | H | C(CH₃)₃ | CH₃ | CH₃ | O | 190–195(D) |
| 2 | H | C(CH₃)₃ | OCH₃ | CH₃ | O | 192–195 |
| 2 | H | C(CH₃)₃ | OCH₃ | OCH₃ | O | 217–218 |
| 0 | H | CH₂CH=CH₂ | CH₃ | CH₃ | S | |
| 0 | 5-F | CH=CHC₂H₅ | C₂H₅ | OCH₃ | S | |
| 0 | 3-Cl | CH₂CH₂CH=CH₂ | OC₂H₅ | OCH₃ | S | |
| 0 | 6-Br | CH=CHCH₃ | CH₂OCH₃ | CH₃ | S | |
| 1 | 6-NO₂ | cyclopropyl | C₂H₅ | CH₃ | O | |
| 1 | 5-CN | cyclopropyl | OCH₃ | OCH₃ | O | |
| 1 | 6-NH₂ | cyclopropyl | CH₂OCH₃ | OCH₃ | O | |
| 0 | H | n-C₃H₇ | C₂H₅ | CH₃ | O | |
| 0 | H | n-C₃H₇ | OC₂H₅ | CH₃ | O | |
| 0 | H | n-C₃H₇ | CH₂OCH₃ | CH₃ | O | |
| 0 | H | n-C₃H₇ | C₂H₅ | OCH₃ | O | |
| 0 | H | n-C₃H₇ | OC₂H₅ | OCH₃ | O | |
| 0 | H | n-C₃H₇ | CH₂OCH₃ | OCH₃ | O | |
| 2 | H | n-C₃H₇ | C₂H₅ | CH₃ | O | |
| 2 | H | n-C₃H₇ | OC₂H₅ | CH₃ | O | |
| 2 | H | n-C₃H₇ | CH₂OCH₃ | CH₃ | O | |
| 2 | H | n-C₃H₇ | C₂H₅ | OCH₃ | O | |
| 2 | H | n-C₃H₇ | OC₂H₅ | OCH₃ | O | |
| 2 | H | n-C₃H₇ | CH₂OCH₃ | OCH₃ | O | |
| 2 | H | n-C₃H₇ | CH₃ | CH₃ | S | |
| 2 | H | n-C₃H₇ | CH₃ | OCH₃ | S | |
| 2 | H | n-C₃H₇ | OCH₃ | OCH₃ | S | |
| 0 | H | —CH(CH₃)₂ | C₂H₅ | CH₃ | O | |
| 0 | H | —CH(CH₃)₂ | OC₂H₅ | CH₃ | O | |
| 0 | H | —CH(CH₃)₂ | CH₂OCH₃ | CH₃ | O | |
| 0 | H | —CH(CH₃)₂ | C₂H₅ | OCH₃ | O | |
| 0 | H | —CH(CH₃)₂ | OC₂H₅ | OCH₃ | O | |
| 0 | H | —CH(CH₃)₂ | CH₂OCH₃ | OCH₃ | O | |
| 2 | H | —CH(CH₃)₂ | C₂H₅ | CH₃ | O | |
| 2 | H | —CH(CH₃)₂ | OC₂H₅ | CH₃ | O | |
| 2 | H | —CH(CH₃)₂ | CH₂OCH₃ | CH₃ | O | |
| 2 | H | —CH(CH₃)₂ | C₂H₅ | OCH₃ | O | |
| 2 | H | —CH(CH₃)₂ | OC₂H₅ | OCH₃ | O | |
| 2 | H | —CH(CH₃)₂ | CH₂OCH₃ | OCH₃ | O | |
| 2 | H | —CH(CH₃)₂ | CH₃ | CH₃ | S | |
| 2 | H | —CH(CH₃)₂ | CH₃ | OCH₃ | S | |
| 2 | H | —CH(CH₃)₂ | OCH₃ | OCH₃ | S | |
| 0 | H | n-C₃H₇ | CH₃ | CH₃ | O | 191–200(D) |
| 0 | H | n-C₃H₇ | CH₃ | OCH₃ | O | 160–165 |
| 0 | H | n-C₃H₇ | OCH₃ | OCH₃ | O | 165–170 |
| 1 | H | n-C₃H₇ | CH₃ | CH₃ | O | 110–116 |
| 1 | H | n-C₃H₇ | CH₃ | OCH₃ | O | 80–96 |
| 1 | H | n-C₃H₇ | OCH₃ | OCH₃ | O | 175–178 |

TABLE I-continued

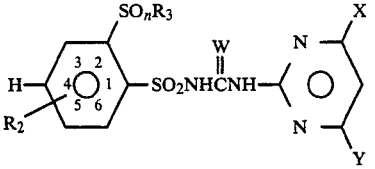

| n | R₂ | R₃ | X | Y | W | m.p. (°C.) |
|---|----|----|---|---|---|-----------|
| 0 | H | —CH(CH₃)₂ | CH₃ | CH₃ | O | |
| 0 | H | —CH(CH₃)₂ | CH₃ | OCH₃ | O | |
| 0 | H | —CH(CH₃)₂ | OCH₃ | OCH₃ | O | |
| 1 | H | —CH(CH₃)₂ | CH₃ | CH₃ | O | |
| 1 | H | —CH(CH₃)₂ | CH₃ | OCH₃ | O | |
| 1 | H | —CH(CH₃)₂ | OCH₃ | OCH₃ | O | |
| 0 | H | —CH₂—CH(CH₂)(CH₂) | CH₃ | CH₃ | O | |
| 0 | H | —CH₂—CH(CH₂)(CH₂) | CH₃ | OCH₃ | O | |
| 0 | H | —CH₂—CH(CH₂)(CH₂) | OCH₃ | OCH₃ | O | |
| 2 | H | —CH₂—CH(CH₂)(CH₂) | CH₃ | CH₃ | O | 198–199° |
| 2 | H | —CH₂—CH(CH₂)(CH₂) | CH₃ | OCH₃ | O | 196–198° |
| 2 | H | —CH₂—CH(CH₂)(CH₂) | OCH₃ | OCH₃ | O | 226–227° |
| 0 | H | —CH₂CH=CH₂ | CH₃ | CH₃ | O | 198–203° |
| 0 | H | —CH₂CH=CH₂ | CH₃ | OCH₃ | O | 175–177° |
| 0 | H | —CH₂CH=CH₂ | OCH₃ | OCH₃ | O | 181–186° |
| 2 | H | —CH₂CH=CH₂ | CH₃ | CH₃ | O | 173–180° |
| 2 | H | —CH₂CH=CH₂ | CH₃ | OCH₃ | O | 185–190° |
| 2 | H | —CH₂CH=CH₂ | OCH₃ | OCH₃ | O | 228–232° |
| 2 | H | —CH(CH₃)CH=CH₂ | CH₃ | CH₃ | O | |
| 2 | H | —CH(CH₃)CH=CH₂ | CH₃ | OCH₃ | O | |
| 2 | H | —CH(CH₃)CH=CH₂ | OCH₃ | OCH₃ | O | |
| 2 | H | —CH₂CH₂CH=CH₂ | CH₃ | CH₃ | O | |
| 2 | H | —CH₂CH₂CH=CH₂ | CH₃ | OCH₃ | O | |
| 2 | H | —CH₂CH₂CH=CH₂ | OCH₃ | OCH₃ | O | |
| 0 | H | n-C₃H₇ | CH₃ | CH₃ | S | |
| 0 | H | n-C₃H₇ | CH₃ | OCH₃ | S | |
| 0 | H | n-C₃H₇ | OCH₃ | OCH₃ | S | |
| 0 | H | CH₂CH=CH₂ | OCH₃ | OCH₃ | S | |
| 2 | H | CH=CHCH₃ | OCH₃ | CH₃ | O | |
| 2 | H | CH=CHCH₂CH₃ | OCH₃ | CH₃ | O | |
| 2 | H | CH₂CH₂CH=CH₂ | OCH₃ | OCH₃ | O | |
| 2 | H | CH₂CH=CHCH₃ | OCH₃ | OCH₃ | O | |
| 2 | 3-F | n-C₃H₇ | CH₃ | OCH₃ | O | |
| 2 | 6-F | n-C₃H₇ | CH₃ | CH₃ | O | |
| 2 | 3-NO₂ | C₃H₇ | OCH₃ | OCH₃ | O | |
| 2 | 5-Cl | n-C₃H₇ | OCH₃ | CH₃ | O | |
| 2 | 6-Cl | n-C₃H₇ | OCH₃ | OCH₃ | O | |
| 2 | 3-Br | n-C₄H₉ | OCH₃ | CH₃ | O | |
| 2 | 5-Br | C₄H₉ | OCH₃ | CH₃ | O | |
| 2 | 3-CH₃ | n-C₃H₇ | CH₃ | OCH₂CH₃ | O | |
| 2 | 5-NO₂ | n-C₃H₇ | CH₃ | OCH₃ | O | |

TABLE I-continued

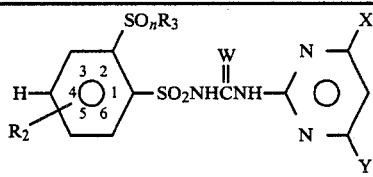

| n | R₂ | R₃ | X | Y | W | m.p. (°C.) |
|---|---|---|---|---|---|---|
| 2 | 5-CH₃ | n-C₃H₇ | OCH₃ | OCH₃ | O | |
| 2 | 6-CH₃ | n-C₃H₇ | OCH₃ | OCH₃ | O | |
| 2 | 3-CF₃ | n-C₃H₇ | OCH₃ | CH₃ | O | |
| 2 | 6-NO₂ | n-C₃H₇ | CH₃ | OCH₃ | O | |
| 2 | 5-CF₃ | n-C₃H₇ | CH₃ | OCH₃ | O | |
| 2 | 6-CF₃ | n-C₃H₇ | CH₃ | CH₃ | O | |
| 2 | 3-CN | n-C₃H₇ | OCH₃ | OCH₃ | O | |
| 2 | 5-CN | n-C₃H₇ | OCH₃ | OCH₃ | O | |
| 2 | H | n-C₃H₇ | C₂H₅ | OCH₃ | O | |
| 2 | H | n-C₃H₇ | C₂H₅ | CH₃ | O | |
| 2 | H | n-C₃H₇ | OC₂H₅ | CH₃ | O | |
| 2 | H | n-C₃H₇ | OC₂H₅ | OCH₃ | O | |
| 2 | H | n-C₃H₇ | CH₂OCH₃ | CH₃ | O | |
| 2 | H | n-C₃H₇ | CH₂OCH₃ | OCH₃ | O | |
| 1 | H | CH₂CH=CH₂ | CH₃ | CH₃ | O | |
| 1 | H | CH₂CH=CH₂ | CH₃ | OCH₃ | O | |
| 1 | H | CH₂CH=CH₂ | OCH₃ | OCH₃ | O | |

TABLE II

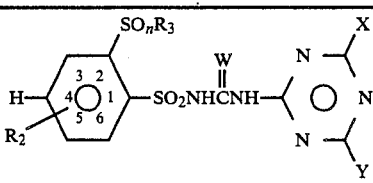

| n | R₂ | R₃ | X | Y | W | m.p. (°C.) |
|---|---|---|---|---|---|---|
| 2 | H | —n-C₃H₇ | CH₃ | CH₃ | O | 189–191°(D) |
| 2 | H | —n-C₃H₇ | OCH₃ | CH₃ | O | 200–201°(D) |
| 2 | H | —n-C₃H₇ | OCH₃ | OCH₃ | O | 184–187° |
| 2 | H | —CH(CH₃)₂ | CH₃ | CH₃ | O | 115–119° |
| 2 | H | —CH(CH₃)₂ | OCH₃ | CH₃ | O | 108–126° |
| 2 | H | —CH(CH₃)₂ | OCH₃ | OCH₃ | O | 108–130° |
| 2 | H | —n-C₄H₉ | CH₃ | CH₃ | O | 173–178° |
| 2 | H | —n-C₄H₉ | OCH₃ | CH₃ | O | 173–177° |
| 2 | H | —n-C₄H₉ | OCH₃ | OCH₃ | O | 175–179° |
| 2 | H | CH₂CH(CH₃)₂ | CH₃ | CH₃ | O | 180–183° |
| 2 | H | CH₂CH(CH₃)₂ | OCH₃ | CH₃ | O | 175–178° |
| 2 | H | CH₂CH(CH₃)₂ | OCH₃ | OCH₃ | O | 180–188° |
| 2 | H | CH(CH₃)C₂H₅ | CH₃ | CH₃ | O | 160–163° |
| 2 | H | CH(CH₃)C₂H₅ | OCH₃ | CH₃ | O | 170–173.5° |
| 2 | H | CH(CH₃)C₂H₅ | OCH₃ | OCH₃ | O | 173–181° |
| 2 | H | C(CH₃)₃ | CH₃ | CH₃ | O | 193–195° |
| 2 | H | C(CH₃)₃ | OCH₃ | CH₃ | O | 175–179° |
| 2 | H | C(CH₃)₃ | OCH₃ | OCH₃ | O | 178–181° |
| 2 | 3-NH₂ | CH₂CH=CH₂ | CH₃ | CH₃ | S | |
| 0 | 6-F | CH=CHC₂H₅ | CH₂OCH₃ | OCH₃ | S | |
| 0 | 3-Br | CH₂CH₂CH=CH₂ | C₂H₅ | CH₃ | S | |
| 0 | 5-Cl | CH₂—CH(CH₂)(CH₂) | CH₂OCH₃ | CH₃ | S | |
| 0 | 6-CH₃ | CH₂—CH(CH₂)(CH₂) | OC₂H₅ | OCH₃ | S | |
| 0 | H | n-C₃H₇ | C₂H₅ | CH₃ | O | |
| 0 | H | n-C₃H₇ | OC₂H₅ | CH₃ | O | |
| 0 | H | n-C₃H₇ | CH₂OCH₃ | CH₃ | O | |
| 0 | H | n-C₃H₇ | C₂H₅ | OCH₃ | O | |
| 0 | H | n-C₃H₇ | OC₂H₅ | OCH₃ | O | |
| 0 | H | n-C₃H₇ | CH₂OCH₃ | OCH₃ | O | |

TABLE II-continued $$\underset{R_2}{\overset{SO_nR_3}{\text{structure}}} - SO_2NHCNH - \underset{N}{\overset{W}{\text{structure}}} - \underset{Y}{\overset{X}{\text{structure}}}$$

| n | R₂ | R₃ | X | Y | W | m.p. (°C.) |
|---|---|---|---|---|---|---|
| 2 | H | n-C₃H₇ | C₂H₅ | CH₃ | O | |
| 2 | H | n-C₃H₇ | OC₂H₅ | CH₃ | O | |
| 2 | H | n-C₃H₇ | CH₂OCH₃ | CH₃ | O | |
| 2 | H | n-C₃H₇ | C₂H₅ | OCH₃ | O | |
| 2 | H | n-C₃H₇ | OC₂H₅ | OCH₃ | O | |
| 2 | H | n-C₃H₇ | CH₂OCH₃ | OCH₃ | O | |
| 2 | H | n-C₃H₇ | CH₃ | CH₃ | S | |
| 2 | H | n-C₃H₇ | CH₃ | OCH₃ | S | |
| 2 | H | n-C₃H₇ | OCH₃ | OCH₃ | S | |
| 0 | H | —CH(CH₃)₂ | C₂H₅ | CH₃ | O | |
| 0 | H | —CH(CH₃)₂ | OC₂H₅ | CH₃ | O | |
| 0 | H | —CH(CH₃)₂ | CH₂OCH₃ | CH₃ | O | |
| 0 | H | —CH(CH₃)₂ | C₂H₅ | OCH₃ | O | |
| 0 | H | —CH(CH₃)₂ | OC₂H₅ | OCH₃ | O | |
| 0 | H | —CH(CH₃)₂ | CH₂OCH₃ | OCH₃ | O | |
| 2 | H | —CH(CH₃)₂ | C₂H₅ | CH₃ | O | |
| 2 | H | —CH(CH₃)₂ | OC₂H₅ | CH₃ | O | |
| 2 | H | —CH(CH₃)₂ | CH₂OCH₃ | CH₃ | O | |
| 2 | H | —CH(CH₃)₂ | C₂H₅ | OCH₃ | O | |
| 2 | H | —CH(CH₃)₂ | OCH₂H₅ | OCH₃ | O | |
| 2 | H | —CH(CH₃)₂ | CH₂OCH₃ | OCH₃ | O | |
| 2 | H | —CH(CH₃)₂ | CH₃ | CH₃ | S | |
| 2 | H | —CH(CH₃)₂ | CH₃ | OCH₃ | S | |
| 2 | H | —CH(CH₃)₂ | OCH₃ | OCH₃ | S | |
| 0 | H | n-C₃H₇ | CH₃ | CH₃ | O | 150–157° |
| 0 | H | n-C₃H₇ | CH₃ | OCH₃ | O | 128–135° |
| 0 | H | n-C₃H₇ | OCH₃ | OCH₃ | O | 152–155° |
| 1 | H | n-C₃H₇ | CH₃ | CH₃ | O | 163–166° |
| 1 | H | n-C₃H₇ | CH₃ | OCH₃ | O | 75–95° |
| 1 | H | n-C₃H₇ | OCH₃ | OCH₃ | O | 122–125° |
| 0 | H | —CH(CH₃)₂ | CH₃ | CH₃ | O | |
| 0 | H | —CH(CH₃)₂ | CH₃ | OCH₃ | O | |
| 0 | H | —CH(CH₃)₂ | OCH₃ | OCH₃ | O | |
| 1 | H | —CH(CH₃)₂ | CH₃ | CH₃ | O | |
| 1 | H | —CH(CH₃)₂ | CH₃ | OCH₃ | O | |
| 1 | H | —CH(CH₃)₂ | OCH₃ | OCH₃ | O | |
| 0 | H | —CH₂—CH(CH₂)(CH₂) (cyclopropyl) | CH₃ | CH₃ | O | |
| 0 | H | —CH₂—CH(CH₂)(CH₂) (cyclopropyl) | CH₃ | OCH₃ | O | |
| 0 | H | —CH₂—CH(CH₂)(CH₂) (cyclopropyl) | OCH₃ | OCH₃ | O | |
| 2 | H | —CH₂—CH(CH₂)(CH₂) (cyclopropyl) | CH₃ | CH₃ | O | 138–140° |
| 2 | H | —CH₂—CH(CH₂)(CH₂) (cyclopropyl) | CH₃ | OCH₃ | O | 188–190° |
| 2 | H | —CH₂—CH(CH₂)(CH₂) (cyclopropyl) | OCH₃ | OCH₃ | O | 211–212° |

TABLE II-continued

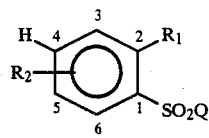

| n | R₂ | R₃ | X | Y | W | m.p. (°C.) |
|---|---|---|---|---|---|---|
| 0 | H | —CH₂CH=CH₂ | CH₃ | CH₃ | O | 150–158° |
| 0 | H | —CH₂CH=CH₂ | CH₃ | OCH₃ | O | 130–135° |
| 0 | H | —CH₂CH=CH₂ | OCH₃ | OCH₃ | O | 125–130° |
| 2 | H | —CH₂CH=CH₂ | CH₃ | CH₃ | O | 185–190° |
| 2 | H | —CH₂CH=CH₂ | CH₃ | OCH₃ | O | 188–190° |
| 2 | H | —CH₂CH=CH₂ | OCH₃ | OCH₃ | O | 187–190° |
| 2 | H | —CH(CH₃)CH=CH₂ | CH₃ | CH₃ | O | |
| 2 | H | —CH(CH₃)CH=CH₂ | CH₃ | OCH₃ | O | |
| 2 | H | —CH(CH₃)CH=CH₂ | OCH₃ | OCH₃ | O | |
| 2 | H | —CH₂CH₂CH=CH₂ | CH₃ | CH₃ | O | |
| 2 | H | —CH₂CH₂CH=CH₂ | CH₃ | OCH₃ | O | |
| 2 | H | —CH₂CH₂CH=CH₂ | OCH₃ | OCH₃ | O | |
| 0 | H | n-C₃H₇ | CH₃ | CH₃ | S | |
| 0 | H | n-C₃H₇ | CH₃ | OCH₃ | S | |
| 0 | H | n-C₃H₇ | OCH₃ | OCH₃ | S | |
| 0 | H | CH₂CH=CH₂ | OCH₃ | OCH₃ | S | |
| 2 | H | CH=CHCH₃ | CH₃ | OCH₃ | O | |
| 2 | H | CH=CHCH₂CH₃ | CH₃ | OCH₃ | O | |
| 2 | H | CH₂CH₂CH=CH₂ | OCH₃ | OCH₃ | O | |
| 2 | H | CH₂CH=CHCH₃ | OCH₃ | CH₃ | O | |
| 2 | 3-F | n-C₃H₇ | CH₃ | OCH₃ | O | |
| 2 | 6-F | n-C₃H₇ | CH₃ | CH₃ | O | |
| 2 | 3-NO₂ | n-C₃H₇ | OCH₃ | OCH₃ | O | |
| 2 | 5-Cl | n-C₃H₇ | OCH₃ | CH₃ | O | |
| 2 | 6-Cl | n-C₃H₇ | OCH₃ | OCH₃ | O | |
| 2 | 3-Br | n-C₄H₉ | OCH₃ | CH₃ | O | |
| 2 | 5-Br | n-C₄H₉ | OCH₃ | CH₃ | O | |
| 2 | 3-CH₃ | n-C₃H₇ | CH₃ | OCH₂CH₃ | O | |
| 2 | 5-NO₂ | n-C₃H₇ | CH₃ | OCH₃ | O | |
| 2 | 5-CH₃ | n-C₃H₇ | OCH₃ | OCH₃ | O | |
| 2 | 6-CH₃ | n-C₃H₇ | OCH₃ | OCH₃ | O | |
| 2 | 3-CF₃ | n-C₃H₇ | OCH₃ | CH₃ | O | |
| 2 | 6-NO₂ | n-C₃H₇ | CH₃ | OCH₃ | O | |
| 2 | 5-CF₃ | n-C₃H₇ | CH₃ | OCH₃ | O | |
| 2 | 6-CF₃ | n-C₃H₇ | CH₃ | CH₃ | O | |
| 2 | 3-CN | n-C₃H₇ | OCH₃ | OCH₃ | O | |
| 2 | 5-CN | n-C₃H₇ | OCH₃ | OCH₃ | O | |
| 2 | H | n-C₃H₇ | C₂H₅ | OCH₃ | O | |
| 2 | H | n-C₃H₇ | C₂H₅ | CH₃ | O | |
| 2 | H | n-C₃H₇ | OC₂H₅ | CH₃ | O | |
| 2 | H | n-C₃H₇ | OC₂H₅ | OCH₃ | O | |
| 2 | H | n-C₃H₇ | CH₂OCH₃ | CH₃ | O | |
| 2 | H | n-C₃H₇ | CH₂OCH₃ | OCH₃ | O | |
| 1 | H | CH₂CH=CH₂ | CH₃ | CH₃ | O | |
| 1 | H | CH₂CH=CH₂ | CH₃ | OCH₃ | O | |
| 1 | H | CH₂CH=CH₂ | OCH₃ | OCH₃ | O | |

TABLE III

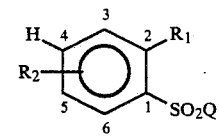

| R₁ | R₂ | Q | m.p. (°C.) |
|---|---|---|---|
| SCH₂CH₂CH₃ | H | NH₂ | 58–64° |
| SCH₂CH₂CH₃ | 3-Cl | NH₂ | |
| SCH₂CH₂CH₃ | 5-Cl | NH₂ | |
| SCH₂CH₂CH₃ | 6-Cl | NH₂ | |
| SCH₂CH₂CH₃ | 3-CH₃ | NH₂ | |
| SCH₂CH₂CH₃ | 5-CH₃ | NH₂ | |
| SCH₂CH₂CH₃ | 6-CH₃ | NH₂ | |
| SCH₂CH₂CH₃ | 3-OCH₃ | NH₂ | |
| SCH₂CH₂CH₃ | 5-OCH₃ | NH₂ | |
| SCH₂CH₂CH₃ | 6-OCH₃ | NH₂ | |
| SCH₂CH₂CH₃ | 3-CF₃ | NH₂ | |
| SCH₂CH₂CH₃ | 5-CF₃ | NH₂ | |
| SCH₂CH₂CH₃ | 6-CF₃ | NH₂ | |
| SCH₂CH₂CH₃ | 5-F | NH₂ | |
| SCH₂CH₂CH₃ | 5-Br | NH₂ | |
| SCH₂CH₂CH₃ | 5-NO₂ | NH₂ | |
| SCH₂CH₂CH₃ | 5-CN | NH₂ | |
| SO₂CH₂CH₂CH₃ | H | NH₂ | 122–124° |
| SO₂CH₂CH₂CH₃ | 3-Cl | NH₂ | |
| SO₂CH₂CH₂CH₃ | 5-Cl | NH₂ | |
| SO₂CH₂CH₂CH₃ | 6-Cl | NH₂ | |
| SO₂CH₂CH₂CH₃ | 3-CH₃ | NH₂ | |
| SO₂CH₂CH₂CH₃ | 5-CH₃ | NH₂ | |
| SO₂CH₂CH₂CH₃ | 6-CH₃ | NH₂ | |

TABLE III-continued

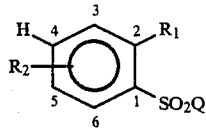

| R₁ | R₂ | Q | m.p. (°C.) |
|---|---|---|---|
| SO₂CH₂CH₂CH₃ | 3-OCH₃ | NH₂ | |
| SO₂CH₂CH₂CH₃ | 5-OCH₃ | NH₂ | |
| SO₂CH₂CH₂CH₃ | 6-OCH₃ | NH₂ | |
| SO₂CH₂CH₂CH₃ | 3-CF₃ | NH₂ | |
| SO₂CH₂CH₂CH₃ | 5-CF₃ | NH₂ | |
| SO₂CH₂CH₂CH₃ | 6-CF₃ | NH₂ | |
| SO₂CH₂CH₂CH₃ | 5-F | NH₂ | |
| SO₂CH₂CH₂CH₃ | 5-Br | NH₂ | |
| SO₂CH₂CH₂CH₃ | 5-NO₂ | NH₂ | |
| SO₂CH₂CH₂CH₃ | 5-CN | NH₂ | |
| SCH(CH₃)₂ | H | NH₂ | oil (IR: 3200 and 3300 cm⁻¹) |
| SCH(CH₃)₂ | 3-Cl | NH₂ | |
| SCH(CH₃)₂ | 5-Cl | NH₂ | |
| SCH(CH₃)₂ | 6-Cl | NH₂ | |
| SCH(CH₃)₂ | 3-CH₃ | NH₂ | |
| SCH(CH₃)₂ | 5-CH₃ | NH₂ | |
| SCH(CH₃)₂ | 6-CH₃ | NH₂ | |
| SCH(CH₃)₂ | 3-OCH₃ | NH₂ | |
| SCH(CH₃)₂ | 5-OCH₃ | NH₂ | |
| SCH(CH₃)₂ | 6-OCH₃ | NH₂ | |
| SCH(CH₃)₂ | 3-CF₃ | NH₂ | |
| SCH(CH₃)₂ | 5-CF₃ | NH₂ | |
| SCH(CH₃)₂ | 6-CF₃ | NH₂ | |
| SCH(CH₃)₂ | 5-F | NH₂ | |
| SCH(CH₃)₂ | 5-Br | NH₂ | |
| SCH(CH₃)₂ | 5-NO₂ | NH₂ | |
| SCH(CH₃)₂ | 5-CN | NH₂ | |
| SO₂CH(CH₃)₂ | H | NH₂ | 149–153° |
| SO₂CH(CH₃)₂ | 3-Cl | NH₂ | |
| SO₂CH(CH₃)₂ | 5-Cl | NH₂ | |
| SO₂CH(CH₃)₂ | 6-Cl | NH₂ | |
| SO₂CH(CH₃)₂ | 3-CH₃ | NH₂ | |
| SO₂CH(CH₃)₂ | 5-CH₃ | NH₂ | |
| SO₂CH(CH₃)₂ | 6-CH₃ | NH₂ | |
| SO₂CH(CH₃)₂ | 3-OCH₃ | NH₂ | |
| SO₂CH(CH₃)₂ | 5-OCH₃ | NH₂ | |
| SO₂CH(CH₃)₂ | 6-OCH₃ | NH₂ | |
| SO₂CH(CH₃)₂ | 3-CF₃ | NH₂ | |
| SO₂CH(CH₃)₂ | 5-CF₃ | NH₂ | |
| SO₂CH(CH₃)₂ | 6-CF₃ | NH₂ | |
| SO₂CH(CH₃)₂ | 5-F | NH₂ | |
| SO₂CH(CH₃)₂ | 5-Br | NH₂ | |
| SO₂CH(CH₃)₂ | 5-NO₂ | NH₂ | |
| SO₂CH(CH₃)₂ | 5-CN | NH₂ | |
| SCH₂CH₂CH₂CH₃ | H | NH₂ | 65–70° |
| SCH₂CH₂CH₂CH₃ | 3-Cl | NH₂ | |
| SCH₂CH₂CH₂CH₃ | 5-Cl | NH₂ | |
| SCH₂CH₂CH₂CH₃ | 6-Cl | NH₂ | |
| SCH₂CH₂CH₂CH₃ | 3-CH₃CH | NH₂ | |
| SCH₂CH₂CH₂CH₃ | 5-CH₃ | NH₂ | |
| SCH₂CH₂CH₂CH₃ | 6-CH₃ | NH₂ | |
| SCH₂CH₂CH₂CH₃ | 3-OCH₃ | NH₂ | |
| SCH₂CH₂CH₂CH₃ | 5-OCH₃ | NH₂ | |
| SCH₂CH₂CH₂CH₃ | 6-OCH₃ | NH₂ | |
| SCH₂CH₂CH₂CH₃ | 3-CF₃ | NH₂ | |
| SCH₂CH₂CH₂CH₃ | 5-CF₃ | NH₂ | |
| SCH₂CH₂CH₂CH₃ | 6-CF₃ | NH₂ | |
| SCH₂CH₂CH₂CH₃ | 5-F | NH₂ | |
| SCH₂CH₂CH₂CH₃ | 5-Br | NH₂ | |
| SCH₂CH₂CH₂CH₃ | 5-NO₂ | NH₂ | |
| SCH₂CH₂CH₂CH₃ | 5-CN | NH₂ | |
| SO₂CH₂CH₂CH₂CH₃ | H | NH₂ | 136–138° |
| SO₂CH₂CH₂CH₂CH₃ | 3-Cl | NH₂ | |
| SO₂CH₂CH₂CH₂CH₃ | 5-Cl | NH₂ | |
| SO₂CH₂CH₂CH₂CH₃ | 6-Cl | NH₂ | |
| SO₂CH₂CH₂CH₂CH₃ | 3-CH₃ | NH₂ | |
| SO₂CH₂CH₂CH₂CH₃ | 5-CH₃ | NH₂ | |
| SO₂CH₂CH₂CH₂CH₃ | 6-CH₃ | NH₂ | |
| SO₂CH₂CH₂CH₂CH₃ | 3-OCH₃ | NH₂ | |
| SO₂CH₂CH₂CH₂CH₃ | 5-OCH₃ | NH₂ | |
| SO₂CH₂CH₂CH₂CH₃ | 6-OCH₃ | NH₂ | |
| SO₂CH₂CH₂CH₂CH₃ | 3-CF₃ | NH₂ | |

TABLE III-continued

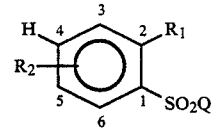

| R₁ | R₂ | Q | m.p. (°C.) |
|---|---|---|---|
| SO₂CH₂CH₂CH₂CH₃ | 5-CF₃ | NH₂ | |
| SO₂CH₂CH₂CH₂CH₃ | 6-CF₃ | NH₂ | |
| SO₂CH₂CH₂CH₂CH₃ | 5-F | NH₂ | |
| SO₂CH₂CH₂CH₂CH₃ | 5-Br | NH₂ | |
| SO₂CH₂CH₂CH₂CH₃ | 5-NO₂ | NH₂ | |
| SO₂CH₂CH₂CH₂CH₃ | 5-CN | NH₂ | |
| SCH₂CH(CH₃)₂ | H | NH₂ | 66–76° |
| SCH₂CH(CH₃)₂ | 3-Cl | NH₂ | |
| SCH₂CH(CH₃)₂ | 5-Cl | NH₂ | |
| SCH₂CH(CH₃)₂ | 6-Cl | NH₂ | |
| SCH₂CH(CH₃)₂ | 3-CH₃ | NH₂ | |
| SCH₂CH(CH₃)₂ | 5-CH₃ | NH₂ | |
| SCH₂CH(CH₃)₂ | 6-CH₃ | NH₂ | |
| SCH₂CH(CH₃)₂ | 3-OCH₃ | NH₂ | |
| SCH₂CH(CH₃)₂ | 5-OCH₃ | NH₂ | |
| SCH₂CH(CH₃)₂ | 6-OCH₃ | NH₂ | |
| SCH₂CH(CH₃)₂ | 3-CF₃ | NH₂ | |
| SCH₂CH(CH₃)₂ | 5-CF₃ | NH₂ | |
| SCH₂CH(CH₃)₂ | 6-CF₃ | NH₂ | |
| SCH₂CH(CH₃)₂ | 5-F | NH₂ | |
| SCH₂CH(CH₃)₂ | 5-Br | NH₂ | |
| SCH₂CH(CH₃)₂ | 5-NO₂ | NH₂ | |
| SCH₂CH(CH₃)₂ | 5-CN | NH₂ | |
| SO₂CH₂CH(CH₃)₂ | H | NH₂ | 125–127° |
| SO₂CH₂CH(CH₃)₂ | 3-Cl | NH₂ | |
| SO₂CH₂CH(CH₃)₂ | 5-Cl | NH₂ | |
| SO₂CH₂CH(CH₃)₂ | 6-Cl | NH₂ | |
| SO₂CH₂CH(CH₃)₂ | 3-CH₃ | NH₂ | |
| SO₂CH₂CH(CH₃)₂ | 5-CH₃ | NH₂ | |
| SO₂CH₂CH(CH₃)₂ | 6-CH₃ | NH₂ | |
| SO₂CH₂CH(CH₃)₂ | 3-OCH₃ | NH₂ | |
| SO₂CH₂CH(CH₃)₂ | 5-OCH₃ | NH₂ | |
| SO₂CH₂CH(CH₃)₂ | 6-OCH₃ | NH₂ | |
| SO₂CH₂CH(CH₃)₂ | 3-CF₃ | NH₂ | |
| SO₂CH₂CH(CH₃)₂ | 5-CF₃ | NH₂ | |
| SO₂CH₂CH(CH₃)₂ | 6-CF₃ | NH₂ | |
| SO₂CH₂CH(CH₃)₂ | 5-F | NH₂ | |
| SO₂CH₂CH(CH₃)₂ | 5-Br | NH₂ | |
| SO₂CH₂CH(CH₃)₂ | 5-NO₂ | NH₂ | |
| SO₂CH₂CH(CH₃)₂ | 5-CN | NH₂ | |
| SCH(CH₃)CH₂CH₃ | H | NH₂ | |
| SCH(CH₃)CH₂CH₃ | 3-Cl | NH₂ | |
| SCH(CH₃)CH₂CH₃ | 5-Cl | NH₂ | |
| SCH(CH₃)CH₂CH₃ | 6-Cl | NH₂ | |
| SCH(CH₃)CH₂CH₃ | 3-CH₃ | NH₂ | |
| SCH(CH₃)CH₂CH₃ | 5-CH₃ | NH₂ | |
| SCH(CH₃)CH₂CH₃ | 6-CH₃ | NH₂ | |
| SCH(CH₃)CH₂CH₃ | 3-OCH₃ | NH₂ | |
| SCH(CH₃)CH₂CH₃ | 5-OCH₃ | NH₂ | |
| SCH(CH₃)CH₂CH₃ | 6-OCH₃ | NH₂ | |
| SCH(CH₃)CH₂CH₃ | 3-CF₃ | NH₂ | |
| SCH(CH₃)CH₂CH₃ | 5-CF₃ | NH₂ | |
| SCH(CH₃)CH₂CH₃ | 6-CF₃ | NH₂ | |
| SCH(CH₃)CH₂CH₃ | 5-F | NH₂ | |
| SCH(CH₃)CH₂CH₃ | 5-Br | NH₂ | |
| SCH(CH₃)CH₂CH₃ | 5-NO₂ | NH₂ | |
| SCH(CH₃)CH₂CH₃ | 5-CN | NH₂ | |
| SO₂CH(CH₃)CH₂CH₃ | H | NH₂ | 150–168° |
| SO₂CH(CH₃)CH₂CH₃ | 3-Cl | NH₂ | |
| SO₂CH(CH₃)CH₂CH₃ | 5-Cl | NH₂ | |
| SO₂CH(CH₃)CH₂CH₃ | 6-Cl | NH₂ | |
| SO₂CH(CH₃)CH₂CH₃ | 3-CH₃ | NH₂ | |
| SO₂CH(CH₃)CH₂CH₃ | 5-CH₃ | NH₂ | |
| SO₂CH(CH₃)CH₂CH₃ | 6-CH₃ | NH₂ | |
| SO₂CH(CH₃)CH₂CH₃ | 3-OCH₃ | NH₂ | |
| SO₂CH(CH₃)CH₂CH₃ | 5-OCH₃ | NH₂ | |
| SO₂CH(CH₃)CH₂CH₃ | 6-OCH₃ | NH₂ | |
| SO₂CH(CH₃)CH₂CH₃ | 3-CF₃ | NH₂ | |
| SO₂CH(CH₃)CH₂CH₃ | 5-CF₃ | NH₂ | |
| SO₂CH(CH₃)CH₂CH₃ | 6-CF₃ | NH₂ | |
| SO₂CH(CH₃)CH₂CH₃ | 5-F | NH₂ | |
| SO₂CH(CH₃)CH₂CH₃ | 5-Br | NH₂ | |
| SO₂CH(CH₃)CH₂CH₃ | 5-NO₂ | NH₂ | |

TABLE III-continued $$\underset{R_2}{\overset{H}{\underset{5}{\bigvee}}}\overset{3}{\underset{6}{\bigvee}}\overset{R_1}{\underset{SO_2Q}{}}$$

| R₁ | R₂ | Q | m.p. (°C.) |
|---|---|---|---|
| SO₂CH(CH₃)CH₂CH₃ | 5-CN | NH₂ | |
| SCH₂–△ | H | NH₂ | |
| SCH₂–△ | 3-Cl | NH₂ | |
| SCH₂–△ | 5-Cl | NH₂ | |
| SCH₂–△ | 6-Cl | NH₂ | |
| SCH₂–△ | 3-CH₃ | NH₂ | |
| SCH₂–△ | 5-CH₃ | NH₂ | |
| SCH₂–△ | 6-CH₃ | NH₂ | |
| SCH₂–△ | 3-OCH₃ | NH₂ | |
| SCH₂–△ | 5-OCH₃ | NH₂ | |
| SCH₂–△ | 6-OCH₃ | NH₂ | |
| SCH₂–△ | 3-CF₃ | NH₂ | |
| SCH₂–△ | 5-CF₃ | NH₂ | |
| SCH₂–△ | 6-CF₃ | NH₂ | |
| SCH₂–△ | 5-F | NH₂ | |
| SCH₂–△ | 5-Br | NH₂ | |
| SCH₂–△ | 5-NO₂ | NH₂ | |
| SCH₂–△ | 5-CN | NH₂ | |
| SO₂CH₂–△ | H | NH₂ | |
| SO₂CH₂–△ | 3-Cl | NH₂ | |
| SO₂CH₂–△ | 5-Cl | NH₂ | |
| SO₂CH₂–△ | 6-Cl | NH₂ | |
| SO₂CH₂–△ | 3-CH₃ | NH₂ | |
| SO₂CH₂–△ | 5-CH₃ | NH₂ | |
| SO₂CH₂–△ | 6-CH₃ | NH₂ | |
| SO₂CH₂–△ | 3-OCH₃ | NH₂ | |
| SO₂CH₂–△ | 5-OCH₃ | NH₂ | |
| SO₂CH₂–△ | 6-OCH₃ | NH₂ | |
| SO₂CH₂–△ | 3-CF₃ | NH₂ | |
| SO₂CH₂–△ | 5-CF₃ | NH₂ | |
| SO₂CH₂–△ | 6-CF₃ | NH₂ | |
| SO₂CH₂–△ | 5-F | NH₂ | |
| SO₂CH₂–△ | 5-Br | NH₂ | |
| SO₂CH₂–△ | 5-NO₂ | NH₂ | |
| SO₂CH₂–△ | 5-CN | NH₂ | |
| SCH₂CH=CH₂ | H | NH₂ | 49–52° |

TABLE III-continued

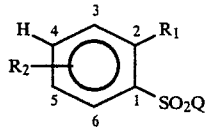

| R₁ | R₂ | Q | m.p. (°C.) |
|---|---|---|---|
| SCH₂CH=CH₂ | 3-Cl | NH₂ | |
| SCH₂CH=CH₂ | 5-Cl | NH₂ | |
| SCH₂CH=CH₂ | 6-Cl | NH₂ | |
| SCH₂CH=CH₂ | 3-CH₃ | NH₂ | |
| SCH₂CH=CH₂ | 5-CH₃ | NH₂ | |
| SCH₂CH=CH₂ | 6-CH₃ | NH₂ | |
| SCH₂CH=CH₂ | 3-OCH₃ | NH₂ | |
| SCH₂CH=CH₂ | 5-OCH₃ | NH₂ | |
| SCH₂CH=CH₂ | 6-OCH₃ | NH₂ | |
| SCH₂CH=CH₂ | 3-CF₃ | NH₂ | |
| SCH₂CH=CH₂ | 5-CF₃ | NH₂ | |
| SCH₂CH=CH₂ | 6-CF₃ | NH₂ | |
| SCH₂CH=CH₂ | 5-F | NH₂ | |
| SCH₂CH=CH₂ | 5-Br | NH₂ | |
| SCH₂CH=CH₂ | 5-NO₂ | NH₂ | |
| SCH₂CH=CH₂ | 5-CN | NH₂ | |
| SO₂CH₂CH=CH₂ | H | NH₂ | 126–128° |
| SO₂CH₂CH=CH₂ | 3-Cl | NH₂ | |
| SO₂CH₂CH=CH₂ | 5-Cl | NH₂ | |
| SO₂CH₂CH=CH₂ | 6-Cl | NH₂ | |
| SO₂CH₂CH=CH₂ | 3-CH₃ | NH₂ | |
| SO₂CH₂CH=CH₂ | 5-CH₃ | NH₂ | |
| SO₂CH₂CH=CH₂ | 6-CH₃ | NH₂ | |
| SO₂CH₂CH=CH₂ | 3-OCH₃ | NH₂ | |
| SO₂CH₂CH=CH₂ | 5-OCH₃ | NH₂ | |
| SO₂CH₂CH=CH₂ | 6-OCH₃ | NH₂ | |
| SO₂CH₂CH=CH₂ | 3-CF₃ | NH₂ | |
| SO₂CH₂CH=CH₂ | 5-CF₃ | NH₂ | |
| SO₂CH₂CH=CH₂ | 6-CF₃ | NH₂ | |
| SO₂CH₂CH=CH₂ | 5-F | NH₂ | |
| SO₂CH₂CH=CH₂ | 5-Br | NH₂ | |
| SO₂CH₂CH=CH₂ | 5-NO₂ | NH₂ | |
| SO₂CH₂CH=CH₂ | 5-CN | NH₂ | |
| SCH₂CH₂CH₃ | H | NCO | oil |
| SCH₂CH₂CH₃ | 3-Cl | NCO | |
| SCH₂CH₂CH₃ | 5-Cl | NCO | |
| SCH₂CH₂CH₃ | 6-Cl | NCO | |
| SCH₂CH₂CH₃ | 3-CH₃ | NCO | |
| SCH₂CH₂CH₃ | 5-CH₃ | NCO | |
| SCH₂CH₂CH₃ | 6-CH₃ | NCO | |
| SCH₂CH₂CH₃ | 3-OCH₃ | NCO | |
| SCH₂CH₂CH₃ | 5-OCH₃ | NCO | |
| SCH₂CH₂CH₃ | 6-OCH₃ | NCO | |
| SCH₂CH₂CH₃ | 3-CF₃ | NCO | |
| SCH₂CH₂CH₃ | 5-CF₃ | NCO | |
| SCH₂CH₂CH₃ | 6-CF₃ | NCO | |
| SCH₂CH₂CH₃ | 5-F | NCO | |
| SCH₂CH₂CH₃ | 5-Br | NCO | |
| SCH₂CH₂CH₃ | 5-NO₂ | NCO | |
| SCH₂CH₂CH₃ | 5-CN | NCO | |
| SO₂CH₂CH₂CH₃ | H | NCO | oil (IR: 2230 cm⁻¹) |
| SO₂CH₂CH₂CH₃ | 3-Cl | NCO | |
| SO₂CH₂CH₂CH₃ | 5-Cl | NCO | |
| SO₂CH₂CH₂CH₃ | 6-Cl | NCO | |
| SO₂CH₂CH₂CH₃ | 3-CH₃ | NCO | |
| SO₂CH₂CH₂CH₃ | 5-CH₃ | NCO | |
| SO₂CH₂CH₂CH₃ | 6-CH₃ | NCO | |
| SO₂CH₂CH₂CH₃ | 3-OCH₃ | NCO | |
| SO₂CH₂CH₂CH₃ | 5-OCH₃ | NCO | |
| SO₂CH₂CH₂CH₃ | 6-OCH₃ | NCO | |
| SO₂CH₂CH₂CH₃ | 3-CF₃ | NCO | |
| SO₂CH₂CH₂CH₃ | 5-CF₃ | NCO | |
| SO₂CH₂CH₂CH₃ | 6-CF₃ | NCO | |
| SO₂CH₂CH₂CH₃ | 5-F | NCO | |
| SO₂CH₂CH₂CH₃ | 5-Br | NCO | |
| SO₂CH₂CH₂CH₃ | 5-NO₂ | NCO | |
| SO₂CH₂CH₂CH₃ | 5-CN | NCO | |
| SCH(CH₃)₂ | H | NCO | |
| SCH(CH₃)₂ | 3-Cl | NCO | |
| SCH(CH₃)₂ | 5-Cl | NCO | |
| SCH(CH₃)₂ | 6-Cl | NCO | |
| SCH(CH₃)₂ | 3-CH₃ | NCO | |

TABLE III-continued

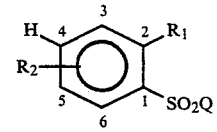

| R₁ | R₂ | Q | m.p. (°C.) |
|---|---|---|---|
| SCH(CH₃)₂ | 5-CH₃ | NCO | |
| SCH(CH₃)₂ | 6-CH₃ | NCO | |
| SCH(CH₃)₂ | 3-OCH₃ | NCO | |
| SCH(CH₃)₂ | 5-OCH₃ | NCO | |
| SCH(CH₃)₂ | 6-OCH₃ | NCO | |
| SCH(CH₃)₂ | 3-CF₃ | NCO | |
| SCH(CH₃)₂ | 5-CF₃ | NCO | |
| SCH(CH₃)₂ | 6-CF₃ | NCO | |
| SCH(CH₃)₂ | 5-F | NCO | |
| SCH(CH₃)₂ | 5-Br | NCO | |
| SCH(CH₃)₂ | 5-NO₂ | NCO | |
| SCH(CH₃)₂ | 5-CN | NCO | |
| SO₂CH(CH₃)₂ | H | NCO | oil (IR: 2200 cm⁻¹) |
| SO₂CH(CH₃)₂ | 3-Cl | NCO | |
| SO₂CH(CH₃)₂ | 5-Cl | NCO | |
| SO₂CH(CH₃)₂ | 6-Cl | NCO | |
| SO₂CH(CH₃)₂ | 3-CH₃ | NCO | |
| SO₂CH(CH₃)₂ | 5-CH₃ | NCO | |
| SO₂CH(CH₃)₂ | 6-CH₃ | NCO | |
| SO₂CH(CH₃)₂ | 3-OCH₃ | NCO | |
| SO₂CH(CH₃)₂ | 5-OCH₃ | NCO | |
| SO₂CH(CH₃)₂ | 6-OCH₃ | NCO | |
| SO₂CH(CH₃)₂ | 3-CF₃ | NCO | |
| SO₂CH(CH₃)₂ | 5-CF₃ | NCO | |
| SO₂CH(CH₃)₂ | 6-CF₃ | NCO | |
| SO₂CH(CH₃)₂ | 5-F | NCO | |
| SO₂CH(CH₃)₂ | 5-Br | NCO | |
| SO₂CH(CH₃)₂ | 5-NO₂ | NCO | |
| SO₂CH(CH₃)₂ | 5-CN | NCO | |
| SCH₂CH₂CH₂CH₃ | H | NCO | |
| SCH₂CH₂CH₂CH₃ | 3-Cl | NCO | |
| SCH₂CH₂CH₂CH₃ | 5-Cl | NCO | |
| SCH₂CH₂CH₂CH₃ | 6-Cl | NCO | |
| SCH₂CH₂CH₂CH₃ | 3-CH₃CH | NCO | |
| SCH₂CH₂CH₂CH₃ | 5-CH₃ | NCO | |
| SCH₂CH₂CH₂CH₃ | 6-CH₃ | NCO | |
| SCH₂CH₂CH₂CH₃ | 3-OCH₃ | NCO | |
| SCH₂CH₂CH₂CH₃ | 5-OCH₃ | NCO | |
| SCH₂CH₂CH₂CH₃ | 6-OCH₃ | NCO | |
| SCH₂CH₂CH₂CH₃ | 3-CF₃ | NCO | |
| SCH₂CH₂CH₂CH₃ | 5-CF₃ | NCO | |
| SCH₂CH₂CH₂CH₃ | 6-CF₃ | NCO | |
| SCH₂CH₂CH₂CH₃ | 5-F | NCO | |
| SCH₂CH₂CH₂CH₃ | 5-Br | NCO | |
| SCH₂CH₂CH₂CH₃ | 5-NO₂ | NCO | |
| SCH₂CH₂CH₂CH₃ | 5-CN | NCO | |
| SO₂CH₂CH₂CH₂CH₃ | H | NCO | oil |
| SO₂CH₂CH₂CH₂CH₃ | 3-Cl | NCO | |
| SO₂CH₂CH₂CH₂CH₃ | 5-Cl | NCO | |
| SO₂CH₂CH₂CH₂CH₃ | 6-Cl | NCO | |
| SO₂CH₂CH₂CH₂CH₃ | 3-CH₃ | NCO | |
| SO₂CH₂CH₂CH₂CH₃ | 5-CH₃ | NCO | |
| SO₂CH₂CH₂CH₂CH₃ | 6-CH₃ | NCO | |
| SO₂CH₂CH₂CH₂CH₃ | 3-OCH₃ | NCO | |
| SO₂CH₂CH₂CH₂CH₃ | 5-OCH₃ | NCO | |
| SO₂CH₂CH₂CH₂CH₃ | 6-OCH₃ | NCO | |
| SO₂CH₂CH₂CH₂CH₃ | 3-CF₃ | NCO | |
| SO₂CH₂CH₂CH₂CH₃ | 5-CF₃ | NCO | |
| SO₂CH₂CH₂CH₂CH₃ | 6-CF₃ | NCO | |
| SO₂CH₂CH₂CH₂CH₃ | 5-F | NCO | |
| SO₂CH₂CH₂CH₂CH₃ | 5-Br | NCO | |
| SO₂CH₂CH₂CH₂CH₃ | 5-NO₂ | NCO | |
| SO₂CH₂CH₂CH₂CH₃ | 5-CN | NCO | |
| SCH₂CH(CH₃)₂ | H | NCO | |
| SCH₂CH(CH₃)₂ | 3-Cl | NCO | |
| SCH₂CH(CH₃)₂ | 5-Cl | NCO | |
| SCH₂CH(CH₃)₂ | 6-Cl | NCO | |
| SCH₂CH(CH₃)₂ | 3-CH₃ | NCO | |
| SCH₂CH(CH₃)₂ | 5-CH₃ | NCO | |
| SCH₂CH(CH₃)₂ | 6-CH₃ | NCO | |
| SCH₂CH(CH₃)₂ | 3-OCH₃ | NCO | |
| SCH₂CH(CH₃)₂ | 5-OCH₃ | NCO | |

TABLE III-continued

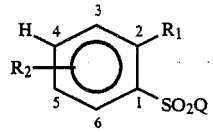

| R₁ | R₂ | Q | m.p. (°C.) |
|---|---|---|---|
| SCH₂CH(CH₃)₂ | 6-OCH₃ | NCO | |
| SCH₂CH(CH₃)₂ | 3-CF₃ | NCO | |
| SCH₂CH(CH₃)₂ | 5-CF₃ | NCO | |
| SCH₂CH(CH₃)₂ | 6-CF₃ | NCO | |
| SCH₂CH(CH₃)₂ | 5-F | NCO | |
| SCH₂CH(CH₃)₂ | 5-Br | NCO | |
| SCH₂CH(CH₃)₂ | 5-NO₂ | NCO | |
| SCH₂CH(CH₃)₂ | 5-CN | NCO | |
| SO₂CH₂CH(CH₃)₂ | H | NCO | oil |
| SO₂CH₂CH(CH₃)₂ | 3-Cl | NCO | |
| SO₂CH₂CH(CH₃)₂ | 5-Cl | NCO | |
| SO₂CH₂CH(CH₃)₂ | 6-Cl | NCO | |
| SO₂CH₂CH(CH₃)₂ | 3-CH₃ | NCO | |
| SO₂CH₂CH(CH₃)₂ | 5-CH₃ | NCO | |
| SO₂CH₂CH(CH₃)₂ | 6-CH₃ | NCO | |
| SO₂CH₂CH(CH₃)₂ | 3-OCH₃ | NCO | |
| SO₂CH₂CH(CH₃)₂ | 5-OCH₃ | NCO | |
| SO₂CH₂CH(CH₃)₂ | 6-OCH₃ | NCO | |
| SO₂CH₂CH(CH₃)₂ | 3-CF₃ | NCO | |
| SO₂CH₂CH(CH₃)₂ | 5-CF₃ | NCO | |
| SO₂CH₂CH(CH₃)₂ | 6-CF₃ | NCO | |
| SO₂CH₂CH(CH₃)₂ | 5-F | NCO | |
| SO₂CH₂CH(CH₃)₂ | 5-Br | NCO | |
| SO₂CH₂CH(CH₃)₂ | 5-NO₂ | NCO | |
| SO₂CH₂CH(CH₃)₂ | 5-CN | NCO | |
| SCH(CH₃)CH₂CH₃ | H | NCO | |
| SCH(CH₃)CH₂CH₃ | 3-Cl | NCO | |
| SCH(CH₃)CH₂CH₃ | 5-Cl | NCO | |
| SCH(CH₃)CH₂CH₃ | 6-Cl | NCO | |
| SCH(CH₃)CH₂CH₃ | 3-CH₃ | NCO | |
| SCH(CH₃)CH₂CH₃ | 5-CH₃ | NCO | |
| SCH(CH₃)CH₂CH₃ | 6-CH₃ | NCO | |
| SCH(CH₃)CH₂CH₃ | 3-OCH₃ | NCO | |
| SCH(CH₃)CH₂CH₃ | 5-OCH₃ | NCO | |
| SCH(CH₃)CH₂CH₃ | 6-OCH₃ | NCO | |
| SCH(CH₃)CH₂CH₃ | 3-CF₃ | NCO | |
| SCH(CH₃)CH₂CH₃ | 5-CF₃ | NCO | |
| SCH(CH₃)CH₂CH₃ | 6-CF₃ | NCO | |
| SCH(CH₃)CH₂CH₃ | 5-F | NCO | |
| SCH(CH₃)CH₂CH₃ | 5-Br | NCO | |
| SCH(CH₃)CH₂CH₃ | 5-NO₂ | NCO | |
| SCH(CH₃)CH₂CH₃ | 5-CN | NCO | |
| SO₂CH(CH₃)CH₂CH₃ | H | NCO | oil |
| SO₂CH(CH₃)CH₂CH₃ | 3-Cl | NCO | |
| SO₂CH(CH₃)CH₂CH₃ | 5-Cl | NCO | |
| SO₂CH(CH₃)CH₂CH₃ | 6-Cl | NCO | |
| SO₂CH(CH₃)CH₂CH₃ | 3-CH₃ | NCO | |
| SO₂CH(CH₃)CH₂CH₃ | 5-CH₃ | NCO | |
| SO₂CH(CH₃)CH₂CH₃ | 6-CH₃ | NCO | |
| SO₂CH(CH₃)CH₂CH₃ | 3-OCH₃ | NCO | |
| SO₂CH(CH₃)CH₂CH₃ | 5-OCH₃ | NCO | |
| SO₂CH(CH₃)CH₂CH₃ | 6-OCH₃ | NCO | |
| SO₂CH(CH₃)CH₂CH₃ | 3-CF₃ | NCO | |
| SO₂CH(CH₃)CH₂CH₃ | 5-CF₃ | NCO | |
| SO₂CH(CH₃)CH₂CH₃ | 6-CF₃ | NCO | |
| SO₂CH(CH₃)CH₂CH₃ | 5-F | NCO | |
| SO₂CH(CH₃)CH₂CH₃ | 5-Br | NCO | |
| SO₂CH(CH₃)CH₂CH₃ | 5-NO₂ | NCO | |
| SO₂CH(CH₃)CH₂CH₃ | 5-CN | NCO | |
| SCH₂-cyclopropyl | H | NCO | |
| SCH₂-cyclopropyl | 3-Cl | NCO | |
| SCH₂-cyclopropyl | 5-Cl | NCO | |

TABLE III-continued

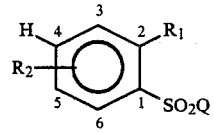

| R₁ | R₂ | Q | m.p. (°C.) |
|---|---|---|---|
| SCH₂-cyclopropyl | 6-Cl | NCO | |
| SCH₂-cyclopropyl | 3-CH₃ | NCO | |
| SCH₂-cyclopropyl | 5-CH₃ | NCO | |
| SCH₂-cyclopropyl | 6-CH₃ | NCO | |
| SCH₂-cyclopropyl | 3-OCH₃ | NCO | |
| SCH₂-cyclopropyl | 5-OCH₃ | NCO | |
| SCH₂-cyclopropyl | 3-CF₃ | NCO | |
| SCH₂-cyclopropyl | 3-CF₃ | NCO | |
| SCH₂-cyclopropyl | 5-CF₃ | NCO | |
| SCH₂-cyclopropyl | 6-CF₃ | NCO | |
| SCH₂-cyclopropyl | 5-F | NCO | |
| SCH₂-cyclopropyl | 5-Br | NCO | |
| SCH₂-cyclopropyl | 5-NO₂ | NCO | |
| SCH₂-cyclopropyl | 5-CN | NCO | |
| SO₂CH₂-cyclopropyl | H | NCO | oil (IR: 2250 cm⁻¹) |
| SO₂CH₂-cyclopropyl | 3-Cl | NCO | |
| SO₂CH₂-cyclopropyl | 5-Cl | NCO | |

TABLE III-continued

Structure: benzene ring with H at position 4, R₂ at position 5, R₁ at position 2, SO₂Q at position 1 (positions 3 and 6 also shown)

| R₁ | R₂ | Q | m.p. (°C.) |
|---|---|---|---|
| SO₂CH₂-cyclopropyl | 6-Cl | NCO | |
| SO₂CH₂-cyclopropyl | 3-CH₃ | NCO | |
| SO₂CH₂-cyclopropyl | 5-CH₃ | NCO | |
| SO₂CH₂-cyclopropyl | 6-CH₃ | NCO | |
| SO₂CH₂-cyclopropyl | 3-OCH₃ | NCO | |
| SO₂CH₂-cyclopropyl | 5-OCH₃ | NCO | |
| SO₂CH₂-cyclopropyl | 6-OCH₃ | NCO | |
| SO₂CH₂-cyclopropyl | 3-CF₃ | NCO | |
| SO₂CH₂-cyclopropyl | 5-CF₃ | NCO | |
| SO₂CH₂-cyclopropyl | 6-CF₃ | NCO | |
| SO₂CH₂-cyclopropyl | 5-F | NCO | |
| SO₂CH₂-cyclopropyl | 5-Br | NCO | |
| SO₂CH₂-cyclopropyl | 5-NO₂ | NCO | |
| SO₂CH₂-cyclopropyl | 5-CN | NCO | |
| SCH₂CH=CH₂ | H | NCO | |
| SCH₂CH=CH₂ | 3-Cl | NCO | |
| SCH₂CH=CH₂ | 5-Cl | NCO | |
| SCH₂CH=CH₂ | 6-Cl | NCO | |
| SCH₂CH=CH₂ | 3-CH₃ | NCO | |
| SCH₂CH=CH₂ | 5-CH₃ | NCO | |
| SCH₂CH=CH₂ | 6-CH₃ | NCO | |
| SCH₂CH=CH₂ | 3-OCH₃ | NCO | |
| SCH₂CH=CH₂ | 5-OCH₃ | NCO | |
| SCH₂CH=CH₂ | 6-OCH₃ | NCO | |
| SCH₂CH=CH₂ | 3-CF₃ | NCO | |
| SCH₂CH=CH₂ | 5-CF₃ | NCO | |
| SCH₂CH=CH₂ | 6-CF₃ | NCO | |
| SCH₂CH=CH₂ | 5-F | NCO | |
| SCH₂CH=CH₂ | 5-Br | NCO | |
| SCH₂CH=CH₂ | 5-NO₂ | NCO | |
| SCH₂CH=CH₂ | 5-CN | NCO | |
| SO₂CH₂CH=CH₂ | H | NCO | |
| SO₂CH₂CH=CH₂ | 3-Cl | NCO | |
| SO₂CH₂CH=CH₂ | 5-Cl | NCO | |
| SO₂CH₂CH=CH₂ | 6-Cl | NCO | |
| SO₂CH₂CH=CH₂ | 3-CH₃ | NCO | |
| SO₂CH₂CH=CH₂ | 5-CH₃ | NCO | |
| SO₂CH₂CH=CH₂ | 6-CH₃ | NCO | |
| SO₂CH₂CH=CH₂ | 3-OCH₃ | NCO | |
| SO₂CH₂CH=CH₂ | 5-OCH₃ | NCO | |
| SO₂CH₂CH=CH₂ | 6-OCH₃ | NCO | |
| SO₂CH₂CH=CH₂ | 3-CF₃ | NCO | |
| SO₂CH₂CH=CH₂ | 5-CF₃ | NCO | |
| SO₂CH₂CH=CH₂ | 6-CF₃ | NCO | |
| SO₂CH₂CH=CH₂ | 5-F | NCO | |
| SO₂CH₂CH=CH₂ | 5-Br | NCO | |
| SO₂CH₂CH=CH₂ | 5-NO₂ | NCO | |
| SO₂CH₂CH=CH₂ | 5-CN | NCO | |
| SCH₂CH=CHCH₃ | H | NH₂ | |
| SCH₂CH=CHCH₃ | 5-Cl | NH₂ | |
| SCH₂CH=CHCH₃ | 5-CH₃ | NH₂ | |
| SCH₂CH=CHCH₃ | 5-CF₃ | NH₂ | |
| SCH₂CH=CHCH₃ | 5-OCH₃ | NH₂ | |
| SCH₂CH=CHCH₃ | 5-F | NH₂ | |
| SCH₂CH=CHCH₃ | 5-Br | NH₂ | |
| SCH₂CH=CHCH₃ | 5-NO₂ | NH₂ | |
| SCH₂CH=CHCH₃ | 5-CN | NH₂ | |
| SO₂CH₂CH=CHCH₃ | H | NH₂ | |
| SO₂CH₂CH=CHCH₃ | 5-Cl | NH₂ | |
| SO₂CH₂CH=CHCH₃ | 5-CH₃ | NH₂ | |
| SO₂CH₂CH=CHCH₃ | 5-CF₃ | NH₂ | |
| SO₂CH₂CH=CHCH₃ | 5-OCH₃ | NH₂ | |
| SO₂CH₂CH=CHCH₃ | 5-F | NH₂ | |
| SO₂CH₂CH=CHCH₃ | 5-Br | NH₂ | |
| SO₂CH₂CH=CHCH₃ | 5-NO₂ | NH₂ | |
| SO₂CH₂CH=CHCH₃ | 5-CN | NH₂ | |
| SCH₂CH=CHCH₃ | H | NCO | |
| SCH₂CH=CHCH₃ | 5-Cl | NCO | |
| SCH₂CH=CHCH₃ | 5-CH₃ | NCO | |
| SCH₂CH=CHCH₃ | 5-CF₃ | NCO | |
| SCH₂CH=CHCH₃ | 5-OCH₃ | NCO | |
| SCH₂CH=CHCH₃ | 5-F | NCO | |
| SCH₂CH=CHCH₃ | 5-Br | NCO | |
| SCH₂CH=CHCH₃ | 5-NO₂ | NCO | |
| SCH₂CH=CHCH₃ | 5-CN | NCO | |
| SO₂CH₂CH=CHCH₃ | H | NCO | |
| SO₂CH₂CH=CHCH₃ | 5-Cl | NCO | |
| SO₂CH₂CH=CHCH₃ | 5-CH₃ | NCO | |
| SO₂CH₂CH=CHCH₃ | 5-CF₃ | NCO | |
| SO₂CH₂CH=CHCH₃ | 5-OCH₃ | NCO | |
| SO₂CH₂CH=CHCH₃ | 5-F | NCO | |
| SO₂CH₂CH=CHCH₃ | 5-Br | NCO | |
| SO₂CH₂CH=CHCH₃ | 5-NO₂ | NCO | |
| SO₂CH₂CH=CHCH₃ | 5-CN | NCO | |
| SC(CH₃)₃ | H | NH₂ | |
| SC(CH₃)₃ | 5-Cl | NH₂ | |
| SC(CH₃)₃ | 5-CH₃ | NH₂ | |
| SC(CH₃)₃ | 5-CF₃ | NH₂ | |
| SC(CH₃)₃ | 5-OCH₃ | NH₂ | |
| SC(CH₃)₃ | 5-F | NH₂ | |
| SC(CH₃)₃ | 5-Br | NH₂ | |
| SC(CH₃)₃ | 5-NO₂ | NH₂ | |
| SC(CH₃)₃ | 5-CN | NH₂ | |
| SO₂C(CH₃)₃ | H | NH₂ | 134–142° |
| SO₂C(CH₃)₃ | 5-Cl | NH₂ | |
| SO₂C(CH₃)₃ | 5-CH₃ | NH₂ | |
| SO₂C(CH₃)₃ | 5-CF₃ | NH₂ | |
| SO₂C(CH₃)₃ | 5-OCH₃ | NH₂ | |
| SO₂C(CH₃)₃ | 5-F | NH₂ | |
| SO₂C(CH₃)₃ | 5-Br | NH₂ | |
| SO₂C(CH₃)₃ | 5-NO₂ | NH₂ | |
| SO₂C(CH₃)₃ | 5-CN | NH₂ | |
| SC(CH₃)₃ | H | NCO | |
| SC(CH₃)₃ | 5-Cl | NCO | |

TABLE III-continued

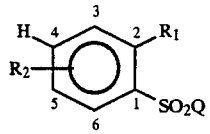

| R₁ | R₂ | Q | m.p. (°C.) |
|---|---|---|---|
| SC(CH₃)₃ | 5-CH₃ | NCO | |
| SC(CH₃)₃ | 5-CF₃ | NCO | |
| SC(CH₃)₃ | 5-OCH₃ | NCO | |
| SC(CH₃)₃ | 5-F | NCO | |
| SC(CH₃)₃ | 5-Br | NCO | |
| SC(CH₃)₃ | 5-NO₂ | NCO | |
| SC(CH₃)₃ | 5-CN | NCO | |
| SO₂C(CH₃)₃ | H | NCO | oil |
| SO₂C(CH₃)₃ | 5-Cl | NCO | |
| SO₂C(CH₃)₃ | 5-CH₃ | NCO | |
| SO₂C(CH₃)₃ | 5-CF₃ | NCO | |
| SO₂C(CH₃)₃ | 5-OCH₃ | NCO | |
| SO₂C(CH₃)₃ | 5-F | NCO | |
| SO₂C(CH₃)₃ | 5-Br | NCO | |
| SO₂C(CH₃)₃ | 5-NO₂ | NCO | |
| SO₂C(CH₃)₃ | 5-CN | NCO | |
| SCH₂CH₂CH₃ | H | NCS | |
| SO₂CH₂CH₂CH₃ | H | NCS | |
| SCH(CH₃)₂ | H | NCS | |
| SO₂CH(CH₃)₂ | H | NCS | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IV

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 10

| Wettable Powder | |
|---|---|
| N—[(4-methoxy-6-methylpyrimidin-2-yl)aminocarbonyl]-2-[(1-methylethyl)sulfonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 11

| Wettable Powder | |
|---|---|
| N—[(4,6-dimethoxypyrimidin-2-yl)aminocarbonyl]-2-[(1-methylethyl)sulfonyl]benzenesulfonamide | 50% |
| sodium alkylnaphthalenesulfonate | 2% |
| low viscosity methyl cellulose | 2% |

-continued

| Wettable Powder | |
|---|---|
| diatomaceous earth | 46% |

The ingredients are blended, coarsely hammer-milled and then air-milled to produce particles essentially all below 10 microns in diameter. The product is reblended before packaging.

EXAMPLE 12

| Granule | |
|---|---|
| Wettable Powder of Example 11 | 5% |
| attapulgite granules | 95% |
| (U.S.S. 20–40 mesh; 0.84–0.42 mm) | |

A slurry of wettable powder containing ≈25% solids is sprayed on the surface of attapulgite granules in a double-cone blender. The granules are dried and packaged.

EXAMPLE 13

| Extruded Pellet | |
|---|---|
| N—[(4,6-dimetylpyrimidin-2-yl)aminocarbonyl]-2-[(1-methylethyl)sulfonyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

| Oil Suspension | |
|---|---|
| N—[(4,6-dimethoxypyrimidin-2-yl)aminocarbonyl]-2-(popylsulfonyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 15

| Wettable Powder | |
|---|---|
| N—[(4,6-dimethoxy-1,3,5-triazin-2-yl)aminocarbonyl]-2-(propylsulfonyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 16

| Low Strength Granule | |
|---|---|
| N—[(4-methoxy-6-methyl-1,3,5-triazin-2-yl)aminocarbonyl]-2-(propylsulfonyl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 17

| Aqueous Suspension | |
|---|---|
| N—[(4,6-dimethyl-1,3,5-triazin-2-yl)aminocarbonyl]-2-(propylsulfonyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 18

| Solution | |
|---|---|
| N—[(4-methoxy-6-methyl-1,3,5-triazin-2-yl)aminocarbonyl]-2-[(1-methylethyl)sulfonyl]benzenesulfonamide, sodium salt | 5% |
| water | 95% |

The salt is added directly to the water with stirring to produce the solution, which may then be packaged for use.

EXAMPLE 19

| Low Strength Granule | |
|---|---|
| N—[(4-methoxy-6-methylpyrimidin-2-yl)aminocarbonyl]-2-(propylsulfonyl)benzenesulfonamlde | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

| Granule | |
|---|---|
| N—[(4,6-dimethylpyrimidin-2-yl)aminocarbonyl]-2-(propylsulfonyl)benzenesulfonamide | 80% |

| Granule | |
|---|---|
| wetting agent | 1% |
| crude liginsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 21

| High Strength Concentrate | |
|---|---|
| N—[(4-chloro-6-methoxypyrimidin-2-yl)aminocarbonyl]-2-(propylsulfonyl)benzenesulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 22

| Wettable Powder | |
|---|---|
| N—[(4,6-dimethyl-1,3,5-triazin-2-yl)aminocarbonyl]-2-[(1-methylethyl)sulfonyl]benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 23

| Wettable Powder | |
|---|---|
| N—[(4-dimethylamino-6-methoxy-1,3,5-triazin-2-yl)-aminocarbonyl]-2-(propylsulfonyl)benzenesulfonamide | 40% |
| sodium liginsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 24

| Oil Suspension | |
|---|---|
| N—[(4,6-dimethoxy-1,3,5-triazin-2-yl)aminocarbonyl]-2-[(1-methylethyl)sulfonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

The compounds of Formula I can be formulated using the procedures of Examples 10-24.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, MX missile sites, parking lots, drive-in theaters, around billboards, highway and railroad structures. In addition, the subject compounds distinguish themselves in being highly useful for the selective pre- or post-emergence weed control in a wide range of crops, such as soybeans, dry beans, green beans, alfalfa, tobacco, corn, cotton, wheat, barley, cucumbers, tomatoes, flax and potatoes. By properly selecting rate and time of application, compounds of this invention may be used also to modify plant growth beneficially.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of this invention may be used in combination with other commercial herbicides. They are particularly useful in combination with the following herbicides.

| Common Name | Chemical Name |
|---|---|
| acifluorfen | 5-[2-chloro-4-(trifluoromethyl)phenoxy]-2-nitrobenzoic acid |
| alachlor | 2-chloro-2',6'-diethyl-N—(methoxymethyl)-acetanilide |
| amitrole | 3-amino-s-triazole |
| atrazine | 2-chloro-4-(ethylamino)-6-(isopropylamino)-s-triazine |
| barban | 4-chloro-2-butynyl m-chlorocarbanilate |
| bentazon | 3-isopropyl-1H—2,1,3-benzothiadiazin-4(3H)—one-2,2-dioxide |
| benzoylprop | N—benzoyl-N—(3,4-dichlorophenyl)-DL-alaine |
| bromacil | 5-bromo-3-sec-butyl-6-methyluracil |
| bromoxynil | 3,5-dibromo-4-hydroxybenzonitrile |
| butylate | S—ethyl-diisobutylthiocarbamate |
| Chloramben | 3-amino-2,5-dichlorobenzoic acid |
| chlortoluron | N'—(3-Chloro-4-methylphenyl-N',N'—dimethylurea |
| cyanazine | 2-[[4-chloro-6-(ethylamino)-s-triazin-2-yl]amino]-2-methylpropionitrile |
| diallate | S—(2,3-dichloroallyl)diisopropylthiocarbamate |
| dicamba | 3,6-dichloro-o-anisic acid |

| Common Name | Chemical Name |
|---|---|
| dichloroprop | 2-(2,4-dichlorophenoxy)propionic acid |
| diclofop | 2-[4-(2,4-dichlorophenoxy)phenoxy]-propanoic acid |
| difenzoquat | 1,2-dimethyl-3,5-diphenyl-1H—pyrazolium |
| dinoseb | 2-sec-butyl-4,6-dinitrophenol |
| diuron | 3-(3,4-dichlorophenyl)-1,1-dimethylurea |
| EPTC | S—ethyl-dipropylthiocarbamate |
| flamprop | N—benzoyl-N—(3-chloro-4-fluorophenyl)-DL-alanine |
| fluazifop-butyl | butyl 2-[4-[5-(trifluoromethyl)-2-pyridinyloxy]phenoxy]propanoate |
| fluchloralin | N—(2-chloroethyl)-2,6-dinitro-N—propyl-4-trifluoromethyl)aniline |
| fluometuron | 1,1-dimethyl-3-($\alpha,\alpha,\alpha$-trifluoro-m-tolyl)-urea |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| hexazinone | 3-cyclohexyl-6-(dimethylamino)-1-methyl-1,3,5-triazine-2,4(1H,3H)—dione |
| ioxynil | 4-hydroxy-3,5-diiodobenzonitrile |
| isoproturon | N—(4-isopropylphenyl)-N',N'—dimethylurea |
| lenacil | 3-cyclohexyl-6,7-dihydro-1H—cyclopenta-pyrimidine-2,4(3H,5H)—dione |
| linuron | 3-(3,4-dichlorophenyl)-1-methoxy-1-methylurea |
| MCPA | [(4-chloro-o-tolyl)oxy]acetic acid |
| MCPB | 4-[(4-chloro-o-tolyl)oxy]propionic acid |
| mefluidide | N—[2,4-dimethyl-5-[[(trifluoromethyl)-sulfonyl]amino]phenyl]acetamide |
| methabenzthiazuron | 1,3-dimethyl-3-(2-benzothiazolyl)urea |
| methoxuron | N'-3-chloro-4-methoxyphenyl)N,N—dimethylurea |
| metolachlor | 2-chloro-N—(2-ethyl-6-methylphenyl)-N—(2-methoxy-1-methylethyl)acetamide |
| metibuzin | 4-amino-6-tert-butyl-3-(methylthio)-as-triazin-5(4H)—one |
| MSMA | monosodium methanearsonate |
| neburon | 1-butyl-3-(3,4-dichlorophenyl)-1-methylurea |
| oryzalin | 3,4-dinitro-N,N—dipropylsulfanilamide |
| paraquat | 1,1'-dimethyl-4,4'-bipyridinium ion |
| pendimethalin | N—(1-ethylpropyl)-3,4-dimethyl-2,6-dinitrobenzeneamine |
| profluralin | N—(cyclopropylmethyl)-$\alpha,\alpha,\alpha$-trifluoro-2,6-dinitro-N'propyl-p-toluidine |
| propanil | 3',4'-dichloropropionalide |
| sethoxydim | 2-[1-(ethoxyimino)butyl]-5-[2-(ethylthio)propyl]3-hydroxy-2-cyclohexene-1-one |
| siduron | 1-(2-methylcyclohexyl)-3-phenylurea |
| supriox | 2-[1-(2,5-dimethylphenyl)ethylsulfonyl]-pyridine-N—oxide |
| terbacil | 3-tert-butyl-5-chloro-6-methyluracil |
| triallate | S—(2,3,3-trichloroallyl)diisopropylthiocarbamate |
| trifluralin | $\alpha,\alpha,\alpha$-trifluoro-2,6-dinitro-N,N—dipropyl-p-toluidine |
| 2,4-D | (2,4-dichlorophenoxy)acetic acid |
| 2,4-DB | 4-(2,4-dichlorophenoxy)butyric acid |
|  | 3,4-diaryl-4-cyanobutyrates |
|  | 4-(6-chloroquinoxalinyl-2-oxy)phenoxy-propionate $C_1$-$C_5$ alkyl esters, such as methyl ester, butyl ester, ethyl ester, pentyl ester |
|  | ethoxyethoxyethyl 4-(6-chloroquinoxalin-yl-2-oxy)phenoxypropionate |
|  | propargyl 2-[4-(3,5-dichloropyridin-2-yloxy)phenoxy]propanoate |
|  | methyl 2-[4-(3-chloro-5-trifluoromethyl-pyridin-2-yloxy)phenoxy]propanoate |
| oxyfluorfen | 2-chloro-1-(3-ethoxy-4-nitrophenoxy)-4-(trifluoromethyl)benzene |
| norflurazon | 4-chloro-5-(methylamino)-2-[(3-(trifluoro)phenyl]-3(2H)—pyridazinone |
| vernolate | S—propyl dipropylthiocarbamate |
|  | ethyl 5-[2-chloro-4-(trifluoromethyl)-phenoxy]-2-nitrobenzoic acid |

The activity of these compounds was discovered in a number of greenhouse and field tests. The tests are described and the data resulting from them are shown in the following tables.

0=no effect
10=maximum effect
C=chlorosis or necrosis
D=defoliation
E=emergence inhibition
G=growth retardation
H=formative effects
U=unusual pigmentation
X=axillary stimulation
5F=earlier flowering
6Y=abscised buds or flowers.

TEST A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated pre-emergence with a non-phytotoxic solvent solution of the compounds of Table A. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment. The data in Table A shows that the compounds of this invention are very effective as herbicides and have utility for selective post-emergence weed control in wheat.

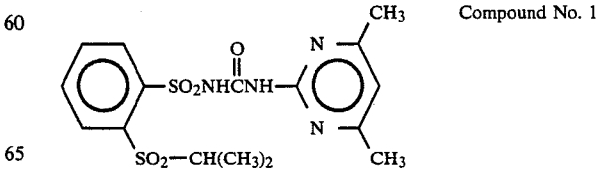

Compound No. 1

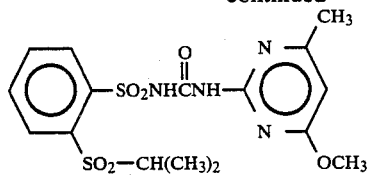

Compound No. 2

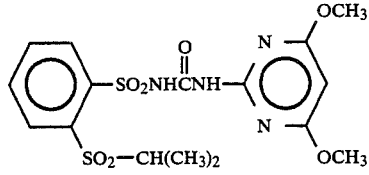

Compound No. 3

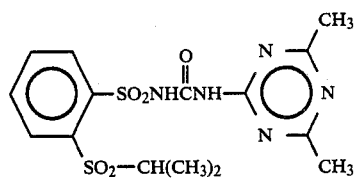

Compound No. 4

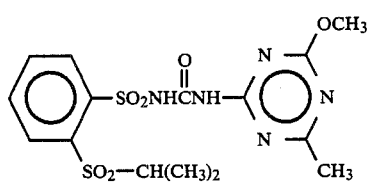

Compound No. 5

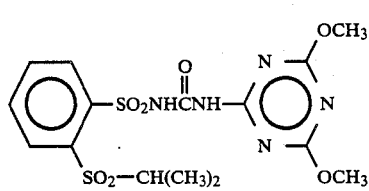

Compound No. 6

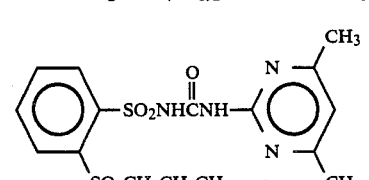

Compound No. 7

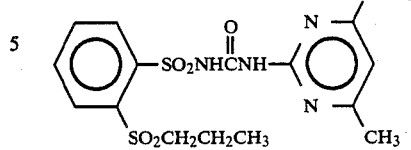

Compound No. 8

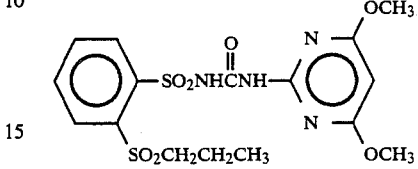

Compound No. 9

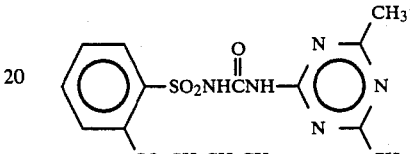

Compound No. 10

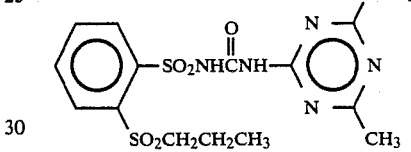

Compound No. 11

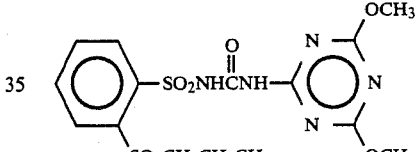

Compound No. 12

TABLE A

|  | Compound No. | | | | | |
|---|---|---|---|---|---|---|
|  | 1 | 2 | 3 | 4 | 5 | 6 |
| kg/ha | 0.1 | 0.1 | 0.1 | 0.1 | 0.1 | 0.1 |
| POST-EMERGENCE | | | | | | |
| Bushbean | 2C,5G,6Y | 5C,8G,6Y | 9C | 3C,6Y | 9C | 9C |
| Cotton | 3C,3H,6G | 4C,7G | 5C,9G | 3C,3H | 6C,8G | 6C,9G |
| Morningglory | 2C,5G,5F | 10C | 1C,2H | 2C,4G,5F | 6C,9G | 10C |
| Cocklebur | 2C,5G | 9C | 9C | 2C,2H | 5C,9G | 9C |
| Cassia | 3C | 5C,8G | 4C,8G | 1C | 2C,5G | 5C,8G |
| Nutsedge | 2G | 5G | 7G | 0 | 1C | 5G |
| Crabgrass | 2G | 2G | 2G | 1C,2G | 1C,5G | 2C,8G |
| Barnyardgrass | 2C,5H | 9C | 8H | 9C | 5C,9H | 2C,9H |
| Wild Oats | 2C,6G | 2C,5G | 1C | 2C,3G | 2C | 1C,2G |
| Wheat | 1C,2G | 2C,3G | 1C | 1C | 1C,2G | 1G |
| Corn | 2C | 1C,3G | 1C,5H | 1C,5H | 4C,9H | 9C |
| Soybean | 2C,6G | 5C,9G | 2C,8G | 2C | 5C,9G | 6C,9G |
| Rice | — | — | — | — | — | — |
| Sorghum | 3C,9H | 3C,9G | 2C,9G | 1C,9G | 2C,9G | 4C,9G |
| PRE-EMERGENCE | | | | | | |
| Morningglory | 8G | 9G | 9G | 7G | 9C,9G | 9C,9G |
| Cocklebur | 5H | 9H | 9H | 4G | 9H | 9H |
| Cassia | 1C | 8G | 8G | 1C | 2C,9G | 2C,9G |
| Nutsedge | 0 | 10E | 1C,5G | 1C,5G | 9G | 10E |
| Crabgrass | 2G | 5G | 1C,8G | 2C | 2C,8G | 2C,8G |
| Barnyardgrass | 1C,3G | 9H | 9H | 2C,4G | 2C,9H | 3C,9H |
| Wild Oats | 1C,2G | 2C,8H | 7G | 2C | 2C,7G | 1C,2G |

TABLE A-continued

| | | | | | | |
|---|---|---|---|---|---|---|
| Wheat | 1C | 1C,5G | 4G | 0 | 1C,5G | 5G |
| Corn | 3G | 1C,7G | 1C,9H | 1C,6G | 1U,9G | 1U,9G |
| Soybean | 0 | 8H | 7H | 0 | 8H | 8H |
| Rice | 2C,6H | 9H | 10E | 9H | 9H | 9H |
| Sorghum | 1C,8G | 5C,9H | 2C,9H | 1C,9G | 5C,9H | 3C,9H |

| | Compound No. | | | | | |
|---|---|---|---|---|---|---|
| | 7 | 8 | 9 | 10 | 11 | 12 |
| kg/ha | 0.4 | 0.4 | 0.4 | 0.4 | 0.4 | 0.4 |
| | POST-EMERGENCE | | | | | |
| Bushbean | 9C | 9C | 9C | 9C | 9C | 5C,9G |
| Cotton | 2U,6C,9G | 9C | 9C | 2U,5C,9G | 9C | 9C |
| Morningglory | 10C | 10C | 10C | 9C | 10C | 10C |
| Cocklebur | 9C | 10C | 9C | 9C | 9C | 10C |
| Cassia | 4C,8G | 9C | 9C | 5C,8G | 9C | 9C |
| Nutsedge | 1C,8G | 1C,9G | 5C,9G | 4G | 6G | 1C,6G |
| Crabgrass | 3C,9G | 5C,9G | 7C,9G | 2C,8G | 6C,9G | 4C,9G |
| Barnyardgrass | 9C | 9C | 9C | 2C,9H | 9C | 9C |
| Wild Oats | 9C | 9C | 5C,9H | 5C,8G | 6C,9G | 3C,7H |
| Wheat | 3C,9G | 3C,9G | 3C,9G | 1C,7G,5X | 2C,9G,5X | 1C,6G,5X |
| Corn | 2U,9H | 7U,9G | 3U,9H | 2U,9G | 8U,9G | 6U,9C |
| Soybean | 9C | 9C | 9C | 2C,8G,5X | 9C | 9C |
| Rice | 9C | 9C | 8C | 5C,9G | 7C,9G | 9C |
| Sorghum | 9C | 10C | 9C | 9C | 9C | 4U,9C |
| | PRE-EMERGENCE | | | | | |
| Morningglory | 9C | 9H | 9H | 9G | 9H | 9H |
| Cocklebur | 9H | 10E | 9H | 9H | 9H | 9H |
| Cassia | 2C,9G | 2C,9G | 2C,9G | 6C,9G | 2C,9G | 1C,9G |
| Nutsedge | 10E | 10E | 10E | 4G | 2C,8G | 8G |
| Crabgrass | 1C,5G | 5C,9G | 5C,9H | 2G | 4C,9G | 2C,8G |
| Barnyardgrass | 3C,9H | 5C,9H | 5C,9H | 4C,9H | 5C,9H | 4C,9H |
| Wild Oats | 4C,9H | 5C,9H | 5C,9H | 2C,8G | 5C,9H | 5C,9H |
| Wheat | 1C,9G | 2C,9G | 3C,9H | 1C,8G | 3C,9G | 1C,9G |
| Corn | 2C,9G | 9H | 9G | 9H | 10E | 10E |
| Soybean | 9H | 9H | 9H | 1C,2G | 9H | 2C,9H |
| Rice | 10E | 10E | 10E | 10E | 10E | 10E |
| Sorghum | 3C,9H | 6C,9H | 10H | 3C,9H | 10H | 6C,9H |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously. The data are summarized in Table B. It will be readily seen that certain compounds are useful as pre-emergence treatments for weed control in crops such as soybeans, wheat, corn and cotton.

TABLE B

| PRE-EMERGENCE ON FALLSINGTON SILT LOAM | | | | | | | | | | | | |
|---|---|---|---|---|---|---|---|---|---|---|---|---|
| | Compound No. | | | | | | | | | | | |
| | 7 | | 8 | | 2 | | | | 9 | | | |
| kg/ha | 0.03 | 0.12 | 0.03 | 0.12 | 0.03 | 0.06 | 0.12 | 0.25 | 0.03 | 0.06 | 0.12 | 0.25 |
| Crabgrass | 0 | 2G | 5G | 6G | 0 | 6G | 3G | 5G | 5G | 7G | 6G | 8G |
| Barnyardgrass | 5G | 7G,3H | 9G,8C | 9G,9C | 6G,3C | 8G,3H | 8G,4C | 9G,9C | 8G,3H | 9G,5H | 9G,9C | 10C |
| Sorghum | 9G,5H | 9G,9C | 10C | 10C | 8G,5H | 9G,9C | 10C | 10C | 9C,9C | 10C | 10C | 10C |
| Wild Oats | 7G,3H | 7G,4C | 7G,6C | 7G,6C | 4G | 4G,3C | 7G,4C | 6G,5C | 5G,3C | 3G | 7G,3C | 6G,3C |
| Johnsongrass | 6G,3H | 8G,3H | 8G,4C | 7G,4C | 6G,3H | 8G,5H | 7G,3H | 9G,7C | 7G,3H | 8G,3H | 8G,3C | 9G,9C |
| Dallisgrass | 0 | 6G | 8G | 9G,8C | 6G | — | 7G | — | 7G | — | 8G | — |
| Giant Foxtail | 0 | 6G,3H | 7G,4C | 7G,4C | 5G | 6G,3C | 7G,3C | 7G,3C | 6G,3C | 7G,5H | 8G,6C | 9G,8C |
| Ky. Bluegrass | 5G | 7G | 9G,9C | 10C | 8G,5C | 6G,3C | 8G,8C | 8G,5C | 8G,7C | 8G,5C | 8G,8C | 8G,8C |
| Cheatgrass | 7G,5E | 9G,9C | 10C | 10C | 7G,3C | 8G,8C | 8G,3C | 10E | 8G,4C | 10E | 8G,6C | 10E |
| Sugarbeets | 6G,7C | 8G,8C | 8G,8C | 8G,9C | 5G | 7G,5H | 6G,3C | 8G,8C | 7G,7C | 6G,3H | 7G,7C | 8G,8C |
| Corn | 2G | 4G,2C | 6G,3H | 8G,5H | 0 | 5G | 2H | 5G,3H | 0 | 5G,2C | 4G,3H | 6G,3C |
| Mustard | 9G,9C | 9G,9C | 9G,9C | 10C | 9G,9C | 9G,8C | 10C | 10C | 9G,9C | 10C | 10C | 10C |
| Cocklebur | 3G | 5G | 7G | 8G | 6G | 5G,3H | 6G | 6G,5H | 6G | 5G,3H | 7G | 7G,3H |
| Pigweed | 7G | 7G | 10C | 10C | 3G | 6G | 10C | 8G,8C | 5G | 4G | 9G,9C | 10C |
| Nutsedge | 0 | 3G | 8G | 7G | 5G | 6G | 6G | 7G | 10E | 7G | 8G | 10E |
| Cotton | 0 | 4G,2H | 7G,5H | 7G,5H | 0 | 4G | 5G,5H | 6G,5H | 4G,3H | 6G | 7G,5H | 8G,5H |

TABLE B-continued
PRE-EMERGENCE ON FALLSINGTON SILT LOAM

| | | | | | | | | | | | | |
|---|---|---|---|---|---|---|---|---|---|---|---|---|
| Morninglory | 7G,5H | 8G,5H | 7G,5H | 8G,5H | 4G | 4G,2H | 8G | 8G,5H | 6G | 7G,5H | 7G | 10C |
| Cessia | 5G | 5G | 7G,4C | 10E | 0 | 2G,2C | 5G,3C | 8G,3H | 8G,5C | 6G,3C | 8G,5C | 9G,6C |
| Teaweed | 0 | 8G,3C | 5G,3C | 6G,3C | 2G | 0 | 3G | 5G,3H | 5G,2C | 3G | 5G,2C | 7G |
| Velvetleaf | 5G,3H | 7G,3H | 8G,5C | 9G,9C | 3H | 3H | 6G,5H | 6G,5H | 8G,5H | 7G,5H | 9G,9C | 8G,7C |
| Jimsonweed | 4G | 5G | 6G,3C | 7G,5C | 4G,3C | 7G | 7G,5C | 7G,3C | 3G | 0 | 4G | 4G |
| Soybean | 0 | 3G | 4G,3H | 6G,5H | 0 | 4G | 4G,2C | 6G,3H | 0 | 0 | 4G | 5G,3H |
| Rice | 7G | 10E | 9G,9C | 10C | 5G | 6G,3H | 7G,3C | 7G,5H | 10E | 8G,8C | 10E | 10E |
| Wheat | 3G | 5G | 5G | 6G | 2G | 2G | 5G | 3G | 0 | 2G | 3G | 5G |

| | Compound No. | | | | | | | | | | | |
|---|---|---|---|---|---|---|---|---|---|---|---|---|
| | 3 | | | | 11 | | | | 10 | | 5 | |
| kg/ha | 0.03 | 0.06 | 0.12 | 0.25 | 0.03 | 0.06 | 0.12 | 0.25 | 0.03 | 0.12 | 0.03 | 0.12 |
| Crabgrass | 3G | 0 | 6G | 5G | 2G | 4G | 6G | 7G | 0 | 2G | 0 | 5G |
| Barnyardgrass | 5G,2C | 7G,3H | 8G,3C | 8G,3H | 4G | 6G | 8G,7C | 8G,6C | 3G | 3G | 4G | 7G,3C |
| Sorghum | 9C,9C | 10C | 9G,9C | 10C | 9C,9C | 10C | 10E | 10C | 3G | 8G,5H | 9G,8C | 10C |
| Wild Oats | 4G | 0 | 7G,3C | 5G | 6G,2H | 4G,3C | 7G,3H | 6G,4C | 0 | 6G,3H | 3G | 6G |
| Johnsongrass | 7G,3H | 7G,5H | 8G,5C | 8G,5H | 8G,5C | 9C,7C | 8G | 9G,9C | 0 | 6G,3H | 7G,3H | 8G |
| Dallisgrass | 6G | 0 | 8G | 6G,3H | 5G | — | 5G | — | 0 | 5G | 0 | 4G |
| Giant Foxtail | 8G,4C | 8G,5H | 9G,9C | 9G,5H | 3G,2C | 5G | 6G,3C | 6G,2C | 0 | 0 | 4G | 6G,3C |
| Ky. Bluegrass | 7G,5C | 7G,3C | 8G,9C | 9G,9C | 6G,2C | 7G,4C | 7G,3C | 8G,8C | 0 | 3G | 6G | 7G,3C |
| Cheatgrass | 8G,5C | 8G,5H | 8G,8C | 8G,9C | 7G | 10C | 8G,3C | 7G,3C | 6G | 6G,5E | 3G | 7G |
| Sugarbeets | 6G,3C | 7G,5H | 8G,8C | 9G,9C | 8G,8C | 10C | 9G,9C | 10C | 0 | 7G,5H | 10C | 8G,7C |
| Corn | 2G | 0 | 6G,3H | 5G,3H | 9G,3C | 6G,5H | 9G,5C | 10C | 0 | 5G,3C | 7G,3H | 8G |
| Mustard | 9G,8C | 9G,9C | 10C | 10C | 10C | 10C | 10C | 10C | 4G | 8G,8C | 8G,8C | 10C |
| Cocklebur | 7G | 7G,3H | 7G | 7G,5H | 8G,5H | 7G,5H | 8G,5H | 8G,5H | — | 3G | 7G,3H | 8G,5H |
| Pigweed | 6G,5C | 10C | 10C | 10C | 10C | 8G,8C | 8G,9C | 10C | 0 | 5G | 9G,9C | 10E |
| Nutsedge | 9G | 7G | 10E | 8G | 6G | 0 | 6G | 5G | 0 | 0 | 5G | 6G |
| Cotton | 0 | 3G | 4H | 6G,5H | 8G,5H | 8G,5H | 8G,5H | 9G,5H | 0 | 5H | 6G,5H | 8G,5H |
| Morninglory | 7G | 3G | 7G | 6G | 8G | 8G,5H | 8G | 9G,8C | 0 | 5H | 7G,5H | 8G,3C |
| Cessia | 0 | 5G | 8G,3C | 8G | 9G,5C | 7G,3H | 9G,8C | 9G,7C | 0 | 0 | 7G,5C | 9G |
| Teaweed | 3G | 7G | 6G,3C | 8G | 7G,2C | 5G,5H | 8G,2C | 7G,5H | 0 | 0 | 0 | 4G,3H |
| Velvetleaf | 7G,5H | 4G,5H | 8G,5H | 8G,5E | 8G,7C | 7G,5H | 8G,7C | 8G,6C | 0 | 4G | 6G,5H | 8G,5C |
| Jimsonweed | 4G | 0 | 5G | 0 | 5G,3C | 8G | 7G,5C | 8G | 0 | 0 | 4G,3C | 7G,4C |
| Soybean | 0 | 1C | 3G,2H | 5G,2C | 0 | 0 | 3G,2H | 5G,5H | 0 | 0 | 4G,3H | 8G,5H |
| Rice | 8G,9C | 10E | 8G,9C | 10C | 8G,8C | 7G,3H | 10E | 10E | 2G | 6G,3C | 5G | 7G,8C |
| Wheat | 2G | 2G | 2G | 3G | 4G | 0 | 5G | 5G | 0 | 4G | 0 | 5G |

| | Compound No. | | | | | |
|---|---|---|---|---|---|---|
| | 12 | | | | 6 | |
| kg/ha | 0.03 | 0.06 | 0.12 | 0.25 | 0.03 | 0.12 |
| Crabgrass | 0 | 3G | 5G | 7G | 2G | 7G |
| Barnyardgrass | 6G | 5G | 8G,4C | 8G,3C | 5G | 7G,2C |
| Sorghum | 9C,9C | 9G,9C | 10C | 10C | 9G,8C | 10C |
| Wild Oats | 9G,9C | 9G,4C | 6G,3H | 6G,3H | 2G | 6G,2H |
| Johnsongrass | 7G,3H | 7G,3H | 8G,3H | 8G,5H | 7G,3H | 8G,3H |
| Dallisgrass | 0 | — | 0 | — | 0 | 4G |
| Giant Foxtail | 0 | 0 | 4G | 5G,3C | 0 | 4G |
| Ky. Bluegrass | 5G | 5G | 7G,3C | 7G,5C | 5G | 6G |
| Cheatgrass | 0 | 5G,5C | 6G,3C | 4G,3C | 3G | 7G,3C |
| Sugarbeets | 8G,7C | 10C | 8G,8C | 10C | 10C | 8G,8C |
| Corn | 7G,3H | 7G,5H | 7G,3H | 7G,5H | 7G,5H | 8G,4C |
| Mustard | 10C | 9G,9C | 10C | 10C | 6G | 7G,2C |
| Cocklebur | 7G,3H | 6G,3H | 8G,5H | 8G,5H | 6G,3H | 7G,5H |
| Pigweed | 9G,9C | 9G,9C | 10E | 9G,9C | 8G,7C | 10C |
| Nutsedge | 6G | 3G | 6G | 6G | 6G | 6G |
| Cotton | 7G,5H | 8G,5H | 8G,5H | 9G,5H | 7G,5H | 8G,5H |
| Morningglory | 8G | 8G,7C | 9G,8C | 9G,3C | 6G,5H | 8G |
| Cassia | 7G,3C | 7G,3H | 8G,5C | 8G,7C | 7G,3C | 8G,5C |
| Teaweed | 5G,5H | 3H | 6G,5H | 8G,5H | 0 | 4G,3H |
| Velvetleaf | 6G,5H | 6G,5H | 8G,5C | 9G,9C | 4G,3H | 7G,5H |
| Jimsonweed | 2G | 5G | 5G | 7G | 0 | 7G,5C |
| Soybean | 0 | 2G | 2G | 2G | 0 | 6G,3H |
| Rice | 5G,3C | 7G,3H | 9G,9C | 9G,9E | 6G,3C | 7G,8C |
| Wheat | 0 | 3G | 4G | 4G | 0 | 3G,2C |

TEST C

The high herbicidal activity and selective properties of several of the compounds from within the scope of the invention is evident from the results obtained in this test. The experiment concerned pre-emergence applications on soil. The containers used were 25 cm diameter plastic pots filled with Fallsington silt loam. One set of pots was planted to weeds, the seeds of which were uniformly mixed with th top 1.2 cm layer of soil. The species selected were: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*), and pigweed (*Amaranthus retroflexus*). Another set of pots was planted to the following crops with from one to four species per pot: corn (planting dept 3.7 cm), cotton, soybeans, sunflower, Clinton oats, wheat, Black Velentine beans, rice, sorghum, peas, flax, and peanuts (all at 2.5 cm depth), cucumbers, cabbage, alfalfa, safflower, sugarbeets, tomato, spinach, barley, and Kentucky bluegrass (all at 1.2 cm depth). Immediately after planting, the test chemicals were applied to the soil surfaces dissolved in a non-phytotoxic solvent. In the case of tobacco, a solution containing the test chemical was drenched on the surface of the soil surrounding newly transplanted tobacco seedlings. One pot from the weed phase and one of each of the crop species were left untreated for the purpose of comparison. The treated and untreated pots were promptly watered with approximately 4 mm of simulated rainfall and then held in a greenhouse for several weeks. Visual weed and crop response ratings were made 28 days after treatment utilizing the rating system as described above. The data are given in Table C. The data clearly indicate that compounds from within the scope of the present invention have utility for selective pre-emergence weed control in crops such as soybeans, alfalfa, wheat, oats, barley, cucumber, and tomato. In the case of at least one compound, weed control is obtained by applying the chemical in the form of a drench on the soil around newly-transplanted tobacco seedlings.

TEST D

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). In the case of compound No. 13, the following additional species were included: sunflower, mustard, sugarbeets and bushbean. Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data

TABLE C

PRE-EMERGENCE ON FALLSINGTON SILT LOAM

| kg/ha | Compound No. 3 | | | | Compound No. 11 | | | | Compound No. 12 | | | |
|---|---|---|---|---|---|---|---|---|---|---|---|---|
| | 1/64 | 1/32 | 1/16 | 1/8 | 1/128 | 1/64 | 1/32 | 1/16 | 1/128 | 1/64 | 1/32 | 1/16 |
| Corn | | | | 7G,5H | | | | 8G,8C | | | | 8G,8C |
| Cotton | | | | 7G,5H | | | | 7G,5H | | | | 8G,5H |
| Soybean | | | | 7G,5H | | | | 0 | | | | 0 |
| Peanut | | | | 7G,5H | | | | — | | | | — |
| Sunflower | | | | 8G,5H | | | | 9G,8C | | | | 9G,8C |
| Oats | | | | 4G | | | | 6G,2C | | | | 5G,2C |
| Wheat | | | | 2G | | | | 5G | | | | 4G |
| Sorghum | | | | 10E | | | | 9G,9C | | | | 8G,8C |
| Sugarbeet | | | | 8G,7C | | | | 9G,9C | | | | 9G,9C |
| Pea | | | | 9G,9C | | | | 10E | | | | 10E |
| Flax | | | | 9G,9C | | | | 7G,5E | | | | 8G,8C |
| Alfalfa | | | | 8G,8C | | | | 7G,3C | | | | 4G |
| Bean | | | | 7G,5H | | | | 8G,5H | | | | 5G,3H |
| Spinach | | | | 9G,8C | | | | 8G,8C | | | | 8G,9C |
| Cabbage | | | | 9G,9C | | | | 8G,7C | | | | 8G,6C |
| Tomato | | | | 4G | | | | 7G,5H | | | | 2G |
| Rice | | | | 10E | | | | 7G,7C | | | | 9G,8C |
| Safflower | | | | 8G,6C | | | | 8G,3C | | | | 8G,3C |
| Cucumber | | | | 9G,5H | | | | 9G | | | | 5G |
| Ky. Bluegrass | | | | 8G,9C | | | | 7G | | | | 6G |
| Barley | | | | 8G,6C | | | | 3G | | | | 3G |
| Tobacco | | | | 0 | | | | — | | | | — |
| Broadleaves | 2G,3C | 4G,4C | 5G,4C | | 5G,3C | 7G,7C | 8G,7C | | 3G | 2G | 5G,3C | |
| Grasses | 5G,2C | 6G,3C | 7G,5C | | 2G | 3G | 4G | | 3G | 0 | 3G | | are pesented in Table D. Several of the compounds tested by this procedure are useful for the post-emergence control of weeds in wheat, corn and soybeans.

TABLE D

Over-the-Top Soil/Foliage Treatment

| kg/ha | Compound No. 7 | | | | Compound No. 8 | | | Compound No. 9 | | |
|---|---|---|---|---|---|---|---|---|---|---|
| | 0.016 | 0.031 | 0.063 | 0.125 | 0.016 | 0.031 | 0.125 | 0.016 | 0.031 | 0.063 |
| Soybeans | 0 | 9G,4C | 4G,2C | 10G,7C | 8G,3C | 10G,7C | 10G,7C | 10G,7C | 10G,6C | 10G,7C |
| Velvetleaf | 8G,3C | 9G,4C | 8G,3C | 10G,7C | 8G,3C | 10G,6C | 10G,7C | 8G | 10G,7C | 10G,3C |
| Sesbania | 5G,3C | 7G,3C | 7G,3C | 10G,5C | 9G,5C | 9G,5C | 10G,8C | 10G,8C | 10G,8C | 10G,8C |
| Cassia | 4G,2C | 9G,3C | 6G,2C | 10G,6C | 5G,3C | 10G,4C | 10G,6C | 9G,5C | 10G,7C | 10G,7C |
| Cotton | 3G,2C | 7G,3C | 5G,3C | 9G,6C | 8G,4C | 9G,4C | 10G,6C | 7G,3C | 9G,3C | 10G,6C |
| Morningglory | 9G,4C | 10G,7C | 10G,7C | 10G,8C | 9G,5C | 10G,8C | 10G,6C | 10G,7C | 10G,7C | 10G,7C |
| Alfalfa | 2C,3G | 5G,2C | 2C,3G | 8G,5C | 5G,3C | 7G,4C | 8G,6C | 8G,4C | 6G,2C | 8G,3C |
| Jimsonweed | 1C | 3G,2C | 4G,2C | 7G,3C | 1G,1C | 7G,3C | 9G,4C | 0 | 1G | 4G,1C |
| Cocklebur | 1C | 10G,6C | 6G,3C | 10G,7C | 6G,2C | 9G,3C | 10G,7C | 9G,6C | 10G,9C | 10G,7C |
| Corn | 1H | 0 | 2G,1C | 1G,2H | 4G,4H | 1H | 6G,3C | 3G,2H | 0 | 4G,4H |
| Crabgrass | 1G | 0 | 1G | 4G | 2G | 4G | 6G | 1G | 7G | 2G |
| Rice | 7G,2C | 8G,3C | 8G,5C | 9G,6C | 8G,3C | 8G,3C | 8G,5C | 8G,5C | 9G,6C | 8G,7C |
| Nutsedge | 2G | 3G,3C | 2G,1C | 6G,2C | 4G,1C | 5G,1C | 7G | 5G,2C | 6G,2C | 7G,3C |
| Barnyardgrass | 1C,6G | 7G,3C | 1C,6G | 10C | 6G,2C | 8G,5C | 9G,7C | 6G,3C | 10C | 8G,5C |
| Wheat | 0 | 1G | 2G | 3G | 1G | 2G | 2G | 1G | 2G | 4G |
| Giant Foxtail | — | 7G,2C | 2G | 9C | 5G | 7G,3C | 8G,3C | 5G,1C | 8G,3C | 6G,1C |
| Wild Oats | 6G | 7G,2C | 7G | 7G,10C | 7G | 8G | 8G | 5G | 7G,1C | 7G,2C |

TABLE D-continued

Over-the-Top Soil/Foliage Treatment

| Sorghum | 8G,1C | 9G,3C | 8G,4C | 10C | 8G,1U | 9C | 9C | 9G,3C | 10G,8C | 9G,4C |
|---|---|---|---|---|---|---|---|---|---|---|
| | Compound No. 9 | | Compound No. 10 | | | | | Compound No. 11 | | |
| kg/ha | 0.125 | | 0.016 | 0.031 | 0.063 | 0.125 | 0.016 | 0.031 | 0.125 | |
| Soybeans | 10G,8C | | 0 | 0 | 1G,1C | 5G,3C | 1C | 10G,7C | 10G,7C | |
| Velvetleaf | 10G,9C | | 8G,3C | 6C,3C | 8G,3C | 7G,3C | 8G,3C | 10G,8C | 10G,9C | |
| Sesbania | 10G,9C | | 2C | 7G,3C | 4G,3C | 7G,3C | 10G,6C | 10G,7C | 10G,9C | |
| Cassia | 10G,7C | | 2C | 10G,8C | 4G,3C | 7G,3C | 8G,3C | 7G,4C | 9G,5C | |
| Cotton | 10G,7C | | 3G,2C | 7G,3C | 5G,3C | 8G,3C | 6G,3C | 10G,7C | 10G,7C | |
| Morningglory | 10G,8C | | 8G,3C | 10G,4C | 9G,3C | 10G,6C | 10G,4C | 10G,8C | 10G,9C | |
| Alfalfa | 7G,4C | | 2C | 7G,4C | 3G,2C | 8G,4C | 7G,4C | 7G,7C | 9G,8C | |
| Jimsonweed | 1G | | 5G,2C | 7G,3C | 5G,2C | 7G,3C | 3G,1C | 9G,7C | 10G,7C | |
| Cocklebur | 10G,9C | | 1C | 9G,3C | 3G,2C | 10G,5C | 10G,7C | 10G,8C | 10G,8C | |
| Corn | 1G,1H | | 2H,1C | 6G,5H | 3G,2H | 7G,3U | 9G,4C | 10G,6C | 10G,6C | |
| Crabgrass | 9G,5C | | 1G | 3G,1C | 1G | 6G,2C | 0 | 8G,5C | 8G,5C | |
| Rice | 10G,7C | | 7G,1C | 9G,3C | 7G,1C | 10G,7C | 6G,2C | 8G,6C | 8G,6C | |
| Nutsedge | 8G | | 2G | 0 | 2G,1C | 0 | 1G | 1G | 2G | |
| Barnyardgrass | 10C | | 1G,1C | 6G | 1G,1C | 8G,2C | 6G,1C | 8G,3C | 10C | |
| Wheat | 2G | | 0 | 1G | 0 | 1G | 0 | 0 | 1G | |
| Giant Foxtail | 8G,4C | | 1G | 6G,2C | 3G,1C | 7G,3C | 3G | — | 8G,3C | |
| Wild Oats | 8G,2C | | 2G | 7G | 2G | 7G | 1G | 8G,2C | 8G,1C | |
| Sorghum | 9C | | 8G,1C | 9G,3C | 8G,2U | 9C | 9G,2C | 9C | 9C | |

| | Compound No. 12 | | | Compound No. 2 | | | Compound No. 3 | | | |
|---|---|---|---|---|---|---|---|---|---|---|
| kg/ha | 0.016 | 0.031 | 0.125 | 0.016 | 0.031 | 0.125 | 0.016 | 0.031 | 0.063 | 0.125 |
| Soybeans | 0 | 7G,3C | 10G,7C | 5G,3C | 9G,7C | 10G,7C | 6G,3C | 10G,7C | 9G,3C | 9G,5C |
| Velvetleaf | 7G,3C | 10G,8C | 10G,8C | 6G,3C | 9G,5C | 10G,9C | 5G,3C | 10G,7C | 8G,3C | 10G,9C |
| Sesbania | 6G,3C | 10G,8C | 10G,8C | 5G,3C | 9G,4C | 10G,8C | 5G,3C | 10G,8C | 7G,3C | 10G,8C |
| Cassia | 4G,3C | 10G,7C | 10G,4C | 3G,2C | 10G,6C | 10G,8C | 4G,3C | 10G,8C | 5G,3C | 10G,8C |
| Cotton | 4G,3C | 10G,4C | 10G,7C | 3G,2C | 7G,4C | 10G,7C | 3C | 8G,5C | 7G,2C | 8G,7C |
| Morningglory | 9G,3C | 10G,7C | 10G,9C | 6G,2C | 10G,5C | 10G,9C | 6G,3C | 10G,9C | 7G,3C | 10G,8C |
| Alfalfa | 0 | 2G | 5G,1C | 4G,2C | 7G,3C | 7G,4C | 7G,3C | 8G,5C | 7G,3C | 8G,5C |
| Jimsonweed | 2G,1C | 0 | 6G,1C | 2G,1C | 5G,2C | 7G,3C | 4G,1C | 0 | 3G,1C | 5G,1C |
| Cocklebur | 1C | 10G,8C | 10G,8C | 5G,2C | 9G,4C | 10G,7C | 5G,2C | 10G,7C | 7G,4C | 10G,7C |
| Corn | 9G,2C | 9G,3U | 10G,8U | 0 | 2G | 3G | 0 | 0 | 2G,1C | 0 |
| Crabgrass | 0 | 3G | 7G,4C | 1G,1C | 1G | 3G | 1G | 0 | 3G | 6G,1C |
| Rice | 4G | 7G,2C | 8G,3C | 4G | 5G,2C | 7G,3C | 5G,1C | 3G,3C | 8G,1C | 5G,4C |
| Nutsedge | 4G | 2G | 3G | 3G | 6G,1C | 7G,1C | 2G | 7G,3C | 3G | 6G |
| Barnyardgrass | 3G | 7G,3C | 8G,4C | 5G,1C | 8G,3C | 9G,4C | 4G,1C | 8G | 6G,1C | 8G,3C |
| Wheat | 0 | 0 | 0 | 0 | 3G | 4G | 0 | 0 | 0 | 0 |
| Giant Foxtail | 0 | 3G,1C | 6G,2C | 0 | 6G,2C | 7G,1C | 3G | 7G,3C | 3G | 8G,1C |
| Wild Oats | 0 | 3G | 7G | 0 | 4G | 7G,2C | 0 | 4G,1C | 5G | 3G |
| Sorghum | 8G | 9G,7C | 9C | 8G,1C | 10G | 10G,2U | 9G | 7G,3C | 9G,2U | 8G,3C |

| | Compound No. 5 | | | Compound No. 6 | | | Compound No. 13 | | | |
|---|---|---|---|---|---|---|---|---|---|---|
| hg/ha | 0.016 | 0.031 | 0.125 | 0.016 | 0.031 | 0.125 | 0.016 | 0.031 | 0.062 | 0.125 |
| Soybeans | 6G,3C | 9G,5C | 10G,7C | 7G,3C | 10G,7C | 10G,8C | 3G | 3G | 7G,1C | 7G,2C |
| Velvetleaf | 8G,3C | 9G,4C | 10G,7C | 7G,3C | 9G,4C | 10G,7C | 7G,2C | 7G,2C | 9G,3C | 9G,4C |
| Sesbania | 5G,3C | 9G,5C | 10G,7C | 4G,3C | 8G,4C | 10G,8C | 7G,3C | 8G,4C | 9G,4C | 9G,4C |
| Cassia | 4G,3C | 10G,8C | 10G,8C | 4G,3C | 10G,7C | 10G,8C | 8G,4C | 9G,5C | 9G,6C | 10G,5C |
| Cotton | 5G,2C | 9G,2C | 10G,6C | 6G,3C | 9G,3C | 10G,6C | 1C | 4G,3C | 7G,3C | 7G,4C |
| Morningglory | 7G,3C | 10G,7C | 10G,7C | 8G,3C | 10G,7C | 10G,8C | 8G,4C | 8G,4C | 9G,5C | 9G,5C |
| Alfalfa | 4G,3C | 7G,3C | 7G,4C | 4G,2C | 6G,2C | 8G,4C | 2C | 4G,2C | 5G,2C | 6G,2C |
| Jimsonweed | 5G,2C | 6G,3C | 8G,3C | 2G,2C | 7G,1C | 8G,2C | 3G | — | 6G | 8G |
| Cocklebur | 7G,3C | 9G,4C | 10G,7C | 1C | 10G,6C | 10G,8C | 4G,3C | 6G,3C | 7G,4C | 10G,3C |
| Corn | 9G,3C | 8G,6H | 8G,8H | 9G,3C | 8G,4C | 9G,4C | 4H | 8G,4H | 9G,4C | 9G,3U |
| Crabgrass | 0 | 2G | 3G | 0 | 1G | 6G | 0 | 0 | 2G | 2G |
| Rice | 4G | 5G,2C | 7G,3C | 4G,1C | 4G,2C | 7G,3C | 2G | 2G | 5G | 6G |
| Nutsedge | 1G | 3G | 4G | 0 | 2G | 3G | 0 | 1G | 2G | 5G |
| Barnyardgrass | 6G,1C | 8G,4C | 9G,4C | 0 | 8G,2C | 8G,4C | 0 | 3G | 5G,3C | 5G,3C |
| Wheat | 0 | 3G | 3G | 0 | 0 | 2G | 0 | 1G | 2G | 3G |
| Giant Foxtail | 3G | 4G | 6G | 0 | 7G,1C | 7G | 2G | 2G | 4G | 4G |
| Wild Oats | 1G | 2G | 3G,1C | 0 | 2G | 3G,1C | 0 | 0 | 2G | 2G |
| Sorghum | 9G,2C | 9G,3U | 9G,3U | 8G,1C | 9G,3U | 9G,3U | 4G | 6G | 7G | 7G,3C |
| Sunflower | | | | | | | 0 | 9G,7C | 10G,8C | 10G,8C |
| Mustard | | | | | | | 9G,3C | 9G,3C | 9G,3C | 9G,3C |
| Sugarbeets | | | | | | | 1C | 2C | 4G,3C | 5G,3C |
| Bushbean | | | | | | | 0 | 0 | 0 | 0 |

TEST E

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pennsylvanicum*), jimhill or tumble mustard (*Sisymbrium altissium*) kochia (*Kochia scoparia*), shepard's purse (*Capsella bursa-pastoris*), *Matricaria inodora*, black nightshade (*Solanum migrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent-alone control were included for comparison. All treatments were maintained in the greenhouse for 20 days at which time the treatments were compared to the controls and the effects visually rated in accordance with the previously described rating system. The recorded data are presented in Table E.

Several of the compounds included in this table provide excellent weed control at very low rates of application, yet are tolerated with little or no injury by wheat and barley at rates which are multiples of those required for weed control. This observation applies to both pre- and post-emergence treatments.

TABLE E

|  | Compound No. 2 | | | | Compound No. 3 | | | | | | | |
|---|---|---|---|---|---|---|---|---|---|---|---|---|
| TEST PLANT kg/ha | 0.02 | 0.06 | 0.02 | 0.06 | 0.02 | 0.06 | 0.02 | 0.06 | 0.02 | 0.06 | 0.02 | 0.06 |
|  | Pre-Emergence | | Post-Emergence | | Pre-Emegence | | Post-Emergence | | Pre-Emergence | | Post-Emergence | |
| Wheat | 0 | 0 | 0 | 1G | 0 | 1G | 0 | 1C,1G | 0 | 2C,1G | 0 | 1C,2G |
| Barley | 2C,4G | 5C,6G | 1G | 4C,6G | 3G | 3C,7G | 6C,5G | 7C,7G | 5G | 3C,8G | 5C,7G | 8C,7G |
| Wild Oats | 3C,2G | 5C,5G | 1G | 6C,6G | 3G | 5C,7G | 1C,2G | 5C,6G | 1C,5G | 5C,7G | 4C,5G | 6C,6G |
| Downy Brome | 7C,4G | 8C,7G | 2C,2G | 10C | 7C,7G | 10C | 7C 7G | 10C | 6C,7G | 10C | 7C,8G | 10C |
| Cheatgrass | 6C,5G | 10C | 3C,5G | 8C,7G | 10C | 10C | 9C,8G | 10C | 9C,8G | 10C | 10C | 10C |
| Blackgrass | 7C,7G | 10C | 5C,5G | 7C,7G | 10C | 10C | 10C | 10C | 10C | 10C | 10C | 10C |
| Annual Bluegrass | 3G | 6C,7G | 4G | 6C,7G | 7C,7G | 7C,8G | 7C,6G | 9C,7G | 5C,6G | 9C,9G | 9C | 10C |
| Green Foxtail | 4C,2G | 6C,6G | 2G | 6C,6G | 7C,6G | 7C,8G | 3C,6G | 7C,7G | 3C,4G | 9C,9G | 6C,6G | 7C,6G |
| Quackgrass | 3G | 4C,6G | 2C,4G | 3C,7G | 7G | 5C,8G | 1C,6G | 5C,7G | 5C,6G | 9C,8G | 3C,6G | 8C,7G |
| Italian Ryegrass | 2G | 2C,5G | 3G | 6G | 6G | 2C,7G | 2G | 2C,4G | 3G | 4C,6G | 1C,3G | 4C,5G |
| Ripgut Brome | 2C,4G | 6C,7G | 1G | 2C,4G | 3C,7G | 4C,8G | 1C,2G | 3C,5G | 3G | 5C,7G | 3C,4G | 6C,7G |
| Russian Thistle | 9C,8G | 9C,9G | 2C,2G | 5C,7G | 4C,5G | 7C,7G | 2C,3G | 10C | — | — | — | — |
| Tansy Mustard | 10C | 10C | 10C | 10C | 10C | 10C | 10C | 10C | 10C | 10C | 10C | 10C |
| Smartweed | — | — | — | — | — | — | — | — | — | — | — | — |
| Jimhill Mustard | 10C | 10C | 10C | 10C | 10C | 10C | 10C | 10C | 10C | 10C | 10C | 10C |
| Kochia | 4G | 2C,5G | 7C,6G | 7C,7G | 6G | 3C,7G | 2G | 2C,4G | 2C,5G | 5C,6G | 0 | 2G |
| Shepherd's Purse | 10C | 10C | 7C,7G | 8C,7G | 7C,7G | 9C,9G | 9C,8G | 10C | 10C | 10C | 10C | 10C |
| False Chamomile | 4C,6G | 7C,8G | 5C,5G | 7C,7G | 9C,9G | 9C,9G | 9C,9G | 10C | 8C,8G | 9C,9G | 10C | 10C |
| Black Nightshade | 1C,7G | 2C,8G | 3G | 1C,5G | 7C,8G | 7C,8G | 7C,8G | 10C | 3C,6G | 5C,6G | 9C,8G | 10C |
| Yellow Rocket | 9C,9G | 9C,9G | 5C,6G | 10C | 9C,9G | 9C,9G | 10C | 10C | 9C,9G | 10C | 10C | 10C |
| Wild Mustard | 8C,8G | 9C,9G | 10C | 10C | 7C,8G | 9C,9G | 10C | 10C | 9C,8G | 9C,9G | 10C | 10C |
| Wild Buckwheat | 3G | 4C,4G | 2C,2G | 5C,5G | 3C,4G | 4C,5G | 1C,2G | 4C,4G | 2C,4G | 5C,6G | 3C,4G | 4C,4G |
| *Matricaria inodora* | | | | | | | | | | | | |

|  | Compound No. 3 | | | | | | | | | | | |
|---|---|---|---|---|---|---|---|---|---|---|---|---|
| TEST PLANT kg/ha | 0.02 | 0.06 | 0.02 | 0.06 | 0.002 | 0.02 | 0.12 | 0.002 | 0.02 | 0.12 | 0.002 | 0.02 | 0.12* |
|  | Pre-Emergence | | Post-Emergence | | Pre-Emergence | | | Post-Emergence | | | Pre-Emergence | | |
| Wheat | 0 | 1C,1G | 0 | 0 | 0 | 0 | 0 | 0 | 1G | 3G | 0 | 0 | 0 |
| Barley | 5G | 6C,7G | 4C,6G | 8C,8G | 0 | 0 | 3G | 0 | 3G | 6G | 0 | 0 | 3G |
| Wild Oats | 5G | 4C,6G | 1G | 1C,2G | 0 | 0 | 1C,3G | 0 | 1G | 1C,5G | 0 | 0 | 3G |
| Downy Brome | 7C,7G | 10C | 6C,5G | 7C,8G | 1G | 2C,3G | 3C,5G | 2G | 4C,5G | 6C,5G | 3G | 3G | 4C,6G |
| Cheatgrass | 10C | 10C | 8C,7G | 8C,8G | 2G | 6C,7G | 7C,8G | 5C,6G | 7C,6G | 7C,6G | 2C,4G | 4C,6G | 7C,7G |
| Blackgrass | 10C | 10C | 9C,8G | 10C | 1C,4G | 7C,7G | 10C | 6C,6G | 10C | 10C | 1C,6G | 5C,6G | 10C |
| Annual Bluegrass | 7C,8G | 7C,8G | 4C,6G | 7C,8G | 2G | 1C,4G | 4C,6G | 1C,4G | 7C,7G | 8C,8G | 2G | 1C,3G | 4C,6G |
| Green Foxtail | 5C,6G | 8C,8G | 2C,2G | 3C,3G | 0 | 1C,1G | 3C,6G | 0 | 2C,3G | 8C,8G | 0 | 3C,4G | 4C,7G |
| Quackgrass | 7C,6G | 9C,8G | 5C,6G | 5C,7G | 0 | 2G | 2C,6G | 0 | 2G | 1C,3G | 1G | 3G | 2C,6G |
| Italian Ryegrass | 3G | 1C,7C | 1G | 3G | 0 | 1G | 1C,4G | 0 | 0 | 2G | 0 | 2G | 1C,3G |
| Ripgut Brome | 2C,6G | 7C,7G | 2C,5G | 3C,6G | 0 | 0 | 5G | 0 | 2G | 1C,5G | 0 | 2G | 3G |
| Russian Thistle | 0 | 2C,2G | 10C | 10C | 0 | 0 | 1C,2G | 2C,2G | 3C,4G | 7C,7G | 0 | 0 | 1C,2G |
| Tansy Mustard | 9C,9G | 10C | 10C | 10C | 8C,8G | 8C,8G | 9C,9G | 8C,7G | 10C | 10C | 5C,6G | 9C,9G | 9C,9G |
| Smartweed | — | — | — | — | | | | | | | | | |
| Jimhill Mustard | 9C,9G | 10C | 10C | 10C | 2C,3G | 7C,8G | 9C,9G | 10C | 10C | 10C | 7C,7G | 9C,8G | 9C,9G |
| Kochia | 5G | 3C,8G | 3C,2G | 2C,4G | 0 | 2G | 3G | 0 | 0 | 1G | 0 | 1G | 2C,3G |
| Shepherd's Purse | 9C,9G | 9C,9G | 8G,7G | 8C,8G | 3C,5G | 9C,9G | 9C,9G | 10C | 9C,8G | 10C | 8C,8G | 9C,9G | 10C |
| False Chamomile | 8C,9G | 9C,9G | 9C,8G | 10C | | | | | | | | | |
| Black Nightshade | 2C,7G | 4C,7G | 5C,6G | 7C,7G | 0 | 1C,3G | 3C,6G | 2C,3G | 2C,4G | 4C,7G | 1C,4G | 3C,5G | 5C,6G |
| Yellow Rocket | 8C,8C | 9C,8G | 10C | 10C | 2C,4G | 3C,8G | 7C,9G | 10C | 10C | 10C | 4C,7G | 7C,8G | 7C,8G |
| Wild Mustard | 8C,8G | 9C,8G | 10C | 10C | 3C,4G | 7C,7G | 8C,8G | 10C | 10C | 10C | 7C,7G | 7C,7G | 8C,8G |
| Wild Buckwheat | 4G | 3C,6G | 1C,5G | 5C,6G | 1C,1G | 2G | 3C,4G | 2C,2G | 3C,4G | 3C,4G | 1G | 1C,1G | 2C,3G |
| *Matricaria inodora* | | | | | 3C,4G | 7C,7G | 7C,8G | 9C,7G | 9C,8G | 10C | 6C,5G | 7C,7G | 8C,8G |

|  | Compound No. 3 | | | Compound No. 5 | | | | | | | | Compound 6 | |
|---|---|---|---|---|---|---|---|---|---|---|---|---|---|
| TEST PLANT kg/ha | 0.002 | 0.02 | 0.12* | 0.02 | 0.06 | 0.02 | 0.06 | 0.02 | 0.06 | 0.02 | 0.06 | 0.02 | 0.06 |
|  | Post-Emergence | | | Pre-Emergence | | Post-Emergence | | Pre-Emergence | | Post-Emergence | | Pre-Emergence | |
| Wheat | 0 | 1G | 2G | 0 | 0 | 0 | 0 | 0 | 1C,1G | 0 | 0 | 0 | 0 |
| Barley | 0 | 2G | 2C,4G | 1G | 3G | 0 | 1C,2G | 0 | 2C,7G | 0 | 2C,5G | 0 | 2G |
| Wild Oats | 0 | 1G | 1G | 0 | 2C,5G | 0 | 2G | 1C,2G | 2C,5G | 0 | 1C,2G | 0 | 3G |
| Downy Brome | 2G | 3G | 4C,5G | 1C,2G | 5C,7G | 0 | 3C,3G | 4G | 4C,7G | 2G | 7C,7G | 2G | 2C,6G |
| Cheatgrass | 4G | 1C,5G | 8C,5G | 2C,6G | 6C,7G | 2G | 7C,8G | 4C,7G | 5C,7G | 2C,3G | 10C | 3G | 4C,7G |
| Blackgrass | 3C,4G | 5C,5G | 10C | 7C,8G | 7C,8G | 7C,5G | 10C | 10C | 7C,8G | 7C,6G | 10C | 3C,4G | 7C,7G |
| Annual Bluegrass | 1C,4G | 5C,6G | 10C | 1C,6G | 7G | 2G | 7C,6C | 6G | 7C | 1C,2G | 9C | 3G | 2C,7G |
| Green Foxtail | 0 | 3G | 6C,6G | 2C,3G | 3C,6G | 0 | 3C,4G | 1G | 3C,4G | 0 | 6C,5G | 1G | 1C,3G |
| Quackgrass | 0 | 3G | 4G | 3G | 5G | 0 | 3C,5G | 0 | 2C,7G | 0 | 2C,4G | 0 | 5G |

TABLE E-continued

| | | | | | | | | | | | | |
|---|---|---|---|---|---|---|---|---|---|---|---|---|
| Italian Ryegrass | 0 | 1G | 1C,3G | 2G | 4G | 0 | 3G | 0 | 2C,7G | 0 | 1C,3G | 0 | 2G |
| Ripgut Brome | 0 | 2G | 2C,4G | 1C,2G | 2C,3G | 0 | 1C,2G | 0 | 3C,3G | 0 | 2C,2G | 0 | 1G |
| Russian Thistle | 0 | 2C,3G | 2C,3G | 3G | 7C,7G | 10C | 10C | — | — | — | — | 2C,3G | 7C,8G |
| Tansy Mustard | 7C,7G | 10C | 10C | 10C | 10C | 10C | 10C | 10C | 10C | 10C | 10C | 10C | 10C |
| Smartweed | — | — | — | — | — | — | — | — | — | — | — | — | — |
| Jimhill Mustard | 10C | 10C | 10C | 8C,9G | 9C,9G | 10C | 10C | 2C,6G | 10C | 10C | 10C | 10C | 10C |
| Kochia | 0 | 1G | 2C,2G | 1C,6G | 5C,7G | 7C,8G | 10C | 2C,4G | 5C,6G | 7C,7G | 10C | 2G | 2C,5G |
| Shepherd's Purse | 10C | 8C,8G | 9C,8G | 8C,8G | 10C | 10C | 10C | 1C,5G | 10C | 10C | 10C | 8C,9G | 9C,9G |
| False Chamomile | | | | 2G | 6C,7G | 7C,7G | 10C | 3G | 5C,8G | 7C,6G | 10C | 2G | 5C,6G |
| Black Nightshade | 2C,2G | 3C,3G | 4C,5G | 6G | 6C,7G | 6C,7G | 10C | 1C,2G | 4C,7G | 4C,6G | 10C | 1C,6G | 5C,7G |
| Yellow Rocket | 7C,7G | 8C,7G | 8C,8G | 8C,8G | 9C,9G | 8C,8G | 10C | 7G | 10C | 10C | 10C | 7G | 4C,7G |
| Wild Mustard | 10C | 10C | 10C | 4C,7G | 9C,9C | 10C | 10C | 9C,9G | 9C,9G | 10C | 10C | 5G | 8C,8G |
| Wild Buckheat | 1C,2G | 2C,3G | 3C,4G | 3C,6G | 5C,7G | 4C,5G | 10C | 3C,5G | 5C,6G | 6C,6G | 10C | 2G | 2C,3G |
| Matricaria inodora | 6C,5G | 8C,8G | 9C,8G | | | | | | | | | | |

| | Compound No. 6 | | | | | | Compound No. 8 | | | | Compound No. 9 | |
|---|---|---|---|---|---|---|---|---|---|---|---|---|
| TEST PLANT kg/ha | 0.02 | 0.06 | 0.02 | 0.06 | 0.02 | 0.06 | 0.02 | 0.06 | 0.02 | 0.06 | 0.02 | 0.06 |
| | Post-Emergence | | Pre-Emergence | | Post-Emergence | | Pre-Emergence | | Post-Emergence | | Pre-Emergence | |
| Wheat | 0 | 0 | 0 | 1C,1G | 0 | 0 | 1C,1G | 3C,1G | 2G | 2C,3G | 1C,2G | 2C,2G |
| Barley | 0 | 1G | 0 | 2C,3G | 2G | 1C,3G | 2C,6G | 3C,7G | 6C,6G | 7C,8G | 3C,7G | 6C,8G |
| Wild Oats | 0 | 1G | 0 | 3C,4G | 0 | 2G | 6C,6G | 6C,6G | 4C,5G | 8C,8G | 3C,7G | 6C,7G |
| Downy Brome | 1C,2G | 3C,5G | 2G | 7C,7G | 2G | 3C,4G | 8C,8G | 9C,9G | 7C,8G | 10C | 8C,7G | 10C |
| Cheatgrass | 1C,3G | 5C,7G | 1C,7G | 7C,8G | 1C,3G | 10C | 10C | 10C | 8C,8G | 10C | 10C | 10C |
| Blackgrass | 5C,6G | 7C,8G | 3C,7G | 10C | 3C,4G | 8C,7G | 10C | 10C | 8C,8G | 10C | 10C | 10C |
| Annual Bluegrass | 3G | 4G | 6G | 7G | 1G | 2C,2G | 8C,7G | 8C,8G | 7C,7G | 9C,8G | 7C,7G | 9C,8G |
| Green Foxtail | 0 | 1C,2G | 2G | 4C,6G | 1C,2G | 2C,3G | 7C,6G | 7C,8G | 4C,3G | 7C,6G | 7C,7G | 7C,8G |
| Quackgrass | 0 | 2C,3G | 2C,3G | 3C,6G | 1G | 1C,2G | 4C,6G | 8C,8G | 7C,7G | 7C,7G | 8G | 8C,8G |
| Italian Ryegrass | 0 | 0 | 1C,2G | 2C,3G | 1G | 1C,2G | 3C,6G | 5C,8G | 4C,6G | 5C,7G | 2C,8G | 7C,8G |
| Ripgut Brome | 0 | 0 | 1G | 1C,2G | 2G | 1C,3G | 5C,7G | 6C,8G | 3C,5G | 5C,7G | 8G | 7C,8G |
| Russian Thistle | 10C | 10C | — | — | — | — | 2C,4G | 10C | 8C,7G | 9C,8G | 2G | 5C,5G |
| Tansy Mustard | 10C | 10C | 10C | 10C | 10C | 10C | 10C | 10C | 10C | 10C | 10C | 10C |
| Smartweed | — | — | — | — | — | — | — | — | — | — | — | — |
| Jimhill Mustard | 10C | 10C | 3C,6G | 10C | 8C | 10C | 9C,9G | 10C | 10C | 10C | 10C | 10C |
| Kochia | 3C,4G | 4C,7G | 2G | 2C,4G | 0 | 5C,6G | 5C,6G | 5C,7G | 4G | 4C,5G | 7G | 3C,8G |
| Shepherd's Purse | 7C,7G | 10C | 5C,6G | 10C | 10C | 10C | 9C,9G | 10C | 9C,7G | 10C | 10C | 10C |
| False Chamomile | 5C,6G | 10C | 1G | 7C,8G | 8C,8G | 9C,8G | 7C,8G | 8C,9G | 9C,8G | 10C | 7C,8G | 9C,9G |
| Black Nightshade | 2C,6G | 9C,8C | 1C,2G | 2C,4G | 2C,4G | 7C,8G | 2C,7G | 3C,8G | 5G | 6G | 5C,8G | 6C,8G |
| Yellow Rocket | 0 | 2G | 6G | 7G | 0 | 2C,4G | 9C,9G | 9C,9G | 9C,7G | 9C,8G | 9C,9G | 10C |
| Wild Mustard | 2C,3G | 7C,6G | 2C,5G | 3C,6G | 8C,8G | 7C,6G | 9C,9G | 9C,9G | 10C | 10C | 9C,9G | 9C,9G |
| Wild Buckwheat | 1C,2G | 4C,5G | 2C,4G | 2C,5G | 2C,2G | 5C,5G | 2C,4G | 5C,6G | 7C,5G | 7C,7G | 4C,6G | 5C,7G |
| Matricaria inodora | | | | | | | | | | | | |

| | Compound No. 9 | | Compound No. 11 | | | | Compound No. 12 | | | |
|---|---|---|---|---|---|---|---|---|---|---|
| TEST PLANT kg/ha | 0.02 | 0.06 | 0.02 | 0.06 | 0.02 | 0.06 | 0.02 | 0.06 | 0.02 | 0.06 |
| | Post-Emergence | | Pre-Emergence | | Post-Emergence | | Pre-Emergence | | Post-Emergence | |
| Wheat | 1C,2G | 2C,2G | 0 | 0 | 0 | 1C,4G | 0 | 0 | 0 | 0 |
| Barley | 8C,7G | 8C,8G | 2C,2G | 2C,4G | 0 | 3C,3G | 2G | 3G | 0 | 2G |
| Wild Oats | 3C,4G | 5C,6G | 2C,3G | 3C,6G | 0 | 6C,7G | 3G | 6G | 0 | 1C,3G |
| Downy Brome | 8C,8G | 10C | 4C,6G | 7C,7G | 2C,2G | 10C | 2C,5G | 3C,6G | 2G | 5C,4G |
| Cheatgrass | 10C | 10C | 3C,7G | 10C | 2C,6G | 9C,8G | 1C,7G | 7C,7G | 3G | 2C,6G |
| Blackgrass | 10C | 10C | 7C,8G | 10C | 3C,7G | 10C | 5C,7G | 8C,8G | 2C,2G | 5C,7G |
| Annual Bluegrass | 10C | 10C | 7G | 7C,8G | 7C,7G | 10C | 5G | 4C,7G | 2G | 3G |
| Green Foxtail | 6C,7G | 7C,8G | 2C,4G | 5C,8G | 3G | 7C,7G | 1C,2G | 2C,5G | 0 | 1G |
| Quackgrass | 7C,6G | 9C,7G | 6G | 4C,7G | 1C,4G | 5C,7G | 2G | 5G | 0 | 1C,2G |
| Italian Ryegrass | 10C | 10C | 7G | 5C,8G | 2C,4G | 10C | 3G | 5G | 0 | 3G |
| Ripgut Brome | 4C,6G | 6C,7G | 3C,3G | 3C,6G | 0 | 2C,3G | 2G | 3G | 0 | 0 |
| Russian Thistle | 6C,5G | 10C | 3C,3G | 8C,7G | 10C | 10C | 2C,2G | 2C,3G | 2C,3G | 10C |
| Tansy Mustard | 10C | 10C | 10C | 10C | 10C | 10C | 10C | 10C | 10C | 10C |
| Smartweed | — | — | — | — | — | — | — | — | — | — |
| Jimhill Mustard | 10C | 10C | 10C | 10C | 10C | 10C | 10C | 10C | 10C | 10C |
| Kochia | 5C,6G | 10C | 3C,7G | 5C,8G | 5C,5G | 10C | 2C,5G | 3C,6G | 0 | 7C,7G |
| Shepherd's Purse | 10C | 10C | 10C | 10C | 10C | 10C | 9C,9G | 9C,9G | 10C | 10C |
| False Chamomile | 10C | 10C | 7C,7G | 8C,8G | 10C | 10C | 5C,6G | 7C,8G | 10C | 10C |
| Black Nightshade | 8C,8G | 10C | 7C,8G | 8C,8G | 10C | 10C | 7C,7G | 7C,8G | 10C | 10C |
| Yellow Rocket | 10C | 10C | 10C | 9C,9G | 10C | 10C | 7C,8G | 7C,8G | 0 | 1C,2G |
| Wild Mustard | 10C | 10C | 9C,9G | 9C,9G | 10C | 10C | 9C,9G | 9C,9G | 10C | 10C |
| Wild Buckwheat | 3C,3G | 9C,8G | 7C,7G | 8C,8G | 8C,7G | 10C | 7C,8G | 7C,8G | 4C,3G | 8C,7G |

*80% wettable powder formulation

TEST F

The results obtained from this test demonstrate the high herbicidal activity of a compound selected from the scope of the invention when it is mixed with the water of simulated rice paddies.

The test samples were applied directly into the water of paddies three days after transplanting of M7 rice plants. The test was maintained in a greenhouse, and plant response ratings were taken 34 days after application, utilizing the rating system as previously described.

TABLE F

| | Compound No. 3 | | | |
|---|---|---|---|---|
| Treatment | Rice | Barnyard-grass | Water Chestnut | Arrowhead |
| 10 g/ha | 6G | 5E | 8G | 0 |
| 40 g/ha | 10G,4C | 10E | 10G,3C | 5F |

TEST G

A field study was conducted to determine the crop selectivity and herbicidal activities of various chemicals. The test was conducted on a Wea silt loam having an organic matter content of 2.8 percent and a pH of 7.2.

The plots were planted to sugarbeets, oats, giant foxtail, wild oats, barley, rape, wheat, soybeans, velvetleaf, dry beans, corn and sunflower. The area had a natural infestation of pigweed.

The test included both pre- and post-emergence treatments. The pre-emergence treatments were applied directly after planting. The post-emergence treatments were applied 21 days after planting. Ratings were made on the percent control of both crops and weeds at various times after application.

Pre-Emergence Test - Table G-I

The n-propyl-dimethoxypyrimidine material showed crop selectivity on wheat, corn and soybeans while controlling giant foxtail, velvetleaf and pigweed at the selected rates. The isopropyl-dimethoxypyrimidin material exhibited crop selectivity on wheat and corn. The compound controls giant foxtail and pigweed.

Post-emergence test - Table G-II

The isopropyl-dimethoxypyrimidine compound exhibited selectivity in all of the cereal crops tested (oats, barley and wheat) while some corn tolerance was noted. The compound provided control of broadleaf weeds including velvetleaf and pigweed.

The n-propyldimethoxypyrimidine exhibited selectivity in wheat, oats, corn and soybeans; it controlled pigweed and velvetleaf.

TABLE G-I

PRE-EMERGENCE FIELD TEST

| | Compound No. 9 kg ai/ha | | | | | | | | | Compound No. 3 kg ai/ha | | | | | | | | |
|---|---|---|---|---|---|---|---|---|---|---|---|---|---|---|---|---|---|---|
| | ¼ | | | ½ | | | 1/16 | | | ¼ | | | ½ | | | 1/16 | | |
| | * | + | o | * | + | o | * | + | o | * | + | o | * | + | o | * | + | o |
| Sugarbeets | 8.0 | 8.5 | 7.0 | 9.0 | 9.0 | 9.0 | 8.0 | 8.0 | 6.0 | 9.0 | 10.0 | 10.0 | 9.0 | 9.5 | 8.5 | 9.5 | 9.0 | 8.0 |
| Oats | 5.5 | 5.0 | 5.5 | 4.0 | 5.0 | 3.0 | 2.0 | 1.5 | 1.0 | 6.0 | 6.5 | 6.0 | 4.0 | 4.0 | 2.5 | 2.5 | 2.0 | 1.5 |
| Giant Foxtail | 10.0 | 9.5 | 10.0 | 9.5 | 9.0 | 5.0 | 8.5 | 5.0 | 6.0 | 10.0 | 9.5 | 8.5 | 9.5 | 8.5 | 7.5 | 10.0 | 8.5 | 6.5 |
| Wild Oats | 6.5 | 8.0 | 6.5 | 5.0 | 6.0 | 5.0 | 4.0 | 2.5 | 2.5 | 7.0 | 7.0 | 5.5 | 5.0 | 5.0 | 3.0 | 2.0 | 2.0 | 2.0 |
| Barley | 7.5 | 8.5 | 8.0 | 5.0 | 6.0 | 2.5 | 5.0 | 4.0 | 2.5 | 6.0 | 7.0 | 4.0 | 7.0 | 6.5 | 4.0 | 4.5 | 4.5 | 3.0 |
| Rape | 9.0 | 10.0 | 10.0 | 9.0 | 10.0 | 10.0 | 8.5 | 10.0 | 10.0 | 9.5 | 10.0 | 10.0 | 9.5 | 9.5 | 10.0 | 9.5 | 10.0 | 9.5 |
| Wheat | 1.0 | 2.0 | 0.5 | 1.0 | 1.0 | 1.0 | 1.0 | 0.0 | 0.0 | 2.0 | 2.5 | 0.0 | 1.0 | 1.0 | 0.0 | 0.5 | 0.5 | 0.0 |
| Soybeans | 6.0 | 3.0 | 5.5 | 3.5 | 0.5 | 1.0 | 2.0 | 1.0 | 0.0 | 8.0 | 8.0 | 9.0 | 3.5 | 2.5 | 2.5 | 5.0 | 2.0 | 3.5 |
| Velvetleaf | 6.0 | 9.5 | 9.5 | 3.5 | 9.0 | 8.0 | 0.5 | 2.5 | 1.5 | 4.0 | 8.5 | 7.5 | 4.5 | 6.0 | 1.5 | 5.0 | 4.0 | 3.5 |
| Dry Beans | 5.5 | 8.5 | 9.0 | 4.0 | 7.5 | 5.0 | 1.5 | 2.5 | 1.5 | 5.0 | 7.0 | 4.0 | 4.0 | 4.5 | 2.0 | 4.5 | 4.0 | 2.5 |
| Corn | 3.0 | 2.5 | 4.0 | 1.0 | 0.5 | 1.0 | 1.5 | 0.0 | 1.0 | 4.5 | 4.0 | 3.5 | 1.0 | 1.0 | 1.5 | 3.0 | 0.5 | 0.5 |
| Sunflower | 10.0 | 10.0 | 9.5 | 8.0 | 9.0 | 8.5 | 9.5 | 9.5 | 9.5 | 10.0 | 10.0 | 10.0 | 8.5 | 9.0 | 8.5 | 4.0 | 9.5 | 8.0 |
| Pigweed | 10.0 | 10.0 | 10.0 | 9.5 | 10.0 | 9.5 | 9.5 | 10.0 | 9.5 | 10.0 | 10.0 | 10.0 | 1.00 | 10.0 | 9.5 | 10.0 | 10.0 | 9.0 |

* Averaged plant response of two replications taken 21 days after treatment.
+ Averaged plant response of two replications taken 38 days after treatment.
o Averaged plant response of two replications taken 55 days after treatment.
Rating Scale - 0-10, 0 = no control, 10 = 100% control.

TABLE G-II

POST-EMERGENCE FIELD TEST

| | Compound No. 3 kg ai/ha | | | | | | Compound No. 9 kg ai/ha | | | | | |
|---|---|---|---|---|---|---|---|---|---|---|---|---|
| | 1/4 + | 1/16 o | 1/64 + | 1/4 o | 1/16 + | 1/64 o | 1/4 + | 1/16 o | 1/64 + | 1/4 o | 1/16 + | 1/64 o |
| Sugarbeets | 8.5 | 6.5 | 8.5 | 6.0 | 5.5 | 2.5 | 7.5 | 4.0 | 9.0 | 6.5 | 6.0 | 4.5 |
| Oats | 2.5 | 1.5 | 2.0 | 1.0 | 0.5 | 0.0 | 4.0 | 1.0 | 3.0 | 0.5 | 2.0 | 0.5 |
| Giant Foxtail | 2.5 | 3.0 | 2.5 | 2.0 | 3.5 | 2.0 | 6.5 | 3.5 | 7.0 | 6.5 | 4.5 | 4.5 |
| Wild Oats | 3.5 | 1.0 | 2.5 | 0.5 | 2.5 | 0.0 | 4.0 | 1.0 | 4.0 | 1.5 | 2.5 | 1.0 |
| Barley | 6.5 | 1.5 | 3.0 | 1.0 | 2.5 | 2.0 | 7.0 | 4.0 | 4.5 | 2.0 | 3.5 | 2.0 |
| Rape | 9.0 | 10.0 | 8.5 | 8.0 | 7.5 | 4.5 | 9.0 | 10.0 | 9.0 | 9.0 | 8.0 | 7.0 |
| Wheat | 0.0 | 0.0 | 0.0 | 0.0 | 1.0 | 0.0 | 1.0 | 0.0 | 0.0 | 0.0 | 1.0 | 0.0 |
| Soybeans | 7.0 | 6.5 | 5.5 | 3.0 | 1.5 | 1.0 | 4.0 | 2.5 | 5.0 | 2.0 | 1.5 | 0.5 |
| Velvetleaf | 8.5 | 8.0 | 8.5 | 4.5 | 7.0 | 2.5 | 10.0 | 10.0 | 9.5 | 8.5 | 8.5 | 5.0 |
| Dry Beans | 8.0 | 7.0 | 8.0 | 5.0 | 7.5 | 3.5 | 9.0 | 9.0 | 9.0 | 8.0 | 8.0 | 4.0 |
| Corn | 4.0 | 4.5 | 4.0 | 2.5 | 1.0 | 1.0 | 2.5 | 3.0 | 2.0 | 4.0 | 0.5 | 1.0 |
| Sunflower | 9.0 | 10.0 | 8.5 | 8.5 | 8.0 | 5.5 | 9.5 | 10.0 | 9.0 | 10.0 | 9.0 | 8.5 |
| **Pigweed | 9.5 | 8.5 | 9.0 | 7.5 | 7.0 | 5.0 | 9.0 | 9.0 | 9.5 | 8.5 | 9.0 | 8.5 |

+ Averaged plant response of two replications taken 17 days after treatment.
o Averaged plant response of two replications taken 34 days after treatment.
Rating scale 0-10,
0 = no control;
10 = 100% control.

TEST H

A field test site containing Matapeake silt loam soil with 10% organic matter content was plowed and disced in preparation for seeding. Just prior to final discing, 500 lbs/a of 10-10-10 fertilizer was applied to the soil. Twenty-eight crops and five weed species were drilled. Shortly after planting chemical treatments were applied to the soil surface of the plots. All treatments were replicated twice. Within five days after the application, 2.5 cm of water was applied to plots using overhead sprinkler irrigation. Evaluation of the effect of the chemicals began 30 days after application. The effect of the chemicals on crops and weeds was rated on a scale of 0–100 where 0 represented no effect and 100 represented complete kill. Untreated controls were included in the experiment for comparison. The results obtained are presented in Table H. It will be seen that certain compounds form the scope of the invention can be used for selective pre-emergence weed control in such crops as soybeans, corn, wheat, cotton, flax and lima beans.

TABLE H

Pre-Emergence Multicrop Field Test
% Effect[1]

| | Compound No. | | | | | |
|---|---|---|---|---|---|---|
| | 3 | | | 9 | | |
| kg ai/ha | .031 | .062 | .125 | .062 | .125 | .250 |
| Safflower | 0 | 0 | 0 | 5 | 65 | 90 |
| Sunflower | 0 | 0 | 0 | 0 | 45 | 90 |
| Corn | 0 | 0 | 5 | 0 | 5 | 0 |
| Sorghum | 5 | 0 | 5 | 0 | 30 | 90 |
| Clover | 0 | 0 | 0 | 0 | 0 | 20 |
| Alfalfa | 0 | 0 | 0 | 0 | 10 | 30 |
| Soybeans | 0 | 0 | 5 | 0 | 0 | 0 |
| Suarbeets | 0 | 0 | 0 | 0 | 0 | 30 |
| Rape | 0 | 0 | 5 | 15 | 85 | 100 |
| Squash | 0 | 0 | 0 | 0 | 0 | 60 |
| Potatoes | 0 | 0 | 5 | 0 | 15 | 40 |
| Cucumbers | 10 | 0 | 0 | 20 | 5 | 20 |
| Lespedela | 0 | 0 | 10 | 0 | 0 | 30 |
| Wheat | 0 | 0 | 0 | 0 | 0 | 0 |
| Rice | 45 | 0 | 10 | 0 | 0 | 70 |
| Okra | 0 | 0 | 5 | 0 | 0 | 10 |
| Oats | 0 | 0 | 0 | 0 | 0 | 60 |
| Cotton | 0 | 0 | 0 | 0 | 0 | 0 |
| Carrots | 0 | 0 | 0 | 0 | 5 | 80 |
| Red beets | 0 | 0 | 0 | 5 | 5 | 20 |
| Cabbage | 0 | 0 | 0 | 0 | 35 | 90 |
| Endive | 0 | 0 | 10 | 0 | 0 | — |
| Flax | 5 | 0 | 0 | 0 | 0 | 0 |
| Spinach | 10 | 0 | 5 | 0 | 0 | 70 |
| Snap beans | 10 | 0 | 5 | 0 | 0 | 0 |
| Tomatoe | 0 | 0 | 5 | 10 | 0 | 10 |
| Peanuts | — | — | — | — | — | — |
| Lima beans | 0 | 0 | 0 | 15 | 0 | 0 |
| Velvetleaf | 0 | 0 | 0 | 0 | 0 | 70 |
| Wild Oats | 0 | 0 | 0 | 0 | 25 | 10 |
| Ryegrass | 0 | 0 | .5 | 5 | 35 | 20 |
| Barnyardgrass | 0 | 0 | 0 | 0 | 25 | 60 |
| Foxtail | 5 | 5 | 15 | 10 | 35 | 70 |
| Crabgrass | 0 | 0 | 0 | 0 | 30 | 70 |
| Ragweed | 10 | 0 | 5 | 5 | 35 | 70 |
| lambsquarter | 15 | 0 | 25 | 10 | 25 | 60 |
| Smartweed | 0 | — | 10 | 0 | 30 | 70 |
| Purscane | — | 0 | 0 | — | — | — |
| Jimsonweed | 0 | — | — | 0 | 0 | 60 |
| Pigweed | 0 | 0 | — | 0 | — | 60 |
| Moringglory | 0 | 0 | 0 | 0 | 0 | 50 |
| Nutsedge | 0 | 0 | 0 | 0 | 0 | — |
| Flower-of-an Hour | 15 | 0 | 10 | 10 | 10 | 70 |

[1]0 = no effect; 100 = complete kill.

TEST I

A post-emergence field test was conducted using the same plantings as described in Test H. Twenty-one days after planting, chemical treatments were applied to emerged crops and weeds in each plot. All treatments were applied in water containing 0.1% surfactant and were replicated twice. Evaluation began 30 days after application. Again, the effect of a treatment on crops and weeds was rated on a scale of 0–100, where 0=no effect and 100=complete kill. Untreated controls were included in the experiment for comparison. The data are summarized in Table I.

The compounds tested provided excellent post-emergence weed control in a number of crops, including corn, wheat, oats, potatoes, flax and tomatoes.

TABLE I

Post-Emergence Multicrop Field Test
% Effect[1]

| | Compound No. | | | | | |
|---|---|---|---|---|---|---|
| | 3 | | | 9 | | |
| kg ai/ha | .015 | .031 | .062 | .031 | .062 | .125 |
| Safflower | 85 | 90 | 95 | 90 | 100 | 100 |
| Sunflower | 90 | 90 | 90 | 95 | 100 | 100 |
| Corn | 0 | 20 | 45 | 0 | 0 | 0 |
| Sorghum | 90 | 90 | 90 | 95 | 90 | 95 |
| Clover | 25 | 50 | 65 | 65 | 75 | 85 |
| Alfalfa | 55 | 55 | 75 | 65 | 70 | 70 |
| Soybeans | 25 | 50 | 65 | 25 | 50 | 70 |
| Sugarbeets | 15 | 15 | 50 | 25 | 30 | 35 |
| Rape | 55 | 75 | 65 | 95 | 95 | 100 |
| Squash | 65 | 70 | 80 | 85 | 85 | 95 |
| Potatoes | 0 | 5 | 10 | 0 | 0 | 15 |
| Cucumbers | 30 | 45 | 45 | 5 | 10 | 35 |
| Lespedela | 70 | 65 | 70 | 70 | 70 | 95 |
| Wheat | 0 | 0 | 20 | 0 | 0 | 0 |
| Rice | 25 | 30 | 30 | 35 | 40 | 45 |
| Okra | 10 | 60 | 55 | 55 | 60 | 65 |
| Oats | 0 | 5 | 10 | 0 | 0 | 15 |
| Cotton | 45 | 50 | 70 | 80 | 70 | 70 |
| Carrots | 20 | 40 | 85 | 90 | 85 | 95 |
| Red beets | 30 | 45 | 90 | 90 | 90 | 95 |
| Cabbage | 25 | 60 | 75 | 80 | 90 | 100 |
| Endive | 20 | — | — | — | — | — |
| Flax | 0 | 20 | 15 | 10 | 25 | 45 |
| Spinach | 45 | 90 | 90 | 90 | 95 | 100 |
| Snap beans | 55 | 65 | 75 | 55 | 80 | 85 |
| Tomatoe | 5 | 0 | 10 | 0 | 5 | 15 |
| Peanuts | — | — | — | — | — | — |
| Lima beans | 5 | 60 | 70 | 80 | 85 | 90 |
| Velvetleaf | 55 | 95 | 95 | 90 | 100 | 100 |
| Wild Oats | 10 | 10 | 15 | 5 | 40 | 30 |
| Ryegrass | 5 | 5 | 25 | 20 | 70 | 60 |
| Barnyardgrass | 0 | 0 | 10 | 80 | 90 | 90 |
| Foxtail | 10 | 5 | 35 | 5 | 40 | 50 |
| Crabgrass | — | 0 | 40 | — | 10 | — |
| Ragweed | 55 | 70 | 85 | 70 | 80 | 85 |
| Lambsquarter | 30 | 90 | 75 | 55 | 70 | 70 |
| Smartweed | — | — | 80 | 60 | 90 | 80 |
| Purscane | — | — | 90 | — | 90 | 85 |
| Jimsonweed | — | — | 30 | 0 | — | 0 |
| Pigweed | 40 | 90 | 85 | 80 | 90 | 85 |
| Moringglory | — | — | — | — | — | — |
| Nutsedge | — | — | — | 0 | — | — |
| Flower-of-an Hour | 70 | 80 | 75 | 70 | 90 | 80 |

[1]0 = no effect; 100 = complete kill.

TEST J

In a pre-emergence field test study, Matapeake silt loam soil with 1% organic matter content was plowed and disked in preparation for seeding. Just prior to final discing 500 lbs/a of 10-10-10 fertilizer was applied to the soil. Corn was planted into single row plots. Shortly after planting, chemical treatments were applied to the soil surface of the plots. All treatments were applied in water. The experiment was designed as a partially randomized complete block with 3 replications. The first replication was layed out in numerical sequence and not randomized. Evaluation of treatments began 43 days after application. The effect of a treatment on crops and indigenous weeds was rated on a scale of 0–100, where 0=no effect and 100=complete kill. Untreated controls were included in the experiment for comparison. The results obtained are given in Table J.

It will be apparent from Table J that the compound tested can be used for selective pre-emergence weed control in corn.

TABLE J

| | Pre-Emergence Corn Field Test % Effect[1] | | | | | |
|---|---|---|---|---|---|---|
| | Compound No. 9 | | | | Untreated Control | |
| kg ai/ha | 0.031 | 0.062 | 0.125 | 0.250 | Cult. | Uncult. |
| Corn | 0 | 3 | 0 | 7 | 0 | 0 |
| Fall Panicum | 53 | 73 | 80 | 93 | — | 0 |
| Crabgrass | 43 | 57 | 70 | 90 | — | 0 |
| Yellow Foxtail | 53 | 63 | 80 | 90 | — | 0 |
| Purslane | 70 | 87 | 86 | 96 | — | 0 |
| Flower-of-an-hour | 53 | 70 | 80 | 90 | — | 0 |
| Galinsoga | — | — | — | — | — | 0 |
| Velvetleaf | 33 | 57 | 90 | 90 | — | 0 |

[1]% effect: 0 = no effect; 100 = complete kill. Average of 3 replications.

TEST K

For a post-emergence field test, a site as described in Test J was selected. Twenty-one days after planting the corn chemical treatments were applied to the emerged crop and weeds in each plot. Each treatment included applications to both previously untreated plots and to plots which earlier had received a pre-emergence application of alachlor herbicide. All treatments were applied in water. The experiment was designed as a partially randomized complete block wtih 3 replications. The first replication was layed out in numerical sequence and not randomized. Evaluation of treatments began 39 days after application. The effect of a chemical on corn and indigenous weeds was rated on a scale of 0-100, where 0 is no effect and 10 is complete kill. Untreated controls were included in the experiment for comparison. The data, shown in Table K, indicate the potential utility of a compound from the scope of the present invention for selective post-emergence weed control in corn, both when applied by itself or in conjunction with a prior pre-emergence treatment of alachlor.

TABLE K

| | Post-emergence Corn Field Test % Effect | | | | | |
|---|---|---|---|---|---|---|
| | Compound No. 9 | | | | | |
| kg ai/ha | 0.031 | 0.062 | 0.125 | 0.250 | Cult | Uncult |
| w/o Alachlor | | | | | | |
| Corn | 0 | 7 | 0 | 30 | 0 | 3 |
| Fall Panicum | 0 | 7 | 20 | 27 | — | 0 |
| Purslane | 37 | 60 | 53 | 70 | — | 0 |
| Galinsoga | — | — | — | — | — | 0 |
| Flower-of-an-Hour | — | — | — | 80 | — | 0 |
| with Alachlor | | | | | | |
| Corn | 0 | 3 | 0 | 23 | 0 | 0 |
| Fall Panicum | 100 | 100 | 100 | 97 | — | 100 |
| Purslane | 100 | 100 | 100 | 100 | — | 97 |
| Galinsoga | 100 | 100 | — | 100 | — | 100 |
| Flower-of-an-Hour | 95 | 100 | — | 100 | — | 87 |

[1]% Effect, 0 = no effect, 100 = complete kill.

TEST L

This field test was conducted on a site as previously described for tests H through K. Wheat, wild oats and mustard were drilled into plots. Herbicide treatments were applied in the spring when wheat was fully tillered and 12-20 cm tall. All treatments were applied in water. The experiment was designed as a partially randomized complete block with 3 replications. The first replication was layed out in numerical sequence and not randomized. Evaluation of treatments began 25 days after application. The effect of a treatment on crops and weeds was rated on a scale of 0-100, where 0=no effect and 100=complete kill. Untreated controls were included in the experiment for comparison. The data, presented in Table L, indicate that the test compound provides control of certain weed species without injuring the crop when applied post-emergence to wheat.

TABLE L

| | Post-Emergence Spring Wheat Field Test % Effect[1] | | | | |
|---|---|---|---|---|---|
| | Compound No. 3 | | | | Untreated Control |
| kg ai/ha | .008 | .015 | .031 | .062 | |
| Wheat | 0 | 0 | 0 | 0 | 0 |
| Yellow Foxtail | 0 | 3 | 7 | 7 | 0 |
| Ragweed | 0 | 7 | 17 | 27 | 0 |
| Wild Oats | 0 | 0 | 0 | 0 | 0 |
| Velvetleaf | 3 | 7 | 3 | 3 | 0 |
| Flower-of-an-hour | 3 | 10 | 3 | 3 | 0 |
| Mustard | 40 | 65 | — | — | 0 |
| Wheat Yield[2] | 169 | 223 | 190 | 259 | 203 |

[1]% Effect - 0 = no effect, 100 = complete kill; Average of 3 replicates.
[2]Wheat Yield - Yield from all 4 rows/plot. Data Average of 3 replicates.

TEST M

For a pre-plant incorporated field test on winter wheat, a Keyport silt loam with 1% organic matter content was plowed and disked in preparation for fall seeding. Just prior to final disking 500 lbs/a of 10-10-10 fertilizer was applied to the field. Chemical treatments were then applied to the soil surface of plots. All chemicals were applied in water. Immediately after application the chemical was incorporated into the upper 5 cm of soil utilizing a rototiller. Wheat, wild oats and wild mustard were then drilled into plots. The experiment was designed as a partially randomized complete block with 3 replications. The first replication was layed out in numerical sequence and not randomized. Evaluation of the treatments was made 31 days after application. The effect of a chemical on wheat and weeds was rated on a scale of 0-100, where 0=no effect and 100=complete kill. Untreated controls were included in the experiment for comparison. The test results are tabulated in Table L. The test chemicals used as pre-plant incorporated treatments provided excellent control of mustard without causing injury to the wheat crop.

TABLE M

| Pre-plant incorporate field test on wheat % Effect[1] (31 days after treatment) | | | | |
|---|---|---|---|---|
| Compound No. | Kg ai/ha | Wheat | Wild Oats | Wild Mustard |
| 3 | .062 | 0 | 0 | 60 |
| | .125 | 0 | 0 | 90 |
| | .250 | 0 | 3 | 90 |
| 9 | .062 | 0 | 0 | 90 |
| | .125 | 0 | 0 | 90 |
| | .250 | 3 | 3 | 90 |
| Untreated Control | — | 0 | 0 | 0 |

[1]% Effect - 0 = no effect, 100 = complete kill.

TEST N

For a pre-emergence field test on winter wheat, a site as described in Test M was selected. Wheat, wild oats and wild mustard were drilled into the plots and herbicide treatments were applied to the soil surface of the plots immediately after planting. All treatments were applied in water. The experiment was designed as a partially randomized complete block with 3 replications. The first replication was layed out in numerical sequence and not randomized. Evaluation of treatments were made 31 days after application. The effect of a chemical on wheat and weeds was rated on a scale of 0-100, where 0 = no effect and 10 = complete kill. Untreated controls were included in the experiment for comparison. The ratings are presented in Table N.

The chemicals used in this test provide excellent pre-emergence weed control in wheat.

TABLE N

Pre-emergence Field Test on Wheat
% Effect[1]
(31 days after treatment)

| Compound No. | kg ai/ha | Wheat | Wild Oats | Wild Mustard |
|---|---|---|---|---|
| 3 | .062 | 0 | 0 | 83 |
|  | .125 | 0 | 0 | 90 |
|  | .250 | 0 | 0 | 90 |
| 9 | .062 | 3 | 0 | 90 |
|  | .125 | 0 | 0 | 90 |
|  | .250 | 3 | 10 | 90 |
| Untreated Control | — | 0 | 0 | 0 |

[1] % Effect - 0 = no effect, 100 = complete kill.

What is claimed is:

1. The compound N-[(4-methoxy-6-methylpyrimidin-2-yl)-aminocarbonyl]-2-(propylsulfinyl)benzenesulfonamide.

2. A composition suitable for controlling the growth of undesired vegetation which comprises an effective amount of a compound of claim 1 and at least one of the following: surfactant, solid or liquid diluent.

3. A method for controlling growth of undesired vegetation which comprises applying to the locus to be protected an effective amount of the compound of claim 1.

* * * * *

UNITED STATES PATENT AND TRADEMARK OFFICE
CERTIFICATE OF CORRECTION

PATENT NO. : 4,818,277
DATED : April 4, 1989
INVENTOR(S) : George Levitt It is certified that error appears in the above-identified patent and that said Letters Patent is hereby corrected as shown below:

On the title page, Item [19], "George" should read -- Levitt --.

Item [75], "Levitt George" should read
                              -- George Levitt --.

Signed and Sealed this

Twenty-seventh Day of February, 1990

*Attest:*

JEFFREY M. SAMUELS

*Attesting Officer*   *Acting Commissioner of Patents and Trademarks*